United States Patent
Banner et al.

(10) Patent No.: US 8,389,513 B2
(45) Date of Patent: Mar. 5, 2013

(54) 2-AMINO-5,5-DIFLUORO-5,6-DIHYDRO-4H-[1,3]OXAZIN-4-YL)-PHENYL]-AMIDES

(75) Inventors: David Banner, Basel (CH); Wolfgang Guba, Muellheim (DE); Hans Hilpert, Muenchenstein (CH); Harald Mauser, Birsfelden (CH); Alexander V. Mayweg, Basel (CH); Robert Narquizian, Zaessingue (FR); Emmanuel Pinard, Linsdorf (FR); Eoin Power, Siena (IT); Mark Rogers-Evans, Bottmingen (CH); Thomas Woltering, Freiburg (DE); Wolfgang Wostl, Grenzach-Wyhlen (DE)

(73) Assignees: Hoffmann-La Roche Inc., Nutley, NJ (US); Siena Biotech S.p.A., Siena (IT)

( * ) Notice: Subject to any disclaimer, the term of this patent is extended or adjusted under 35 U.S.C. 154(b) by 209 days.

(21) Appl. No.: 12/959,412

(22) Filed: Dec. 3, 2010

(65) Prior Publication Data
US 2011/0144097 A1 Jun. 16, 2011

(30) Foreign Application Priority Data
Dec. 11, 2009 (EP) .................................. 09178983

(51) Int. Cl.
*C07D 265/04* (2006.01)
*A61K 31/33* (2006.01)
(52) U.S. Cl. ........................... 514/228.8; 544/88; 544/96
(58) Field of Classification Search .................... 544/88, 544/96; 514/228.8
See application file for complete search history.

(56) References Cited

U.S. PATENT DOCUMENTS
6,759,402 B2 * 7/2004 Macdonald et al. .......... 514/183

FOREIGN PATENT DOCUMENTS
| EP | 1942105 | 7/2008 |
| EP | 2147914 | 1/2010 |
| WO | 2008/133273 | 11/2008 |
| WO | 2008/133274 | 11/2008 |
| WO | 2009/103626 | 8/2009 |
| WO | 2011/009943 | 1/2011 |
| WO | 2007/049532 | 4/2011 |

OTHER PUBLICATIONS

Hardy et al., Science vol. 297 (2002) pp. 353-356.
Selkoe, D., Annual Review in Cell Biology vol. 10 (1994) pp. 373-403.
Vassar et al., Science vol. 286 (1999) pp. 735-741.
Luo et al., National Neuroscience vol. 4(3) (2001) pp. 231-232.
Roberds et al., Human Molecule Genetics vol. 10(12) (2001) pp. 1317-1324.
McConlogue et al., Journal of Biological Chemistry vol. 282(36) (2007) pp. 26326-26334.
Prentki et al., Journal of Clinical Investigation vol. 116(7) (2006) pp. 1802-1812.
Wild et al., Diabetes Care vol. 27(5) (2004) pp. 1047-1053.
Zimmet et al., Nature vol. 414 (2001) pp. 782-787.
Baggio et al., Annual Review of Medicine vol. 57 (2006) pp. 265-281.
Akpinar et al., Cell Metabolism vol. 2 (2005) pp. 385-397.
Fukui et al., Cell Metabolism vol. 2 (2005) pp. 373-384.
Finzi et al., Ultrastruct. Pathology vol. 32(6) (2008) pp. 246-251.
Hussain et al., Molecular & Cellular Neurosciences vol. 16 (2000) pp. 609-619.
Kuhn et al., Journal of Biological Chemistry vol. 282(16) (2007) pp. 11982-11995.
Vattemi et al., Lancet vol. 358 (2001) pp. 1962-1964.
Barbiero et al., Experimental Neurology vol. 182(2) (2003) pp. 335-345.
Sugimoto et al., Journal of Biological Chemistry vol. 282(48) (2007) pp. 34896-34903.
Desnues et al., Clinical Vaccine Immunology vol. 13(2) (2006) pp. 170-178.
Gatcher et al., Proceedings of National Academy of Sciences USA vol. 105(4) (2008) pp. 1291-1296.
Greenberg et al., Annals of Neurology vol. 57(5) (2005) pp. 664-678.
Lagos et al., Blood vol. 109(4) (2007) pp. 1550-1558.
Koistinen et al., Muscle & Nerve vol. 34(4) (2006) pp. 444-450.
Li et al., Aging Cell vol. 5(2) (2006) pp. 153-165.
Kim et al., Neurobiology of Disease vol. 22(2) (2006) pp. 346-356.
Hodges et al., Human Molecular Genetics vol. 15(6) (2006) pp. 965-977.
Kihara et al., Proceedings of National Academy of Sciences vol. 106(51) (2009) pp. 21807-21812.

(Continued)

*Primary Examiner* — Kahsay T Habte
(74) *Attorney, Agent, or Firm* — George W. Johnston; Patricia S. Rocha-Tramaloni; Kimberly J. Prior

(57) ABSTRACT

The present invention relates to 2-Amino-5,5-difluoro-5,6-dihydro-4H-[1,3]oxazin-4-yl)-phenyl]-amides of formula I

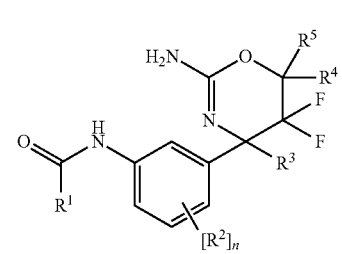

having BACE1 and/or BACE2 inhibitory activity, their manufacture, pharmaceutical compositions containing them and their use as therapeutically active substances. The active compounds of the present invention are useful in the therapeutic and/or prophylactic treatment of e.g. Alzheimer's disease and type 2 diabetes.

31 Claims, No Drawings

OTHER PUBLICATIONS

Talantov et al., Clinical Cancer Research vol. 11(20) (2005) pp. 7234-7242.
Basset et al., Scandinavian Journal of Immunology vol. 51(3) (2000) pp. 307-311.
Grewal et al., Molecular Cellular Biology vol. 126(13) (2006) pp. 4970-4981.
Hedlund et al., Cancer Research vol. 68(2) (2008) pp. 388-394.
Kondoh et al., Breast Cancer Research & Treatment vol. 78(1) (2003) pp. 37-44.
Hoffmeister et al., JOP, vol. 10(5) (2009) pp. 501-506.
Woodard=Grice et al., Journal of Biological Chemistry vol. 283)39) (2008) pp. 26364-26373.
Toegel et al., Osteoarthritis & Cartilage vol. 18(2) (2010) pp. 240-248.
Lichtenthaler et al., Journal of Biological Chemistry vol. 278(49) (2003) pp. 48713-48719.
Merten et al., Z Kardiol. vol. 93(11) (2004) pp. 855-863.
Maugeri et al., Srp Arh Celok Lek. Suppl. 1 (2010) pp. 50-52.
Kiljanski et al. Thyroid vol. 15(7) (2005) pp. 645-652.
PCT International Search Report PCT/EP2010/068912—issued Mar. 29, 2011.
English language translation of Document 38 (non-patent literature), (2010).
Huang, W-H et al., Current Medicinal Chemistry 16:1806-1820 (2009).
(Costa Rican Oppostion by Asociacion De La Industria Farmaceutical Nacional Jul. 31,2012).

\* cited by examiner

2-AMINO-5,5-DIFLUORO-5,6-DIHYDRO-4H-[1,3]OXAZIN-4-YL)-PHENYL]-AMIDES

PRIORITY TO RELATED APPLICATION(S)

This application claims the benefit of European Patent Application No. 09178983.4, filed Dec. 11, 2009, which is hereby incorporated by reference in its entirety.

BACKGROUND OF THE INVENTION

Alzheimer's disease (AD) is a neurodegenerative disorder of the central nervous system and the leading cause of a progressive dementia in the elderly population. Its clinical symptoms are impairment of memory, cognition, temporal and local orientation, judgment and reasoning but also severe emotional disturbances. There are currently no treatments available which can prevent the disease or its progression or stably reverse its clinical symptoms. AD has become a major health problem in all societies with high life expectancies and also a significant economic burden for their health systems.

AD is characterized by 2 major pathologies in the central nervous system (CNS), the occurrence of amyloid plaques and neurofibrillar tangles (Hardy et al., The amyloid hypothesis of Alzheimer's disease: progress and problems on the road to therapeutics, *Science*. 2002 Jul. 19; 297(5580):353-6, Selkoe, Cell biology of the amyloid beta-protein precursor and the mechanism of Alzheimer's disease, *Annu Rev Cell Biol*. 1994; 10:373-403). Both pathologies are also commonly observed in patients with Down's syndrome (trisomy 21), which also develop AD-like symptoms in early life. Neurofibrillar tangles are intracellular aggregates of the microtubule-associated protein tau (MAPT). Amyloid plaques occur in the extracellular space, their principal components are Aβ-peptides. The latter are a group of proteolytic fragments derived from the β-amyloid precursor protein (APP) by a series of proteolytic cleavage steps. Several forms of APP have been identified of which the most abundant are proteins of 695, 751 and 770 amino acids length. They all arise from a single gene through differential splicing. The Aβ-peptides are derived from the same domain of the APP but differ at their N- and C-termini, the main species are of 40 and 42 amino-acid length. There are several lines of evidence which strongly suggest that aggregated Aβ-peptides are the essential molecules in the pathogenesis of AD: 1) amyloid plaques formed of Aβ-peptides are invariably part of the AD pathology; 2) Aβ-peptides are toxic for neurons; 3) in Familial Alzheimer's Disease (FAD) the mutations in the disease genes APP, PSN1, PSN2 lead to increased levels of Aβ-peptides and early brain amyloidosis; 4) transgenic mice which express such FAD genes develop a pathology which bears many resemblances to the human disease. Aβ-peptides are produced from APP through the sequential action of 2 proteolytic enzymes termed β- and γ-secretase. β-Secretase cleaves first in the extracellular domain of APP approximately 28 amino acids outside of the trans-membrane domain (TM) to produce a C-terminal fragment of APP containing the TM- and the cytoplasmatic domain (CTFβ). CTFβ is the substrate for γ-secretase which cleaves at several adjacent positions within the TM to produce the Aβ peptides and the cytoplasmic fragment. The γ-secretase is a complex of at least 4 different proteins, its catalytic subunit is very likely a presenilin protein (PSEN1, PSEN2). The β-secretase (BACE1, Asp2; BACE stands for β-site APP-cleaving enzyme) is an aspartyl protease which is anchored into the membrane by a transmembrane domain (Vassar et al., Beta-secretase cleavage of Alzheimer's amyloid precursor protein by the transmembrane aspartic protease BACE, *Science*. 1999 Oct. 22; 286(5440):735). It is expressed in many tissues of the human organism but its level is especially high in the CNS. Genetic ablation of the BACE1 gene in mice has clearly shown that its activity is essential for the processing of APP which leads to the generation of Aβ-peptides, in the absence of BACE1 no Aβ-peptides are produced (Luo et al., Mice deficient in BACE1, the Alzheimer's beta-secretase, have normal phenotype and abolished beta-amyloid generation, *Nat. Neurosci.* 2001 March; 4(3):231-2, Roberds et al., BACE knockout mice are healthy despite lacking the primary beta-secretase activity in brain: implications for Alzheimer's disease therapeutics, *Hum Mol. Genet.* 2001 Jun. 1; 10(12):1317-24). Mice which have been genetically engineered to express the human APP gene and which form extensive amyloid plaques and Alzheimer's disease like pathologies during aging fail to do so when β-secretase activity is reduced by genetic ablation of one of the BACE1 alleles (McConlogue et al., Partial reduction of BACE1 has dramatic effects on Alzheimer plaque and synaptic pathology in APP Transgenic Mice. *J Biol. Chem.* 2007 Sep. 7; 282(36):26326). It is thus presumed that inhibitors of BACE1 activity can be useful agents for therapeutic intervention in Alzheimer's Disease (AD).

Type 2 diabetes (T2D) is caused by insulin resistance and inadequate insulin secretion from pancreatic β-cells leading to poor blood-glucose control and hyperglycemia (M Prentki & C J Nolan, "Islet beta-cell failure in type 2 diabetes." J. Clin. Investig. 2006, 116(7), 1802-1812). Patients with T2D have an increased risk of microvascular and macrovascular disease and a range of related complications including diabetic nephropathy, retinopathy and cardiovascular disease. In 2000, an estimated 171 million people had the condition with the expectation that this figure will double by 2030 (S Wild, G Roglic, A Green, R. Sicree & H King, "Global prevalence of diabetes", Diabetes Care 2004, 27(5), 1047-1053), making the disease a major healthcare problem. The rise in prevalence of T2D is associated with an increasingly sedentary lifestyle and high-energy food intake of the world's population (P Zimmet, KGMM Alberti & J Shaw, "Global and societal implications of the diabetes epidemic" Nature 2001, 414, 782-787). β-Cell failure and consequent dramatic decline in insulin secretion and hyperglycemia marks the onset of T2D. Most current treatments do not prevent the loss of β-cell mass characterizing overt T2D. However, recent developments with GLP-1 analogues, gastrin and other agents show that preservation and proliferation of β-cells is possible to achieve, leading to an improved glucose tolerance and slower progression to overt T2D (L L Baggio & D J Drucker, "Therapeutic approaches to preserve islet mass in type 2 diabetes", Annu Rev. Med. 2006, 57, 265-281). Tmem27 has been identified as a protein promoting beta-cell proliferation (P Akpinar, S Kuwajima, J Krützfeldt, M Stoffel, "Tmem27: A cleaved and shed plasma membrane protein that stimulates pancreatic β cell proliferation", Cell Metab. 2005, 2, 385-397) and insulin secretion (K Fukui, Q Yang, Y Cao, N Takahashi et al., "The HNF-1 target Collectrin controls insulin exocytosis by SNARE complex formation", Cell Metab. 2005, 2, 373-384). Tmem27 is a 42 kDa membrane glycoprotein which is constitutively shed from the surface of β-cells, resulting from a degradation of the full-length cellular Tmem27. Overexpression of Tmem27 in a transgenic mouse increases β-cell mass and improves glucose tolerance in a diet-induced obesity DIO model of diabetes. Furthermore, siRNA knockout of Tmem27 in a rodent β-cell proliferation assay (e.g. using INS1e cells) reduces the proliferation rate, indicating a role for Tmem27 in control of β-cell mass.

In the same proliferation assay, BACE2 inhibitors also increase proliferation. However, BACE2 inhibition combined with Tmem27 siRNA knockdown results in low proliferation rates. Therefore, it is concluded that BACE2 is the protease responsible for the degradation of Tmem27. Furthermore, in vitro, BACE2 cleaves a peptide based on the sequence of Tmem27. The closely related protease BACE1 does not cleave this peptide and selective inhibition of BACE1 alone does not enhance proliferation of β-cells.

The close homolog BACE2 is a membrane-bound aspartyl protease and is co-localized with Tmem27 in human pancreatic β-cells (G Finzi, F Franzi, C Placidi, F Acquati et al., "BACE2 is stored in secretory granules of mouse and rat pancreatic beta cells", Ultrastruct Pathol. 2008, 32(6), 246-251). It is also known to be capable of degrading APP (I Hussain, D Powell, D Howlett, G Chapman et al., "ASP1 (BACE2) cleaves the amyloid precursor protein at the β-secretase site" Mol Cell Neurosci. 2000, 16, 609-619), IL-1R2 (P Kuhn, E Marjaux, A Imhof, B De Strooper et al., "Regulated intramembrane proteolysis of the interleukin-1 receptor II by alpha-, beta-, and gamma-secretase" J. Biol. Chem. 2007, 282(16), 11982-11995) and ACE2. The capability to degrade ACE2 indicates a possible role of BACE2 in the control of hypertension.

Inhibition of BACE2 is therefore proposed as a treatment for T2D with the potential to preserve and restore β-cell mass and stimulate insulin secretion in pre-diabetic and diabetic patients. It is therefore an object of the present invention to provide selective BACE2 inhibitors. Such compounds are useful as therapeutically active substances, particularly in the treatment and/or prevention of diseases which are associated with the inhibition of BACE2.

Furthermore, the formation, or formation and deposition, of β-amyloid peptides in, on or around neurological tissue (e.g., the brain) are inhibited by the present compounds, i.e. inhibition of the Aβ-production from APP or an APP fragment.

WO 2007/049 532 and WO 2008/133 274 describe aminodihydrothiazines as BACE1 inhibitors, and WO 2008/133 273 describes pharmaceutical compositions of BACE1 inhibitors.

Inhibitors of BACE1 and/or BACE2 can in addition be used to treat the following diseases: IBM (inclusion body myositis) (Vattemi G. et al., Lancet. 2001 Dec. 8; 358(9297): 1962-4), Down's Syndrome (Barbiero L. et al, Exp Neurol. 2003 August; 182(2):335-45), Wilson's Disease (Sugimoto I. et al., J Biol. Chem. 2007 Nov. 30; 282(48):34896-903), Whipple's disease (Desnues B. et al., Clin Vaccine Immunol. 2006 February; 13(2):170-8), SpinoCerebellar Ataxia 1 and SpinoCerebellar Ataxia 7 (Gatchel J. R. et al., *Proc Natl Acad Sci USA* 2008 Jan. 29; 105(4):1291-6), Dermatomyositis (Greenberg S. A. et al., Ann Neurol. 2005 May; 57(5):664-78 and Greenberg S. A. et al., *Neurol* 2005 May; 57(5):664-78), Kaposi Sarcoma (Lagos D. et al, Blood, 2007 Feb. 15; 109 (4):1550-8), Glioblastoma multiforme (E-MEXP-2576, http://www.ebi.ac.uk/microarray-as/aer/ result?queryFor=PhysicalArrayDesign&aAccession=A-MEXP-258), Rheumatoid arthritis (Ungethuem U. et al, GSE2053), Amyotrophic lateral sclerosis (Koistinen H. et al., Muscle Nerve. 2006 October; 34(4):444-50 and Li Q. X. et al, Aging Cell. 2006 April; 5(2):153-65), Huntington's Disease (Kim Y. J. et al., Neurobiol Dis. 2006 May; 22(2):346-56. Epub 2006 Jan. 19 and Hodges A. et al., Hum Mol. Genet. 2006 Mar. 15; 15(6):965-77. Epub 2006 Feb. 8), Multiple Mieloma (Kihara Y. et al, Proc Natl Acad Sci U S A. 2009 Dec. 22; 106(51):21807-12), Malignant melanoma (Talantov D. et al, Clin Cancer Res. 2005 Oct. 15; 11(20):7234-42), Sjogren syndrome (Basset C. et al., Scand J. Immunol. 2000 March; 51(3):307-11), Lupus erythematosus (Grewal P. K. et al, Mol Cell Biol. 2006, July; 26(13):4970-81), Macrophagic myofasciitis, juvenile idiopathic arthritis, granulomatous arthritis, Breast cancer (Hedlund M. et al, Cancer Res. 2008 Jan. 15; 68(2):388-94 and Kondoh K. et al., Breast Cancer Res Treat. 2003 March; 78(1):37-44), Gastrointestinal diseases (Hoffmeister A. et al, JOP. 2009 Sep. 4; 10(5):501-6), Autoimmune/inflammatory diseases (Woodard-Grice A. V. et al., J Biol. Chem. 2008 Sep. 26; 283(39):26364-73. Epub 2008 Jul. 23), Rheumatoid Arthritis (Toegel S. et al, Osteoarthritis Cartilage. 2010 February; 18(2):240-8. Epub 2009 Sep. 22), Inflammatory reactions (Lichtenthaler S. F. et al., J Biol. Chem. 2003 Dec. 5; 278(49):48713-9. Epub 2003 Sep. 24), Arterial Thrombosis (Merten M. et al., Z Kardiol. 2004 November; 93(11):855-63), Cardiovascular diseases such as Myocardial infarction and stroke (Maugeri N. et al., Srp Arh Celok Lek. 2010 January; 138 Suppl 1:50-2) and Graves disease (Kiljański J. et al, Thyroid. 2005 July; 15(7):645-52).

SUMMARY OF THE INVENTION

The present invention provides 2-amino-5,5-difluoro-5,6-dihydro-4H-[1,3]oxazin-4-yl)-phenyl]-amides having BACE1 and/or BACE2 inhibitory properties, their manufacture, pharmaceutical compositions containing them and their use as therapeutically active substances.

The present invention provides compounds of formula I,

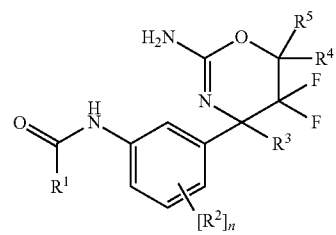

wherein the substituents and variables are as described below, or a pharmaceutically acceptable salt thereof.

The present compounds have Asp2 (β-secretase, BACE1 or Memapsin-2) inhibitory activity and therefore are useful in the therapeutic and/or prophylactic treatment of diseases and disorders characterized by elevated β-amyloid levels and/or β-amyloid oligomers and/or β-amyloid plaques and further deposits, particularly Alzheimer's disease. And/or the present compounds have BACE2 inhibitory activity and can therefore be used in the therapeutic and/or prophylactic treatment of diseases and disorders such as type 2 diabetes and other metabolic disorders.

The present invention provides compounds of formula I per se and their pharmaceutically acceptable salts thereof and pharmaceutical compositions containing such compounds. The invention also provides methods for the preparation the compounds and compositions of the invention.

The compounds of the invention are useful for the treatment of diseases and disorders which are associated with inhibition of BACE1 and/or BACE2 activity, such as Alzheimer's disease and type 2 diabetes. Furthermore, the formation, or formation and deposition, of β-amyloid plaques in, on or around neurological tissue (e.g., the brain) are inhibited by the present compounds by inhibiting the Aβ production from APP or an APP fragment.

The invention further provides a method for the treatment of Alzheimer's disease, type 2 diabetes, amyotrophic lateral sclerosis (ALS), arterial thrombosis, autoimmune/inflammatory disease, cancer such as breast cancer, cardiovascular diseases such as myocardial infarction and stroke, dermatomyositis, Down's Syndrome, gastrointestinal diseases, glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple myeloma, rheumatoid arthritis, Sjogren syndrome, SpinoCerebellar Ataxia 1, SinoCarebellar Ataxia 7, Whipple's Disease and Wilson's Disease.

DETAILED DESCRIPTION OF THE INVENTION

The following definitions of the general terms used in the present description apply irrespectively of whether the terms in question appear alone or in combination with other groups.

Unless otherwise stated, the following terms used in this Application, including the specification and claims, have the definitions given below. It must be noted that, as used in the specification and the appended claims, the singular forms "a", "an," and "the" include plural referents unless the context clearly dictates otherwise.

"Optional" or "optionally" means that the subsequently described event or circumstance may but need not occur, and that the description includes instances where the event or circumstance occurs and instances in which it does not.

The term "lower alkyl", alone or in combination with other groups, stands for a hydrocarbon radical which may be linear or branched, with single or multiple branching, containing 1 to 6 carbon atoms, for example, methyl (Me), ethyl (Et), propyl, isopropyl (i-propyl), n-butyl, i-butyl (iso-butyl), 2-butyl (sec-butyl), t-butyl (tert-butyl) and the like. Preferred alkyl groups are groups with 1 to 4 carbon atoms. Most preferred is methyl.

The term "cyano-lower alkyl", alone or in combination with other groups, refers to lower alkyl as defined herewithin, which is substituted by one or multiple cyano, preferably 1-5 cyano, more preferably 1 cyano. Examples are cyano-methyl and the like.

The term "halogen-lower alkyl", alone or in combination with other groups, refers to lower alkyl as defined herewithin, which is substituted by one or multiple halogen, preferably 1-5 halogen, more preferably 1-3 halogen, most preferably 1 halogen or 3 halogen. Examples are trifluoromethyl, chloromethyl, fluoromethyl and the like.

The term "cycloalkyl-lower alkyl", alone or in combination with other groups, refers to lower alkyl as defined herewithin, which is substituted by one cycloalkyl as defined herein. Examples are cyclopropylmethyl, cyclopropylethyl and the like.

The term "lower alkoxy-lower alkyl", alone or in combination with other groups, refers to lower alkyl, which is substituted by one or multiple lower alkoxy as defined herewithin. Examples are MeO-Me, 1MeO-Et, 2MeO-Et, 1MeO-2EtO-propyl and the like.

The term "lower alkyl substituted by", alone or in combination with other groups, stands for a lower alkyl as defined herein, which is substituted by one or multiple substituents, preferably 1-5 substituents with a substituent individually selected from the group as specified for each specific "lower alkyl substituted by", e.g. cyano, halogen, hydroxy and lower alkoxy.

The term "lower alkenyl" denotes a monovalent linear or branched hydrocarbon group of 2 to 7 carbon atoms, in particular 2 to 4 carbon atoms, with at least one double bond. Examples of alkenyl include ethenyl, propenyl, prop-2-enyl, isopropenyl, n-butenyl, i-butenyl, and t-butenyl. Particular is ethenyl.

The term "lower alkenyl substituted by", alone or in combination with other groups, stands for a lower alkenyl as defined herein, which is substituted by one or multiple substituents, preferably 1-4 substituents with a substituent individually selected from the group as specified for each specific "lower alkenyl substituted by", e.g. cyano, cyano-lower alkyl, halogen, halogen-lower alkoxy, halogen-lower alkyl, heteroaryl, lower alkoxy, lower alkoxy-lower alkyl and lower alkyl.

The term "cycloalkyl-lower alkenyl", alone or in combination with other groups, refers to lower alkenyl as defined herewithin, which is substituted by one cycloalkyl as defined herein. Examples are cyclopropyl-ethenyl, cyclopropyl-propenyl and the like.

The term "lower alkynyl" denotes a monovalent linear or branched saturated hydrocarbon group of 2 to 7 carbon atoms, in particular from 2 to 4 carbon atoms, containing one, two or three triple bonds. Examples of alkynyl include ethynyl, propynyl, prop-2-ynyl, isopropynyl, n-butynyl and iso-butynyl.

The term "cycloalkyl-lower alkynyl", alone or in combination with other groups, refers to lower alkynyl as defined herewithin, which is substituted by one cycloalkyl as defined herein. Examples are cyclopropyl-ethynyl, cyclopropyl-propynyl and the like.

The term "cyano", alone or in combination with other groups, refers to N≡C—(NC—).

The term "amido", alone or in combination with other groups, refers to —C(═O)—NH$_2$.

The term "nitro", alone or in combination with other groups, refers to —NO$_2$.

The term "hydroxy", alone or in combination with other groups, refers to —OH.

The term "halogen", alone or in combination with other groups, denotes chloro (Cl), iodo (I), fluoro (F) and bromo (Br). Preferred "halogen" is Cl and F.

The term "aryl", alone or in combination with other groups, refers to an aromatic carbocyclic group comprising 6 to 14, preferably 6 to 10, carbon atoms and having at least one aromatic ring or multiple condensed rings in which at least one ring is aromatic. Examples of "aryl" include benzyl, biphenyl, indanyl, naphthyl, phenyl (Ph) and the like. Preferred "aryl" is phenyl.

The phrase "aryl substituted by", alone or in combination with other groups, refers to an aryl which is substituted by one or multiple substituents, preferably 1-4 substituents, whereby substitution at each ring atom individually is possible, with a substituent individually selected from the group as specified for each specific "aryl substituted by", e.g. from cyano, cyano-lower alkyl, halogen, halogen-lower alkoxy, halogen-lower alkyl, lower alkoxy, lower alkoxy-lower alkyl and lower alkyl. Examples are halogen-aryl, chloro-phenyl. fluoro-phenyl, lower alkyl-aryl, methyl-phenyl, lower alkoxy-aryl, methoxy-phenyl and the like.

The term "heteroaryl", alone or in combination with other groups, refers to a cyclic aromatic group of having a single 4 to 8 membered ring or multiple condensed rings comprising 6 to 14, more preferably 6 to 10, ring atoms which containsio 1, 2 or 3 heteroatoms individually selected from N, O and S, in particular N and O, in which group at least one heterocyclic ring is aromatic. Examples of "heteroaryl" include benzofuryl, benzoimidazolyl, benzooxazinyl, benzothiazinyl, benzothiazolyl, benzothienyl, benzotriazolyl, furyl, imidazolyl, indazolyl, indolyl, isoquinolinyl, isothiazolyl, isoxazolyl, oxazolyl, pyrazinyl, pyrazolyl (pyrazyl), pyrazolo[1,5-a]pyridinyl, pyridazinyl, pyridinyl, pyrimidinyl, pyrrolyl, quinolinyl, tetrazolyl, thiazolyl, thienyl, triazolyl and the like. Preferred are 1H-pyrazolyl, furyl, isoxazolyl, oxazolyl, pyrazinyl, pyrazolyl, pyridazinyl, pyridinyl, pyridinyl-N-oxide and pyrimidinyl. More preferred heteroaryls are pyridinyl, pyrazolyl, pyrazinyl and pyrimidinyl. Most preferred are pyridin-2-yl, pyrazin-2-yl, 1H-pyrazol-3-yl and pyrimidin-2-yl.

The phrase "heteroaryl substituted by", alone or in combination with other groups, refers to a heteroaryl which is substituted by one or multiple substituents, preferably 1-4 substituents, whereby substitution at each ring atom individually is possible, the substituent is individually selected from the group as specified for each specific "heteroaryl substituted by", i.e. for example from cyano, cyano-lower alkyl, halogen, halogen-lower alkoxy, halogen-lower alkyl, lower alkoxy, lower alkoxy-lower alkyl and lower alkyl. Preferred "heteroaryl substituted by" are heteroaryl substituted by 1-2 substituents individually selected from cyano, halogen, halogen-lower alkoxy, halogen-lower alkyl and lower alkyl. More preferred are (2,2,2-Trifluoroethoxy)-pyridine-2-yl, 3,5-Dichloro-pyridine-2-yl, 3,5-Difluoro-pyridine-2-yl, 3-Chloro-5-fluoro-pyridine-2-yl, 3-Chloro-5-trifluoromethyl-pyridine-2-yl, 3-Chloro-pyridine-2-yl, 3-Fluoro-pyridine-2-yl, 3-Trifluoromethyl-pyridine-2-yl, 4-Chloro-1-methyl-1H-pyrazol-3-yl, 5-Chloro-3-fluoro-pyridine-2-yl, 5-Chloro-3-methyl-pyridine-2-yl, 5-Chloro-pyridine-2-yl, 5-Chloro-pyrimidine-2-yl, 5-Cyano-pyridine-2-yl, 5-Fluoro-pyridine-2-yl, 5-Trifluoromethyl-pyrazine-2-yl and 5-Trifluoromethyl-pyrimidine-2-yl.

The term "lower alkoxy", alone or in combination with other groups, stands for an —O-lower alkyl radical which may be linear or branched, with single or multiple branching, whereby the alkyl group in general comprises 1 to 6 carbon atoms, for example, methoxy (OMe, MeO), ethoxy (OEt), propoxy, isopropoxy (i-propoxy), n-butoxy, i-butoxy (iso-butoxy), 2-butoxy (sec-butoxy), t-butoxy (tert-butoxy), iso-pentyloxy (i-pentyloxy) and the like. Preferred "lower alkoxy" are groups with 1 to 4 carbon atoms. Most preferred is methoxy.

The term "halogen-lower alkoxy", alone or in combination with other groups, refers to lower alkoxy as defined herewithin, which is substituted by one or multiple halogens. Preferred "halogen-lower alkoxy" are fluoro-lower alkoxy, fluoro-ethoxy and halogen-ethoxy, most preferred is 2,2,2-trifluoro-ethoxy.

The term "cycloalkyl-lower alkoxy", alone or in combination with other groups, refers to lower alkoxy as defined herewithin, which is substituted by one cycloalkyl as defined herein. Examples are cyclopropyl-ethoxy, cyclopropyl-methoxy and the like.

The term "cycloalkyl", alone or in combination with other groups, denotes a monovalent saturated monocyclic or bicyclic hydrocarbon group of 3 to 10 ring carbon atoms, particularly a monovalent saturated monocyclic hydrocarbon group of 3 to 8 ring carbon atoms. Bicyclic means consisting of two saturated carbocycles having two carbon atoms in common, i.e. the bridge separating the two rings is either a single bond or a chain of one or two carbon atoms. Particular cycloalkyl groups are monocyclic. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl, bicyclo[2.2.2]octanyl or adamantanyl. Particular is cyclopropyl.

The phrase "cycloalkyl substituted by", alone or in combination with other groups, refers to a cycloalkyl as defined herein, which is substituted by one or multiple substituents, preferably 1-4 substituents, whereby substitution at each ring atom individually is possible, the substituent is individually selected from the group as specified for each specific "cycloalkyl substituted by", i.e. for example from cyano, cyano-lower alkyl, halogen, halogen-lower alkoxy, halogen-lower alkyl, lower alkoxy, lower alkoxy-lower alkyl and lower alkyl.

The term "pharmaceutically acceptable salts" refers to salts that are suitable for use in contact with the tissues of humans and animals. Examples of suitable salts with inorganic and organic acids are, but are not limited to acetic acid, citric acid, formic acid, fumaric acid, hydrochloric acid, lactic acid, maleic acid, malic acid, methane-sulfonic acid, nitric acid, phosphoric acid, p-toluenesulphonic acid, succinic acid, sulfuric acid, sulphuric acid, tartaric acid, trifluoroacetic acid and the like. Preferred are formic acid, trifluoroacetic acid and hydrochloric acid. Most preferred is hydrochloric acid.

The terms "pharmaceutically acceptable carrier" and "pharmaceutically acceptable auxiliary substance" refer to carriers and auxiliary substances such as diluents or excipients that are compatible with the other ingredients of the formulation.

The term "pharmaceutical composition" encompasses a product comprising specified ingredients in pre-determined amounts or proportions, as well as any product that results, directly or indirectly, from combining specified ingredients in specified amounts. Preferably it encompasses a product comprising one or more active ingredients, and an optional carrier comprising inert ingredients, as well as any product that results, directly or indirectly, from combination, complexation or aggregation of any two or more of the ingredients, or from dissociation of one or more of the ingredients, or from other types of reactions or interactions of one or more of the ingredients.

The term "half maximal inhibitory concentration" ($IC_{50}$) denotes the concentration of a particular compound required for obtaining 50% inhibition of a biological process in vitro. $IC_{50}$ values can be converted logarithmically to $pIC_{50}$ values ($-\log IC_{50}$), in which higher values indicate exponentially greater potency. The $IC_{50}$ value is not an absolute value but depends on experimental conditions e.g. concentrations employed. The $IC_{50}$ value can be converted to an absolute inhibition constant (Ki) using the Cheng-Prusoff equation (Biochem. Pharmacol. (1973) 22:3099). The term "inhibition constant" (Ki) denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values ($-\log$ Ki), in which higher values indicate exponentially greater potency.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

The term "as defined herein" and "as described herein" when referring to a variable incorporates by reference the broad definition of the variable as well as preferred, more preferred and most preferred definitions, if any.

The terms "treating", "contacting" and "reacting" when referring to a chemical reaction means adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

Whenever a chiral carbon is present in a chemical structure, it is intended that all stereoisomers associated with that chiral carbon are encompassed by the structure.

The invention also provides pharmaceutical compositions, methods of using, and methods of preparing the aforementioned compounds.

All separate embodiments can be combined.

One embodiment of the invention is a compound of formula I,

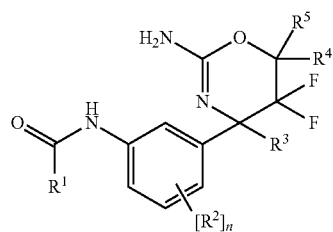

wherein
$R^1$ is selected from the group consisting of
  i) aryl,
  ii) aryl substituted by 1-4 substituents individually selected from cyano, cyano-lower alkyl, halogen, halogen-lower alkoxy, halogen-lower alkyl, lower alkoxy, lower alkoxy-lower alkyl and lower alkyl,
  iii) heteroaryl,
  iv) heteroaryl substituted by 1-4 substituents individually selected from amido, cyano, cyano-lower alkyl, cycloalkyl, cycloalkyl-lower alkenyl, cycloalkyl-lower alkynyl, cycloalkyl-lower alkyl, cycloalkyl-lower alkoxy, halogen, halogen-lower alkoxy, halogen-lower alkyl, lower alkoxy, lower alkoxy-lower alkyl, lower alkenyl, lower alkynyl, lower alkyl and nitro;
  v) lower alkyl,
  vi) lower alkyl substituted by 1-5 substituents individually selected from cyano, halogen, hydroxy and lower alkoxy;
  vii) lower alkenyl,
  viii) lower alkenyl substituted by 1-4 substituents individually selected from cyano, cyano-lower alkyl, halogen, halogen-lower alkoxy, halogen-lower alkyl, heteroaryl, lower alkoxy, lower alkoxy-lower alkyl and lower alkyl,
  ix) cycloalkyl, and
  x) cycloalkyl substituted by 1-4 substituents individually selected from cyano, cyano-lower alkyl, halogen, halogen-lower alkoxy, halogen-lower alkyl, lower alkoxy, lower alkoxy-lower alkyl and lower alkyl,
$R^2$ is selected from the group consisting of
  i) hydrogen,
  ii) halogen, and
  iii) lower alkyl;
$R^3$ is lower alkyl;
$R^4$ is selected from the group consisting of
  i) hydrogen, and
  ii) lower alkyl;
$R^5$ is selected from the group consisting of
  i) hydrogen, and
  ii) lower alkyl; and
n is 0, 1 or 2;
or pharmaceutically acceptable salts thereof.

A certain embodiment of the invention provides a compound of formula I as described herein, wherein
$R^1$ is selected from the group consisting of
  i) heteroaryl,
  ii) heteroaryl substituted by 1-4 substituents individually selected from amido, cyano, cyano-lower alkyl, cycloalkyl, cycloalkyl-lower alkenyl, cycloalkyl-lower alkynyl, cycloalkyl-lower alkyl, cycloalkyl-lower alkoxy, halogen, halogen-lower alkoxy, halogen-lower alkyl, lower alkoxy, lower alkoxy-lower alkyl, lower alkenyl, lower alkynyl, lower alkyl and nitro;
  iii) lower alkyl,
  iv) lower alkyl substituted by 1-5 substituents individually selected from cyano, halogen, hydroxy and lower alkoxy;
  v) lower alkenyl,
  vi) lower alkenyl substituted by 1-4 substituents individually selected from cyano, cyano-lower alkyl, halogen, halogen-lower alkoxy, halogen-lower alkyl, heteroaryl, lower alkoxy, lower alkoxy-lower alkyl and lower alkyl,
  vii) cycloalkyl, and
  viii) cycloalkyl substituted by 1-4 substituents individually selected from cyano, cyano-lower alkyl, halogen, halogen-lower alkoxy, halogen-lower alkyl, lower alkoxy, lower alkoxy-lower alkyl and lower alkyl,
$R^2$ is selected from the group consisting of
  i) hydrogen,
  ii) halogen, and
  iii) lower alkyl;
$R^3$ is lower alkyl;
$R^4$ is selected from the group consisting of
  i) hydrogen, and
  ii) lower alkyl;
$R^5$ is selected from the group consisting of
  i) hydrogen, and
  ii) lower alkyl; and
n is 0, 1 or 2;
or pharmaceutically acceptable salts thereof.

A certain embodiment of the invention provides a compound of formula I as described herein, wherein
$R^1$ is selected from the group consisting of
  i) heteroaryl,
  ii) heteroaryl substituted by 1-4 substituents individually selected from amido, cyano, cyano-lower alkyl, cycloalkyl, cycloalkyl-lower alkenyl, cycloalkyl-lower alkynyl, cycloalkyl-lower alkyl, cycloalkyl-lower alkoxy, halogen, halogen-lower alkoxy, halogen-lower alkyl, lower alkoxy, lower alkoxy-lower alkyl, lower alkenyl, lower alkynyl, lower alkyl and nitro;
  iii) lower alkyl,
  iv) lower alkyl substituted by 1-5 substituents individually selected from cyano, halogen, hydroxy and lower alkoxy;
  v) lower alkenyl,
  vi) lower alkenyl substituted by 1-4 substituents individually selected from cyano, cyano-lower alkyl, halogen, halogen-lower alkoxy, halogen-lower alkyl, heteroaryl, lower alkoxy, lower alkoxy-lower alkyl and lower alkyl, vii) cycloalkyl, and
viii) cycloalkyl substituted by 1-4 substituents individually selected from cyano, cyano-lower alkyl, halogen, halogen-lower alkoxy, halogen-lower alkyl, lower alkoxy, lower alkoxy-lower alkyl and lower alkyl, $R^2$ is selected from the group consisting of
  i) hydrogen,
  ii) halogen, and
  iii) lower alkyl;
$R^3$ is lower alkyl;
$R^4$ is selected from the group consisting of
  i) hydrogen, and
  ii) lower alkyl;
$R^5$ is selected from the group consisting of
  i) hydrogen, and
  ii) lower alkyl; and
n is 0, 1 or 2;
or pharmaceutically acceptable salts thereof.

A certain embodiment of the invention provides a compound of formula Ia as described herein wherein
$R^1$ is selected from the group consisting of
  i) aryl,
  ii) aryl substituted by 1-4 substituents individually selected from cyano, cyano-lower alkyl, halogen, halogen-lower alkoxy, halogen-lower alkyl, lower alkoxy, lower alkoxy-lower alkyl and lower alkyl,
  iii) heteroaryl, and
  iv) heteroaryl substituted by 1-4 substituents individually selected from cyano, cyano-lower alkyl, halogen, halogen-lower alkoxy, halogen-lower alkyl, lower alkoxy, lower alkoxy-lower alkyl and lower alkyl;
$R^2$ is selected from the group consisting of
  i) hydrogen,
  ii) halogen, and
  iii) lower alkyl;
$R^3$ is lower alkyl;
$R^4$ is selected from the group consisting of
  i) hydrogen, and
  ii) lower alkyl; and
$R^5$ is selected from the group consisting of
  i) hydrogen, and
  ii) lower alkyl;
or pharmaceutically acceptable salts thereof.

A certain embodiment of the invention provides a compound of formula Ia as described herein wherein
$R^1$ is selected from the group consisting of
  i) heteroaryl, and
  ii) heteroaryl substituted by 1-4 substituents individually selected from cyano, cyano-lower alkyl, halogen, halogen-lower alkoxy, halogen-lower alkyl, lower alkoxy, lower alkoxy-lower alkyl and lower alkyl;

$R^2$ is selected from the group consisting of
  i) hydrogen,
  ii) halogen, and
  iii) lower alkyl;
$R^3$ is lower alkyl;
$R^4$ is selected from the group consisting of
  i) hydrogen, and
  ii) lower alkyl; and
$R^5$ is selected from the group consisting of
  i) hydrogen, and
  ii) lower alkyl;
or pharmaceutically acceptable salts thereof.

A certain embodiment of the invention provides a compound of formula I as described herein, wherein $R^1$ is selected from the group consisting of
  i) 1H-pyrazolyl, optionally substituted by 1-2 substituents individually selected from cycloalkyl, halogen, halogen-lower alkyl, lower alkyl,
  ii) cycloalkyl, optionally substituted by 1-2 substituents individually selected from halogen and halogen-lower alkyl,
  iii) lower alkenyl, optionally substituted by heteroaryl,
  iv) lower alkyl, optionally substituted by 1-5 substituents individually selected from halogen and hydroxy,
  v) furyl, optionally substituted by nitro,
  vi) isoxazolyl, optionally substituted by 1-2 lower alkyl,
  vii) oxazolyl, optionally substituted by 1-2 substituents individually selected from cycloalkyl, halogen-lower alkyl and lower alkyl,
  viii) pyrazinyl, optionally substituted by 1-2 substituents individually selected from cycloalkyl-lower alkoxy, halogen, halogen-lower alkyl and lower alkyl,
  ix) pyrazolyl, optionally substituted by 1-2 substituents individually selected from halogen and lower alkyl,
  x) pyridazinyl, optionally substituted by 1-2 halogen,
  xi) pyridinyl, optionally substituted by 1-2 substituents individually selected from amido, cyano, cycloalkyl-lower alkoxy, cycloalkyl-lower alkynyl, halogen, halogen-lower alkyl, lower alkyl and halogen-lower alkoxy; and
  xii) pyrimidinyl, optionally substituted by 1-2 substituents individually selected from halogen and halogen-lower alkyl.

A certain embodiment of the invention provides a compound of formula I as described herein, wherein $R^1$ is selected from the group consisting of
  i) pyridinyl,
  ii) pyrazolyl,
  iii) pyrazinyl,
  iv) pyrimidinyl, and
  v) pyridinyl substituted by 1-2 substituents individually selected from cyano, halogen, and halogen-lower alkyl.

A certain embodiment of the invention provides a compound of formula I as described herein, wherein $R^1$ is selected from the group consisting of (2,2,2-trifluoroethoxy)-pyridin-2-yl, (cyclopropylmethoxy)pyrazin-2-yl, (trifluoromethyl) pyrazin-2-yl, 1-(difluoromethyl)-1H-pyrazol-3-yl, 1-(trifluoromethyl)cycloprop-1-yl, 1-furyl-ethenyl, 1-methyl-1H-pyrazol-3-yl, 2-(chloromethyl)oxazol-4-yl, 2-(fluoromethyl)oxazol-4-yl, 2,2,2-trifluoro-1-hydroxy-1-methyl-2-ethyl, 2,2-difluorocycloprop-1-yl, 2,5-dimethyloxazol-4-yl, 2-ethyloxazol-4-yl, 2-methyl-5-(trifluoromethyl)oxazol-4-yl, 2-methyloxazol-4-yl, 3-(2,2,2-trifluoroethoxy)-pyridin-2-yl, 3,5-dichloropyrazin-2-yl, 3,5-dichloro-pyridin-2-yl, 3,5-difluoro-pyridin-2-yl, 3-chloro-5-cyano-pyridin-2-yl, 3-chloro-5-fluoro-pyridin-2-yl, 3-chloro-5-trifluoromethyl-pyridin-2-yl, 3-chloro-pyridin-2-yl, 3-fluoro-pyridin-2-yl, 3-trifluoromethyl-pyridin-2-yl, 4-chloro-1-(2,2,2-trifluoroethyl)-1H-pyrazol-3-yl, 4-chloro-1-(2,2-difluoroethyl)-1H- pyrazol-3-yl, 4-chloro-1-difluoromethyl-1H-pyrazol-3-yl, 4-chloro-1-ethyl-1H-pyrazole-3-yl, 4-chloro-1H-pyrazol-5-yl, 4-chloro-1-methyl-1H-pyrazol-3-yl, 4-chloro-3-cyclopropyl-1H-pyrazol-5-yl, 4-methyl-1H-pyrazol-5-yl, 4-methyl-isoxazol-3-yl, 5-(2,2,2-trifluoro-ethoxy)-pyridin-2-yl, 5-(2,2,3,3,3-pentafluoropropoxy)-pyridin-2-yl, 5-(2,2,3,3-tetrafluoropropoxy)-pyridin-2-yl, 5-(2,2-difluoroethoxy)-pyridin-2-yl, 5-(cyclopropylethynyl)-pyridin-2-yl, 5-(cyclopropylmethoxy)pyrazin-2-yl, 5-(difluoromethoxy)-pyridin-2-yl, 5-(fluoromethoxy)-pyridin-2-yl, 5-(trifluoromethyl)-pyridin-2-yl, 5-amido-pyridin-2-yl, 5-chloro-3-fluoro-pyridine-2-yl, 5-chloro-3-methyl-pyridin-2-yl, 5-chloropyrazin-2-yl, 5-chloro-pyridin-2-yl, 5-chloro-pyrimidin-2-yl, 5-cyano-pyridin-1-oxide-2-yl, 5-cyano-pyridin-2-yl, 5-cyclopropyl-oxazol-4-yl, 5-ethyl-oxazol-4-yl, 5-fluoromethoxy-pyridin-2-yl, 5-fluoro-pyridin-2-yl, 5-isopropyl-oxazol-4-yl, 5-methyl-pyrazin-2-yl, 5-nitro-fur-2-yl, 5-trifluoromethyl-pyrazin-2-yl, 5-trifluoromethyl-pyrimidin-2-yl, 6-(cyclopropylmethoxy)-pyridin-3-yl, 6-chloropyridazin-3-yl, fur-2-yl, methyl, oxazolyl and pyridin-2-yl.

A certain embodiment of the invention provides a compound of formula I as described herein, wherein $R^1$ is selected from the group consisting of 5-Chloro-pyridine-2-yl, 3-Chloro-5-trifluoromethyl-pyridine-2-yl, 3-Chloro-5-fluoro-pyridine-2-yl, 3,5-Dichloro-pyridine-2-yl, 5-Cyano-pyridine-2-yl, 5-Chloro-3-fluoro-pyridine-2-yl, 5-Chloro-pyridine-2-yl and 3-Chloro-5-trifluoromethyl-pyridine-2-yl.

A certain embodiment of the invention provides a compound of formula I as described herein, wherein $R^1$ is 1H-pyrazolyl, optionally substituted by 1-2 substituents individually selected from cycloalkyl, halogen, halogen-lower alkyl, and lower alkyl.

A certain embodiment of the invention provides a compound of formula I as described herein, wherein $R^1$ is 1H-pyrazolyl, in particular 1H-pyrazol-3-yl and 1H-pyrazol-5-yl.

A certain embodiment of the invention provides a compound of formula I as described herein, wherein $R^1$ is 1H-pyrazolyl substituted by difluoromethyl, in particular 1-(difluoromethyl)-1H-pyrazol-3-yl.

A certain embodiment of the invention provides a compound of formula I as described herein, wherein $R^1$ is 1H-pyrazolyl substituted by methyl, in particular 1-methyl-1H-pyrazol-3-yl and 4-methyl-1H-pyrazol-5-yl.

A certain embodiment of the invention provides a compound of formula I as described herein, wherein $R^1$ is 1H-pyrazolyl substituted by chloro, in particular 4-chloro-1H-pyrazol-5-yl.

A certain embodiment of the invention provides a compound of formula I as described herein, wherein $R^1$ is 1H-pyrazolyl substituted by chloro and cycloalkyl, in particular 4-chloro-3-cyclopropyl-1H-pyrazol-5-yl.

A certain embodiment of the invention provides a compound of formula I as described herein, wherein $R^1$ is 1H-pyrazolyl substituted by chloro and difluoroethyl, in particular 4-chloro-1-(2,2-difluoroethyl)-1H-pyrazol-3-yl.

A certain embodiment of the invention provides a compound of formula I as described herein, wherein $R^1$ is 1H-pyrazolyl substituted by chloro and difluoromethyl, in particular 4-chloro-1-(difluoromethyl)-1H-pyrazol-3-yl.

A certain embodiment of the invention provides a compound of formula I as described herein, wherein $R^1$ is 1H-pyrazolyl substituted by chloro and trifluoroethyl, in particular 4-chloro-1-(2,2,2-trifluoroethyl)-1H-pyrazol-3-yl.

A certain embodiment of the invention provides a compound of formula I as described herein, wherein $R^1$ is cycloalkyl, optionally substituted by 1-2 substituents individually selected from halogen and halogen-lower alkyl.

A certain embodiment of the invention provides a compound of formula I as described herein, wherein $R^1$ is cycloalkyl, in particular cyclopropyl.

A certain embodiment of the invention provides a compound of formula I as described herein, wherein $R^1$ is cycloalkyl substituted by fluoro, in particular 2,2-difluorocycloprop-1-yl.

A certain embodiment of the invention provides a compound of formula I as described herein, wherein $R^1$ is cycloalkyl substituted by trifluoromethyl, in particular 1-(trifluoromethyl)cycloprop-1-yl.

A certain embodiment of the invention provides a compound of formula I as described herein, wherein $R^1$ is lower alkenyl, optionally substituted by heteroaryl.

A certain embodiment of the invention provides a compound of formula I as described herein, wherein $R^1$ is lower alkenyl, in particular ethenyl.

A certain embodiment of the invention provides a compound of formula I as described herein, wherein $R^1$ is lower alkenyl substituted by heteroaryl, in particular 1-furyl-ethenyl.

A certain embodiment of the invention provides a compound of formula I as described herein, wherein $R^1$ is lower alkyl, optionally substituted by 1-5 substituents individually selected from halogen and hydroxy.

A certain embodiment of the invention provides a compound of formula I as described herein, wherein $R^1$ is lower alkyl, in particular methyl and isopropyl.

A certain embodiment of the invention provides a compound of formula I as described herein, wherein $R^1$ is lower alkyl substituted by fluoro and hydroxy, in particular 2,2,2-trifluoro-1-hydroxy-1-methyl-2-ethyl.

A certain embodiment of the invention provides a compound of formula I as described herein, wherein $R^1$ is furyl, optionally substituted by nitro.

A certain embodiment of the invention provides a compound of formula I as described herein, wherein $R^1$ is furyl, in particular fur-2-yl.

A certain embodiment of the invention provides a compound of formula I as described herein, wherein $R^1$ is furyl substituted by nitro, in particular 5-nitro-fur-2-yl.

A certain embodiment of the invention provides a compound of formula I as described herein, wherein $R^1$ is isoxazolyl, optionally substituted by 1-2 lower alkyl.

A certain embodiment of the invention provides a compound of formula I as described herein, wherein $R^1$ is isoxazolyl, in particular isoxazol-3-yl.

A certain embodiment of the invention provides a compound of formula I as described herein, wherein $R^1$ is isoxazolyl substituted by lower alkyl, in particular 4-methylisoxazol-3-yl.

A certain embodiment of the invention provides a compound of formula I as described herein, wherein $R^1$ is oxazolyl, optionally substituted by 1-2 substituents individually selected from cycloalkyl, halogen-lower alkyl and lower alkyl.

A certain embodiment of the invention provides a compound of formula I as described herein, wherein $R^1$ is oxazolyl, in particular oxazol-4-yl.

A certain embodiment of the invention provides a compound of formula I as described herein, wherein $R^1$ is oxazolyl substituted by lower alkyl, in particular 2-ethyl-oxazol-4-yl, 5-ethyl-oxazol-4-yl, 5-isopropyl-oxazol-4-yl, 2,5-dimethyl-oxazol-4-yl and 2-methyl-oxazol-4-yl.

A certain embodiment of the invention provides a compound of formula I as described herein, wherein $R^1$ is oxazolyl substituted by halogen-lower alkyl, in particular 2-(chloromethyl)oxazol-4-yl and 2-(fluoromethyl)oxazol-4-yl.

A certain embodiment of the invention provides a compound of formula I as described herein, wherein $R^1$ is oxazolyl substituted by halogen-lower alkyl and lower alkyl, in particular 2-methyl-5-(trifluoromethyl)oxazol-4-yl.

A certain embodiment of the invention provides a compound of formula I as described herein, wherein $R^1$ is oxazolyl substituted by cycloalkyl, in particular 5-cyclopropyl-oxazol-4-yl.

A certain embodiment of the invention provides a compound of formula I as described herein, wherein $R^1$ is pyrazinyl, optionally substituted by 1-2 substituents individually selected from cycloalkyl-lower alkoxy, halogen, halogen-lower alkyl and lower alkyl.

A certain embodiment of the invention provides a compound of formula I as described herein, wherein $R^1$ is pyrazinyl, in particular pyrazin-2-yl.

A certain embodiment of the invention provides a compound of formula I as described herein, wherein $R^1$ is pyrazinyl substituted by halogen, in particular 5-chloro-pyrazin-2-yl and 3,5-dichloro-pyrazin-2-yl.

A certain embodiment of the invention provides a compound of formula I as described herein, wherein $R^1$ is pyrazinyl substituted by halogen-lower alkyl, in particular 5-trifluoromethyl-pyrazine-2-yl.

A certain embodiment of the invention provides a compound of formula I as described herein, wherein $R^1$ is pyrazinyl substituted by lower alkyl, in particular 5-methyl-pyrazin-2-yl.

A certain embodiment of the invention provides a compound of formula I as described herein, wherein $R^1$ is pyrazinyl substituted by cycloalkyl-lower alkoxy, in particular 5-(cyclopropylmethoxy)pyrazin-2-yl.

A certain embodiment of the invention provides a compound of formula I as described herein, wherein $R^1$ is pyrazolyl, optionally substituted by 1-2 substituents individually selected from halogen and lower alkyl.

A certain embodiment of the invention provides a compound of formula I as described herein, wherein $R^1$ is pyrazolyl, in particular pyrazol-3-yl.

A certain embodiment of the invention provides a compound of formula I as described herein, wherein $R^1$ is pyrazolyl substituted by halogen and lower alkyl, in particular 4-chloro-1-methyl-1H-pyrazol-3-yl.

A certain embodiment of the invention provides a compound of formula I as described herein, wherein $R^1$ is pyridazinyl, optionally substituted by 1-2 halogen.

A certain embodiment of the invention provides a compound of formula I as described herein, wherein $R^1$ is pyridazinyl, in particular pyridazin-3-yl.

A certain embodiment of the invention provides a compound of formula I as described herein, wherein $R^1$ is pyridazinyl substituted by halogen, in particular 6-chloro-pyridazin-3-yl.

A certain embodiment of the invention provides a compound of formula I as described herein, wherein $R^1$ is pyridinyl, optionally substituted by 1-2 substituents individually selected from amido, cyano, cycloalkyl-lower alkoxy, cycloalkyl-lower alkynyl, halogen, halogen-lower alkyl, lower alkyl and halogen-lower alkoxy.

A certain embodiment of the invention provides a compound of formula I as described herein, wherein $R^1$ is pyridinyl, in particular pyridine-2-yl.

A certain embodiment of the invention provides a compound of formula I as described herein, wherein $R^1$ is pyridinyl substituted by amido, in particular 5-amido-pyridin-2-yl.

A certain embodiment of the invention provides a compound of formula I as described herein, wherein $R^1$ is pyridinyl substituted by cyano, in particular 5-cyano-pyridin-2-yl.

A certain embodiment of the invention provides a compound of formula I as described herein, wherein $R^1$ is the N-oxide of pyridinyl substituted by cyano, in particular 5-cyano-pyridin-1-oxide-2-yl.

A certain embodiment of the invention provides a compound of formula I as described herein, wherein $R^1$ is pyridinyl substituted by halogen.

A certain embodiment of the invention provides a compound of formula I as described herein, wherein $R^1$ is pyridinyl substituted by chloro, in particular 5-chloro-pyridin-2-yl, 3,5-dichloro-pyridin-2-yl and 3-chloro-pyridin-2-yl.

A certain embodiment of the invention provides a compound of formula I as described herein, wherein $R^1$ is pyridinyl substituted by fluoro, in particular 5-fluoro-pyridin-2-yl, 3,5-difluoro-pyridin-2-yl and 3-fluoro-pyridin-2-yl.

A certain embodiment of the invention provides a compound of formula I as described herein, wherein $R^1$ is pyridinyl substituted by halogen and halogen-lower alkyl, in particular 3-chloro-5-trifluoromethyl-pyridin-2-yl.

A certain embodiment of the invention provides a compound of formula I as described herein, wherein $R^1$ is pyridinyl substituted by halogen and cyano, in particular 3-chloro-5-cyano-pyridin-2-yl.

A certain embodiment of the invention provides a compound of formula I as described herein, wherein $R^1$ is pyridinyl substituted by halogen and lower alkyl, in particular 5-chloro-3-methyl-pyridin-2-yl.

A certain embodiment of the invention provides a compound of formula I as described herein, wherein $R^1$ is pyridinyl substituted by halogen-lower alkoxy.

A certain embodiment of the invention provides a compound of formula I as described herein, wherein $R^1$ is pyridinyl substituted by trifluoroethoxy, in particular 3-(2,2,2-trifluoroethoxy)-pyridin-2-yl and 5-(2,2,2-trifluoroethoxy)-pyridin-2-yl.

A certain embodiment of the invention provides a compound of formula I as described herein, wherein $R^1$ is pyridinyl substituted by difluoroethoxy, in particular 5-(2,2-difluoroethoxy)-pyridin-2-yl.

A certain embodiment of the invention provides a compound of formula I as described herein, wherein $R^1$ is pyridinyl substituted by tetrafluoropropoxy, in particular 5-(2,2,3,3-tetrafluoro-propoxy)-pyridin-2-yl.

A certain embodiment of the invention provides a compound of formula I as described herein, wherein $R^1$ is pyridinyl substituted by pentafluoropropoxy, in particular 5-(2,2,3,3,3-pentafluoro-propoxy)-pyridin-2-yl.

A certain embodiment of the invention provides a compound of formula I as described herein, wherein $R^1$ is pyridinyl substituted by difluoromethoxy, in particular 5-(difluoromethoxy)-pyridin-2-yl.

A certain embodiment of the invention provides a compound of formula I as described herein, wherein $R^1$ is pyridinyl substituted by fluoromethoxy, in particular 5-(fluoromethoxy)-pyridin-2-yl.

A certain embodiment of the invention provides a compound of formula I as described herein, wherein $R^1$ is pyridinyl substituted by cycloalkyl-lower alkoxy, in particular 6-(cyclopropylmethoxy)-pyridin-3-yl.

A certain embodiment of the invention provides a compound of formula I as described herein, wherein $R^1$ is pyridinyl substituted by halogen-lower alkyl, in particular 3-trifluoromethyl-pyridin-2-yl and 5-trifluoromethyl-pyridin-2-yl.

A certain embodiment of the invention provides a compound of formula I as described herein, wherein $R^1$ is pyrimidinyl, optionally substituted by 1-2 substituents individually selected from halogen and halogen-lower alkyl.

A certain embodiment of the invention provides a compound of formula I as described herein, wherein $R^1$ is pyrimidinyl, in particular pyrimidin-2-yl.

A certain embodiment of the invention provides a compound of formula I as described herein, wherein $R^1$ is pyrimidinyl substituted by halogen, in particular 5-chloro-pyrimidin-2-yl.

A certain embodiment of the invention provides a compound of formula I as described herein, wherein $R^1$ is pyrimidinyl substituted by halogen-lower alkyl, in particular 5-trifluoromethyl-pyrimidin-2-yl.

A certain embodiment of the invention provides a compound of formula I as described herein, wherein n is 1.

A certain embodiment of the invention provides a compound of formula I as described herein, wherein n is 0.

A certain embodiment of the invention provides a compound of formula I as described herein, wherein n is 2.

A certain embodiment of the invention provides a compound of formula I as described herein, wherein $R^2$ is hydrogen.

A certain embodiment of the invention provides a compound of formula I as described herein, wherein $R^2$ is halogen.

A certain embodiment of the invention provides a compound of formula I as described herein, wherein $R^2$ is fluoro.

A certain embodiment of the invention provides a compound of formula I as described herein, wherein $R^2$ is chloro.

A certain embodiment of the invention provides a compound of formula I as described herein, wherein $R^3$ is lower alkyl.

A certain embodiment of the invention provides a compound of formula I as described herein, wherein $R^3$ is methyl.

A certain embodiment of the invention provides a compound of formula I as described herein, wherein $R^4$ is hydrogen.

A certain embodiment of the invention provides a compound of formula I as described herein, wherein $R^4$ is lower alkyl.

A certain embodiment of the invention provides a compound of formula I as described herein, wherein $R^4$ is methyl.

A certain embodiment of the invention provides a compound of formula I as described herein, wherein $R^5$ is hydrogen.

A certain embodiment of the invention provides a compound of formula I as described herein, wherein $R^5$ is lower alkyl.

A certain embodiment of the invention provides a compound of formula I as described herein, wherein $R^5$ is methyl.

A certain embodiment of the invention provides a compound of formula I as described herein, selected from the group consisting of 5-Chloro-pyridine-2-carboxylic acid [3-((R)-2-amino-5,5-difluoro-4-methyl-5,6-dihydro-4H-[1,3]oxazin-4-yl)-4-fluoro-phenyl]-amide, 5-Fluoro-pyridine-2-carboxylic acid [3-((R)-2-amino-5,5-difluoro-4-methyl-5,6-dihydro-4H-[1,3]oxazin-4-yl)-4-fluoro-phenyl]-amide, 3-Chloro-pyridine-2-carboxylic acid [3-((R)-2-amino-5,5-difluoro-4-methyl-5,6-dihydro-4H-[1,3]oxazin-4-yl)-4-fluoro-phenyl]-amide, 3,5-Difluoro-pyridine-2-carboxylic acid [3-((R)-2-amino-5,5-difluoro-4-methyl-5,6-dihydro-4H-[1,3]oxazin-4-yl)-4-fluoro-phenyl]-amide, 3-Chloro-5-trifluoromethyl-pyridine-2-carboxylic acid [3-((R)-2-amino-5,5-difluoro-4-methyl-5,6-dihydro-4H-[1,3]oxazin-4-yl)-4-fluoro-phenyl]-amide, 3-Trifluoromethyl-pyridine-2-carboxylic acid [3-((R)-2-amino-5,5-difluoro-4-methyl-5,6-dihydro-4H-[1,3]oxazin-4-yl)-4-fluoro-phenyl]-amide, 3-Chloro-5-fluoro-pyridine-2-carboxylic acid [3-((R)-2-amino-5,5-difluoro-4-methyl-5,6-dihydro-4H-[1,3]oxazin-4-yl)-4-fluoro-phenyl]-amide, 3,5-Dichloro-pyridine-2-carboxylic acid [3-((R)-2-amino-5,5-difluoro-4-methyl-5,6-dihydro-4H-[1,3]oxazin-4-yl)-4-fluoro-phenyl]-amide, Pyridine-2-carboxylic acid [3-((R)-2-amino-5,5-difluoro-4-methyl-5,6-dihydro-4H-[1,3]oxazin-4-yl)-4-fluoro-phenyl]-amide, 3-Fluoro-pyridine-2-carboxylic acid [3-((R)-2-amino-5,5-difluoro-4-methyl-5,6-dihydro-4H-[1,3]oxazin-4-yl)-4-fluoro-phenyl]-amide, 5-Cyano-pyridine-2-carboxylic acid [3-((R)-2-amino-5,5-difluoro-4-methyl-5,6-dihydro-4H-[1,3]oxazin-4-yl)-4-fluoro-phenyl]-amide, 5-Cyano-pyridine-2-carboxylic acid [3-((R)-2-amino-5,5-difluoro-4-methyl-5,6-dihydro-4H-[1,3]oxazin-4-yl)-4-fluoro-phenyl]-amide hydrochloride, 5-Cyano-pyridine-2-carboxylic acid [3-((R)-2-amino-5,5-difluoro-4-methyl-5,6-dihydro-4H-[1,3]oxazin-4-yl)-4-fluoro-phenyl]-amide, 5-Chloro-pyrimidine-2-carboxylic acid [3-((R)-2-amino-5,5-difluoro-4-methyl-5,6-dihydro-4H-[1,3]oxazin-4-yl)-4-fluoro-phenyl]-amide, 5-Chloro-3-methyl-pyridine-2-carboxylic acid [3-((R)-2-amino-5,5-difluoro-4-methyl-5,6-dihydro-4H-[1,3]oxazin-4-yl)-4-fluoro-phenyl]-amide, 5-(2,2,2-Trifluoro-ethoxy)-pyridine-2-carboxylic acid [3-((R)-2-amino-5,5-difluoro-4-methyl-5,6-dihydro-4H-[1,3]oxazin-4-yl)-4-fluoro-phenyl]-amide, 5-Chloro-3-fluoro-pyridine-2-carboxylic acid [3-((R)-2-amino-5,5-difluoro-4-methyl-5,6-dihydro-4H-[1,3]oxazin-4-yl)-4-fluoro-phenyl]-amide, 5-Trifluoromethyl-pyrimidine-2-carboxylic acid [3-((R)-2-amino-5,5-difluoro-4-methyl-5,6-dihydro-4H-[1,3]oxazin-4-yl)-4-fluoro-phenyl]-amide, 5-Trifluoromethyl-pyrazine-2-carboxylic acid [3-((R)-2-amino-5,5-difluoro-4-methyl-5,6-dihydro-4H-[1,3]oxazin-4-yl)-4-fluoro-phenyl]-amide, 4-Chloro-1-methyl-1H-pyrazole-3-carboxylic acid [3-((R)-2-amino-5,5-difluoro-4-methyl-5,6-dihydro-4H-[1,3]oxazin-4-yl)-4-fluoro-phenyl]-amide, 5-Chloro-pyridine-2-carboxylic acid [3-((R)-2-amino-5,5-difluoro-4,6,6-trimethyl-5,6-dihydro-4H-[1,3]oxazin-4-yl)-4-fluoro-phenyl]-amide, 3-Chloro-5-trifluoromethyl-pyridine-2-carboxylic acid [3-((R)-2-amino-5,5-difluoro-4,6,6-trimethyl-5,6-dihydro-4H-[1,3]oxazin-4-yl)-4-fluoro-phenyl]-amide, 5-Cyano-pyridine-2-carboxylic acid [3-((R)-2-amino-5,5-difluoro-4,6,6-trimethyl-5,6-dihydro-4H-[1,3]oxazin-4-yl)-4-fluoro-phenyl]-amide, (R)—N-(3-(2-amino-5,5-difluoro-4,6,6-trimethyl-5,6-dihydro-4H-1,3-oxazin-4-yl)-4-fluorophenyl)-3-chloro-5-cyanopicolinamide hydrochloride, (R)—N-(3-(2-amino-5,5-difluoro-4,6,6-trimethyl-5,6-dihydro-4H-1,3-oxazin-4-yl)-4-fluorophenyl)-3-chloro-5-cyanopicolinamide,

- (R)—N-(3-(2-amino-5,5-difluoro-4,6,6-trimethyl-5,6-dihydro-4H-1,3-oxazin-4-yl)-4-fluorophenyl)-3,5-dichloropicolinamide hydrochloride,
- (R)—N-(3-(2-amino-5,5-difluoro-4,6,6-trimethyl-5,6-dihydro-4H-1,3-oxazin-4-yl)-4-fluorophenyl)-3,5-dichloropicolinamide,
- (R)—N-(3-(2-amino-5,5-difluoro-4,6,6-trimethyl-5,6-dihydro-4H-1,3-oxazin-4-yl)-4-fluorophenyl)-5-chloro-3-fluoropicolinamide,
- (R)—N-(3-(2-amino-5,5-difluoro-4,6,6-trimethyl-5,6-dihydro-4H-1,3-oxazin-4-yl)-4-fluorophenyl)-5-(trifluoromethyl)picolinamide,
- (R)—N-(3-(2-amino-5,5-difluoro-4,6,6-trimethyl-5,6-dihydro-4H-1,3-oxazin-4-yl)-4-fluorophenyl)-5-(fluoromethoxy)picolinamide,
- (R)—N-(3-(2-amino-5,5-difluoro-4,6,6-trimethyl-5,6-dihydro-4H-1,3-oxazin-4-yl)-4-fluorophenyl)-5-(difluoromethoxy)picolinamide,
- (R)—N-(3-(2-amino-5,5-difluoro-4,6,6-trimethyl-5,6-dihydro-4H-1,3-oxazin-4-yl)-4-fluorophenyl)-5-(2,2-difluoroethoxy)picolinamide,
- 5-(2,2,2-Trifluoro-ethoxy)-pyridine-2-carboxylic acid [3-((R)-2-amino-5,5-difluoro-4,6,6-trimethyl-5,6-dihydro-4H-[1,3]oxazin-4-yl)-4-fluoro-phenyl]-amide,
- 5-(2,2,3,3-Tetrafluoro-propoxy)-pyridine-2-carboxylic acid [3-((R)-2-amino-5,5-difluoro-4,6,6-trimethyl-5,6-dihydro-4H-[1,3]oxazin-4-yl)-4-fluoro-phenyl]-amide hydrochloride,
- 5-(2,2,3,3-Tetrafluoro-propoxy)-pyridine-2-carboxylic acid [3-((R)-2-amino-5,5-difluoro-4,6,6-trimethyl-5,6-dihydro-4H-[1,3]oxazin-4-yl)-4-fluoro-phenyl]-amide,
- (R)—N-(3-(2-amino-5,5-difluoro-4,6,6-trimethyl-5,6-dihydro-4H-1,3-oxazin-4-yl)-4-fluorophenyl)-6-(cyclopropylmethoxy)nicotinamide,
- (R)—N-(3-(2-amino-5,5-difluoro-4,6,6-trimethyl-5,6-dihydro-4H-1,3-oxazin-4-yl)-4-fluorophenyl)-5-chloropyrimidine-2-carboxamide,
- 5-Trifluoromethyl-pyrimidine-2-carboxylic acid [3-((R)-2-amino-5,5-difluoro-4,6,6-trimethyl-5,6-dihydro-4H-[1,3]oxazin-4-yl)-4-fluoro-phenyl]-amide,
- (R)—N-(3-(2-amino-5,5-difluoro-4,6,6-trimethyl-5,6-dihydro-4H-1,3-oxazin-4-yl)-4-fluorophenyl)-5-methylpyrazine-2-carboxamide,
- (R)—N-(3-(2-amino-5,5-difluoro-4,6,6-trimethyl-5,6-dihydro-4H-1,3-oxazin-4-yl)-4-fluorophenyl)-5-(trifluoromethyl)pyrazine-2-carboxamide,
- (R)—N-(3-(2-amino-5,5-difluoro-4,6,6-trimethyl-5,6-dihydro-4H-1,3-oxazin-4-yl)-4-fluorophenyl)-5-(cyclopropylmethoxy)pyrazine-2-carboxamide,
- (R)—N-(3-(2-amino-5,5-difluoro-4,6,6-trimethyl-5,6-dihydro-4H-1,3-oxazin-4-yl)-4-fluorophenyl)-6-chloropyridazine-3-carboxamide hydrochloride,
- (R)—N-(3-(2-amino-5,5-difluoro-4,6,6-trimethyl-5,6-dihydro-4H-1,3-oxazin-4-yl)-4-fluorophenyl)-6-chloropyridazine-3-carboxamide,
- (R)—N-(3-(2-amino-5,5-difluoro-4,6,6-trimethyl-5,6-dihydro-4H-1,3-oxazin-4-yl)-4-fluorophenyl)-1-(difluoromethyl)-1H-pyrazole-3-carboxamide,
- 3-Chloro-5-cyano-pyridine-2-carboxylic acid [3-((R)-2-amino-5,5-difluoro-4-methyl-5,6-dihydro-4H-[1,3]oxazin-4-yl)-4-fluoro-phenyl]-amide,
- (S)—N-(3-(2-amino-5,5-difluoro-4-methyl-5,6-dihydro-4H-1,3-oxazin-4-yl)-4-fluorophenyl)-5-(cyclopropylethynyl)picolinamide,
- (R)—N-(3-(2-amino-5,5-difluoro-4-methyl-5,6-dihydro-4H-1,3-oxazin-4-yl)-4-fluorophenyl)-5-(difluoromethoxy)picolinamide,
- (R)—N-(3-(2-amino-5,5-difluoro-4-methyl-5,6-dihydro-4H-1,3-oxazin-4-yl)-4-fluorophenyl)-5-(fluoromethoxy)picolinamide,
- (R)—N-(3-(2-amino-5,5-difluoro-4-methyl-5,6-dihydro-4H-1,3-oxazin-4-yl)-4-fluorophenyl)-5-(2,2,3,3-tetrafluoropropoxy)picolinamide,
- (R)—N-(3-(2-amino-5,5-difluoro-4-methyl-5,6-dihydro-4H-1,3-oxazin-4-yl)-4-fluorophenyl)-5-(2,2,3,3,3-pentafluoropropoxy)picolinamide,
- (R)—N-(3-(2-amino-5,5-difluoro-4-methyl-5,6-dihydro-4H-1,3-oxazin-4-yl)-4-fluorophenyl)-5-(2,2-difluoroethoxy)picolinamide,
- (S)—N-(3-(2-amino-5,5-difluoro-4-methyl-5,6-dihydro-4H-1,3-oxazin-4-yl)-4-fluorophenyl)-5-(cyclopropylmethoxy)pyrazine-2-carboxamide,
- (R)—N-(3-(2-amino-5,5-difluoro-4-methyl-5,6-dihydro-4H-1,3-oxazin-4-yl)-4-fluorophenyl)-5-chloropyrazine-2-carboxamide,
- (R)—N-(3-(2-amino-5,5-difluoro-4-methyl-5,6-dihydro-4H-1,3-oxazin-4-yl)-4-fluorophenyl)-3,5-dichloropyrazine-2-carboxamide,
- (R)—N-(3-(2-amino-5,5-difluoro-4-methyl-5,6-dihydro-4H-1,3-oxazin-4-yl)-4,5-difluorophenyl)-5-cyanopicolinamide,
- (R)—N-(3-(2-amino-5,5-difluoro-4-methyl-5,6-dihydro-4H-1,3-oxazin-4-yl)-4-chlorophenyl)-5-chloropicolinamide,
- (R)—N-(3-(2-amino-5,5-difluoro-4-methyl-5,6-dihydro-4H-1,3-oxazin-4-yl)-4-chlorophenyl)-5-cyanopicolinamide,
- (R)—N-(3-(2-amino-5,5-difluoro-4-methyl-5,6-dihydro-4H-1,3-oxazin-4-yl)phenyl)-5-chloropicolinamide,
- (R)—N-(3-(2-amino-5,5-difluoro-4-methyl-5,6-dihydro-4H-1,3-oxazin-4-yl)phenyl)-5-cyanopicolinamide,
- (R)—N-(3-(2-amino-5,5-difluoro-4-methyl-5,6-dihydro-4H-1,3-oxazin-4-yl)-4-fluorophenyl)-3-(2,2,2-trifluoroethoxy)picolinamide,
- (R)—N-(3-(2-amino-5,5-difluoro-4-methyl-5,6-dihydro-4H-1,3-oxazin-4-yl)-4-fluorophenyl)oxazole-4-carboxamide,
- (R)—N-(3-(2-amino-5,5-difluoro-4-methyl-5,6-dihydro-4H-1,3-oxazin-4-yl)-4-fluorophenyl)-2-ethyloxazole-4-carboxamide,
- (R)—N-(3-(2-amino-5,5-difluoro-4-methyl-5,6-dihydro-4H-1,3-oxazin-4-yl)-4-fluorophenyl)-2-(chloromethyl)oxazole-4-carboxamide,
- (R)—N-(3-(2-amino-5,5-difluoro-4-methyl-5,6-dihydro-4H-1,3-oxazin-4-yl)-4-fluorophenyl)-2-methyloxazole-4-carboxamide,
- (R)—N-(3-(2-amino-5,5-difluoro-4-methyl-5,6-dihydro-4H-1,3-oxazin-4-yl)-4-fluorophenyl)-2,5-dimethyloxazole-4-carboxamide,
- (R)—N-(3-(2-amino-5,5-difluoro-4-methyl-5,6-dihydro-4H-1,3-oxazin-4-yl)-4-fluorophenyl)-2-methyl-5-(trifluoromethyl)oxazole-4-carboxamide,
- (R)—N-(3-(2-amino-5,5-difluoro-4-methyl-5,6-dihydro-4H-1,3-oxazin-4-yl)-4-fluorophenyl)-4-methylisoxazole-3-carboxamide,
- (R)—N-(3-(2-amino-5,5-difluoro-4-methyl-5,6-dihydro-4H-1,3-oxazin-4-yl)-4-fluorophenyl)-5-isopropyloxazole-4-carboxamide,
- (R)—N-(3-(2-amino-5,5-difluoro-4-methyl-5,6-dihydro-4H-1,3-oxazin-4-yl)-4-fluorophenyl)-1-methyl-1H-pyrazole-3-carboxamide,
- (R)—N-(3-(2-amino-5,5-difluoro-4-methyl-5,6-dihydro-4H-1,3-oxazin-4-yl)-4-fluorophenyl)-1-(difluoromethyl)-1H-pyrazole-3-carboxamide, (R)—N-(3-(2-amino-5,5-difluoro-4-methyl-5,6-dihydro-4H-1,3-oxazin-4-yl)-4-fluorophenyl)-4-chloro-1H-pyrazole-5-carboxamide,
(R)—N-(3-(2-amino-5,5-difluoro-4-methyl-5,6-dihydro-4H-1,3-oxazin-4-yl)-4-fluorophenyl)-4-methyl-1H-pyrazole-5-carboxamide,
(R)—N-(3-(2-amino-5,5-difluoro-4-methyl-5,6-dihydro-4H-1,3-oxazin-4-yl)-4-fluorophenyl)-4-chloro-3-cyclopropyl-1H-pyrazole-5-carboxamide,
(R)—N-(3-(2-amino-5,5-difluoro-4-methyl-5,6-dihydro-4H-1,3-oxazin-4-yl)-4-fluorophenyl)-4-chloro-1-(2,2-difluoroethyl)-1H-pyrazole-3-carboxamide,
(R)—N-(3-(2-amino-5,5-difluoro-4-methyl-5,6-dihydro-4H-1,3-oxazin-4-yl)-4-fluorophenyl)-5-ethyloxazole-4-carboxamide formate,
(R)—N-(3-(2-amino-5,5-difluoro-4-methyl-5,6-dihydro-4H-1,3-oxazin-4-yl)-4-fluorophenyl)-5-cyclopropyloxazole-4-carboxamide formate,
4-Chloro-1-difluoromethyl-1H-pyrazole-3-carboxylic acid [3-((R)-2-amino-5,5-difluoro-4-methyl-5,6-dihydro-4H-[1,3]oxazin-4-yl)-4-fluoro-phenyl]-amide,
(R)—N2-(3-(2-amino-5,5-difluoro-4-methyl-5,6-dihydro-4H-1,3-oxazin-4-yl)-4-fluorophenyl)pyridine-2,5-dicarboxamide,
N-[3-((R)-2-Amino-5,5-difluoro-4-methyl-5,6-dihydro-4H-[1,3]oxazin-4-yl)-4-fluoro-phenyl]-acetamide,
N-(3-((R)-2-amino-5,5-difluoro-4-methyl-5,6-dihydro-4H-1,3-oxazin-4-yl)-4-fluorophenyl)-2,2-difluorocyclopropanecarboxamide,
(R)—N-(3-(2-amino-5,5-difluoro-4-methyl-5,6-dihydro-4H-1,3-oxazin-4-yl)-4-fluorophenyl)-1-(trifluoromethyl)cyclopropanecarboxamide,
(R)—N-(3-((R)-2-amino-5,5-difluoro-4-methyl-5,6-dihydro-4H-1,3-oxazin-4-yl)-4-fluorophenyl)-3,3,3-trifluoro-2-hydroxy-2-methylpropanamide 2,2,2-trifluoroacetate,
(R)—N-(3-(2-amino-5,5-difluoro-4-methyl-5,6-dihydro-4H-1,3-oxazin-4-yl)-4-fluorophenyl)-4-chloro-1-ethyl-1H-pyrazole-3-carboxamide,
(R)—N-(3-(2-amino-5,5-difluoro-4-methyl-5,6-dihydro-4H-1,3-oxazin-4-yl)-4-fluorophenyl)-4-chloro-1-(2,2,2-trifluoro ethyl)-1H-pyrazole-3-carboxamide,
(R)—N-(3-(2-amino-5,5-difluoro-4-methyl-5,6-dihydro-4H-1,3-oxazin-4-yl)-4-fluorophenyl)-2-(fluoromethyl)oxazole-4-carboxamide formate,
Furan-2-carboxylic acid [3-((R)-2-amino-5,5-difluoro-4-methyl-5,6-dihydro-4H-[1,3]oxazin-4-yl)-4-fluoro-phenyl]-amide,
5-Nitro-furan-2-carboxylic acid [3-((R)-2-amino-5,5-difluoro-4-methyl-5,6-dihydro-4H-[1,3]oxazin-4-yl)-4-fluoro-phenyl]-amide,
(E)-N-[3-((R)-2-Amino-5,5-difluoro-4-methyl-5,6-dihydro-4H-[1,3]oxazin-4-yl)-4-fluoro-phenyl]-3-furan-2-yl-acrylamide, and
(R)-2-(3-(2-amino-5,5-difluoro-4-methyl-5,6-dihydro-4H-1,3-oxazin-4-yl)-4-fluorophenylcarbamoyl)-5-cyanopyridine 1-oxide,
or a pharmaceutical acceptable salt thereof.

A certain embodiment of the invention provides a compound of formula I as described herein, selected from the group consisting of
5-Chloro-pyridine-2-carboxylic acid [3-((R)-2-amino-5,5-difluoro-4-methyl-5,6-dihydro-4H-[1,3]oxazin-4-yl)-4-fluoro-phenyl]-amide,
5-Fluoro-pyridine-2-carboxylic acid [3-((R)-2-amino-5,5-difluoro-4-methyl-5,6-dihydro-4H-[1,3]oxazin-4-yl)-4-fluoro-phenyl]-amide,
3-Chloro-pyridine-2-carboxylic acid [3-((R)-2-amino-5,5-difluoro-4-methyl-5,6-dihydro-4H-[1,3]oxazin-4-yl)-4-fluoro-phenyl]-amide,
3,5-Difluoro-pyridine-2-carboxylic acid [3-((R)-2-amino-5,5-difluoro-4-methyl-5,6-dihydro-4H-[1,3]oxazin-4-yl)-4-fluoro-phenyl]-amide,
3-Chloro-5-trifluoromethyl-pyridine-2-carboxylic acid [3-((R)-2-amino-5,5-difluoro-4-methyl-5,6-dihydro-4H-[1,3]oxazin-4-yl)-4-fluoro-phenyl]-amide,
3-Trifluoromethyl-pyridine-2-carboxylic acid [3-((R)-2-amino-5,5-difluoro-4-methyl-5,6-dihydro-4H-[1,3]oxazin-4-yl)-4-fluoro-phenyl]-amide,
3-Chloro-5-fluoro-pyridine-2-carboxylic acid [3-((R)-2-amino-5,5-difluoro-4-methyl-5,6-dihydro-4H-[1,3]oxazin-4-yl)-4-fluoro-phenyl]-amide,
3,5-Dichloro-pyridine-2-carboxylic acid [3-((R)-2-amino-5,5-difluoro-4-methyl-5,6-dihydro-4H-[1,3]oxazin-4-yl)-4-fluoro-phenyl]-amide,
Pyridine-2-carboxylic acid [3-((R)-2-amino-5,5-difluoro-4-methyl-5,6-dihydro-4H-[1,3]oxazin-4-yl)-4-fluoro-phenyl]-amide,
3-Fluoro-pyridine-2-carboxylic acid [3-((R)-2-amino-5,5-difluoro-4-methyl-5,6-dihydro-4H-[1,3]oxazin-4-yl)-4-fluoro-phenyl]-amide,
5-Cyano-pyridine-2-carboxylic acid [3-((R)-2-amino-5,5-difluoro-4-methyl-5,6-dihydro-4H-[1,3]oxazin-4-yl)-4-fluoro-phenyl]-amide,
5-Chloro-pyrimidine-2-carboxylic acid [3-((R)-2-amino-5,5-difluoro-4-methyl-5,6-dihydro-4H-[1,3]oxazin-4-yl)-4-fluoro-phenyl]-amide,
5-Chloro-3-methyl-pyridine-2-carboxylic acid [3-((R)-2-amino-5,5-difluoro-4-methyl-5,6-dihydro-4H-[1,3]oxazin-4-yl)-4-fluoro-phenyl]-amide,
5-(2,2,2-Trifluoro-ethoxy)-pyridine-2-carboxylic acid [3-((R)-2-amino-5,5-difluoro-4-methyl-5,6-dihydro-4H-[1,3]oxazin-4-yl)-4-fluoro-phenyl]-amide,
5-Chloro-3-fluoro-pyridine-2-carboxylic acid [3-((R)-2-amino-5,5-difluoro-4-methyl-5,6-dihydro-4H-[1,3]oxazin-4-yl)-4-fluoro-phenyl]-amide,
5-Trifluoromethyl-pyrimidine-2-carboxylic acid [3-((R)-2-amino-5,5-difluoro-4-methyl-5,6-dihydro-4H-[1,3]oxazin-4-yl)-4-fluoro-phenyl]-amide,
5-Trifluoromethyl-pyrazine-2-carboxylic acid [3-((R)-2-amino-5,5-difluoro-4-methyl-5,6-dihydro-4H-[1,3]oxazin-4-yl)-4-fluoro-phenyl]-amide,
4-Chloro-1-methyl-1H-pyrazole-3-carboxylic acid [3-((R)-2-amino-5,5-difluoro-4-methyl-5,6-dihydro-4H-[1,3]oxazin-4-yl)-4-fluoro-phenyl]-amide,
5-Chloro-pyridine-2-carboxylic acid [3-((R)-2-amino-5,5-difluoro-4,6,6-trimethyl-5,6-dihydro-4H-[1,3]oxazin-4-yl)-4-fluoro-phenyl]-amide, and
3-Chloro-5-trifluoromethyl-pyridine-2-carboxylic acid [3-((R)-2-amino-5,5-difluoro-4,6,6-trimethyl-5,6-dihydro-4H-[1,3]oxazin-4-yl)-4-fluoro-phenyl]-amide.

A certain embodiment of the invention provides a compound of formula I as described herein, selected from the group consisting of
5-Chloro-pyridine-2-carboxylic acid [3-((R)-2-amino-5,5-difluoro-4-methyl-5,6-dihydro-4H-[1,3]oxazin-4-yl)-4-fluoro-phenyl]-amide,
3-Chloro-5-trifluoromethyl-pyridine-2-carboxylic acid [3-((R)-2-amino-5,5-difluoro-4-methyl-5,6-dihydro-4H-[1,3]oxazin-4-yl)-4-fluoro-phenyl]-amide,
3-Chloro-5-fluoro-pyridine-2-carboxylic acid [3-((R)-2-amino-5,5-difluoro-4-methyl-5,6-dihydro-4H-[1,3]oxazin-4-yl)-4-fluoro-phenyl]-amide, 3,5-Dichloro-pyridine-2-carboxylic acid [3-((R)-2-amino-5,5-difluoro-4-methyl-5,6-dihydro-4H-[1,3]oxazin-4-yl)-4-fluoro-phenyl]-amide, 5-Cyano-pyridine-2-carboxylic acid [3-((R)-2-amino-5,5-difluoro-4-methyl-5,6-dihydro-4H-[1,3]oxazin-4-yl)-4-fluoro-phenyl]-amide, 5-Chloro-3-fluoro-pyridine-2-carboxylic acid [3-((R)-2-amino-5,5-difluoro-4-methyl-5,6-dihydro-4H-[1,3]oxazin-4-yl)-4-fluoro-phenyl]-amide, 5-Chloro-pyridine-2-carboxylic acid [3-((R)-2-amino-5,5-difluoro-4,6,6-trimethyl-5,6-dihydro-4H-[1,3]oxazin-4-yl)-4-fluoro-phenyl]-amide, and 3-Chloro-5-trifluoromethyl-pyridine-2-carboxylic acid [3-((R)-2-amino-5,5-difluoro-4,6,6-trimethyl-5,6-dihydro-4H-[1,3]oxazin-4-yl)-4-fluoro-phenyl]-amide.

A certain embodiment of the invention provides a compound of formula I as described herein, selected from the group consisting of 5-Cyano-pyridine-2-carboxylic acid [3-((R)-2-amino-5,5-difluoro-4-methyl-5,6-dihydro-4H-[1,3]oxazin-4-yl)-4-fluoro-phenyl]-amide and 5-Cyano-pyridine-2-carboxylic acid [3-((R)-2-amino-5,5-difluoro-4-methyl-5,6-dihydro-4H-[1,3]oxazin-4-yl)-4-fluoro-phenyl]-amide hydrochloride.

A certain embodiment of the invention provides a process to synthesize a compound of formula I as described herein, which process comprises reacting a compound of formula II with a compound of formula III.

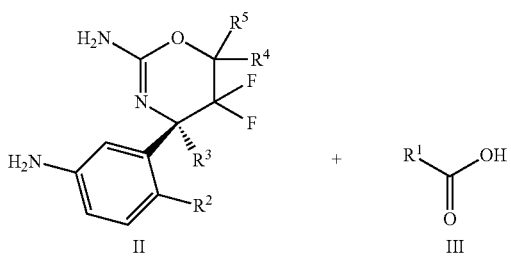

wherein $R^1$, $R^2$, $R^3$, $R^4$, $R^5$ are as herein.

A certain embodiment of the invention provides a compound of formula I as described herein, whenever prepared by a process as defined above.

A certain embodiment of the invention provides a compound of formula I as described herein for use as therapeutically active substance.

A certain embodiment of the invention provides a compound of formula I as described herein for the use as inhibitor of BACE1 and/or BACE2 activity.

A certain embodiment of the invention provides a compound of formula I as described herein for the use as inhibitor of BACE1 activity.

A certain embodiment of the invention provides a compound of formula I as described herein for the use as inhibitor of BACE2 activity.

A certain embodiment of the invention provides a compound of formula I as described herein for the use as inhibitor of BACE1 and BACE2 activity.

A certain embodiment of the invention provides a compound of formula I as described herein for the use as therapeutically active substance for the therapeutic and/or prophylactic treatment of diseases and disorders characterized by elevated β-amyloid levels and/or β-amyloid oligomers and/or β-amyloid plaques and further deposits, particularly Alzheimer's disease.

A certain embodiment of the invention provides a compound of formula I as described herein for the use as therapeutically active substance for the therapeutic and/or prophylactic treatment of Alzheimer's disease.

A certain embodiment of the invention provides a compound of formula I as described herein for the use as therapeutically active substance for the therapeutic and/or prophylactic treatment of diabetes, particularly type 2 diabetes.

A certain embodiment of the invention provides a compound of formula I as described herein for the use as therapeutically active substance for the therapeutic and/or prophylactic treatment of amyotrophic lateral sclerosis (ALS), arterial thrombosis, autoimmune/inflammatory diseases, cancer such as breast cancer, cardiovascular diseases such as myocardial infarction and stroke, dermatomyositis, Down's Syndrome, gastrointestinal diseases, Glioblastoma multiforme, Graves Disease, Huntington's Disease, inclusion body myositis (IBM), inflammatory reactions, Kaposi Sarcoma, Kostmann Disease, lupus erythematosus, macrophagic myofasciitis, juvenile idiopathic arthritis, granulomatous arthritis, malignant melanoma, multiple mieloma, rheumatoid arthritis, Sjogren syndrome, SpinoCerebellar Ataxia 1, SpinoCerebellar Ataxia 7, Whipple's Disease or Wilson's Disease.

A certain embodiment of the invention provides a pharmaceutical composition comprising a compound of formula I as described herein and a pharmaceutically acceptable carrier and/or a pharmaceutically acceptable auxiliary substance.

A certain embodiment of the invention provides the use of a compound of formula I as described herein for the manufacture of a medicament for the use in inhibition of BACE1 and/or BACE2 activity.

A certain embodiment of the invention provides the use of a compound of formula I as described herein for the manufacture of a medicament for the use in inhibition of BACE1 activity.

A certain embodiment of the invention provides the use of a compound of formula I as described herein for the manufacture of a medicament for the use in inhibition of BACE2 activity.

A certain embodiment of the invention provides the use of a compound of formula I as described herein for the manufacture of a medicament for the use in inhibition of BACE1 and BACE2 activity.

A certain embodiment of the invention provides the use of a compound of formula I as described herein for the manufacture of a medicament for the therapeutic and/or prophylactic treatment of diseases and disorders characterized by elevated β-amyloid levels and/or β-amyloid oligomers and/or β-amyloid plaques and further deposits, particularly Alzheimer's disease.

A certain embodiment of the invention provides the use of a compound of formula I as described herein for the manufacture of a medicament for the therapeutic and/or prophylactic treatment of Alzheimer's disease.

A certain embodiment of the invention provides the use of a compound of formula I as described herein for the manufacture of a medicament for the therapeutic and/or prophylactic treatment of diabetes, particularly type 2 diabetes.

A certain embodiment of the invention provides a compound of formula I as described herein for the use in inhibition of BACE1 and/or BACE2 activity.

A certain embodiment of the invention provides a compound of formula I as described herein for the use in inhibition of BACE1 activity.

A certain embodiment of the invention provides a compound of formula I as described herein for the use in inhibition of BACE2 activity.

A certain embodiment of the invention provides a compound of formula I as described herein for the use in inhibition of BACE1 and BACE2 activity.

A certain embodiment of the invention provides a compound of formula I as described herein for the use in the therapeutic and/or prophylactic treatment of diseases and disorders characterized by elevated β-amyloid levels and/or β-amyloid oligomers and/or β-amyloid plaques and further deposits, particularly Alzheimer's disease.

A certain embodiment of the invention provides a compound of formula I as described herein for the use in the therapeutic and/or prophylactic treatment of Alzheimer's disease.

A certain embodiment of the invention provides a compound of formula I as described herein for the use in the therapeutic and/or prophylactic treatment of diabetes, particularly type 2 diabetes.

A certain embodiment of the invention provides a method for the use in inhibition of BACE1 and/or BACE2 activity, particularly for the therapeutic and/or prophylactic treatment of diseases and disorders characterized by elevated β-amyloid levels and/or β-amyloid oligomers and/or β-amyloid plaques and further deposits, Alzheimer's disease, diabetes or type 2 diabetes, which method comprises administering compound of formula I as described herein to a human being or animal.

Furthermore, the invention includes all optical isomers, i.e. diastereoisomers, diastereomeric mixtures, racemic mixtures, all their corresponding enantiomers and/or tautomers as well as their solvates.

The skilled person in the art will recognize that the compounds of formula I can exist in tautomeric forms, e.g. in the following tautomeric form:

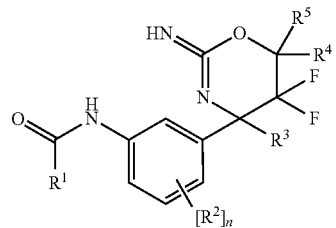

Id

All tautomeric forms are encompassed in the present invention.

The compounds of formula I can contain one or more asymmetric centers and can therefore occur as racemates, racemic mixtures, single enantiomers, diastereomeric mixtures and individual diastereomers. Additional asymmetric centers can be present depending upon the nature of the various substituents on the molecule. Each such asymmetric centre will independently produce two optical isomers and it is intended that all of the possible optical isomers and diastereomers in mixtures and as pure or partially purified compounds are included within this invention. The present invention is meant to encompass all such isomeric forms of these compounds. The independent syntheses of these diastereomers or their chromatographic separations can be achieved as known in the art by appropriate modification of the methodology disclosed herein. Their absolute stereochemistry can be determined by the x-ray crystallography of crystalline products or crystalline intermediates which are derivatized, if necessary, with a reagent containing an asymmetric centre of known absolute configuration. If desired, racemic mixtures of the compounds can be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. Preferred examples of isomers of a compound of formula I is a compound of formula Ib or a compound of formula Ic, wherein the residues have the meaning as described in any of the embodiments. Preferred is compound of formula Ic.

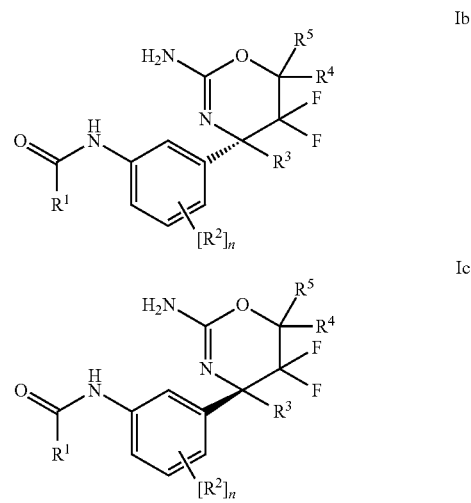

In the embodiments, where optically pure enantiomers are provided, optically pure enantiomer means that the compound contains >90% of the desired isomer by weight, preferably >95% of the desired isomer by weight, or more preferably >99% of the desired isomer by weight, said weight percent based upon the total weight of the isomer(s) of the compound. Chirally pure or chirally enriched compounds can be prepared by chirally selective synthesis or by separation of enantiomers. The separation of enantiomers can be carried out on the final product or alternatively on a suitable intermediate.

The compounds of formula I can be prepared in accordance with the following schemes. The starting material is commercially available or can be prepared in accordance with known methods. Any previously defined residues and variables will continue to have the previously defined meaning unless otherwise indicated.

Sulfinyl imines of general formula VI can be prepared in analogy to T. P. Tang & J. A. Ellman, J. Org. Chem. 1999, 64, 12, by condensation of an aryl ketone IV and a sulfonamide V, e.g. an alkyl sulfinamide, most preferably (R)-(+)-tert-butyl-sulfinamide in the presence of a Lewis acid such as e.g. a titanium(IV) alkoxide, more preferably titanium(IV) ethoxide in a solvent such as an ether, e.g. diethyl ether or more preferably THF.

The conversion of the sulfinyl imine VI to the sulfinamide ester VII proceeds stereoselectively by the chiral directing group as described by Tang & Ellman. The sulfinyl imine VI can be reacted in a Reformatsky reaction with a zinc enolate generated from e.g. an alkyl bromodifluoroacetate, preferably ethyl bromodifluoroacetate, activated zinc powder at ambient to elevated temperature, preferably at 23 to 60° C. in a solvent such as an ether, e.g. diethyl ether or more preferably THF.

Alcohol VIII can be prepared by the reduction of the ethy-lester VII with an alkali hydride, preferably lithium borohydride or lithium aluminium hydride in a solvent such as an ether, e.g. diethyl ether or more preferably THF.

Hydrolysis of the chiral directing group in the sulfinamide alcohol VIII to give the aminoalcohol IX can be accomplished with a mineral acid, e.g. sulfuric acid or preferably hydrochloric acid in a solvent such as an ether, e.g. diethyl ether, THF or more preferably 1,4-dioxane.

Difluoro-aminooxazines X can be prepared by reaction of aminoalcohol IX with cyanogen bromide in a solvent such as an alcohol, preferably ethanol.

The reduction of the nitro group in the aminooxazine X to the aniline XI can be accomplished by hydrogenation using a catalysts such as Pd/C in protic solvents, such as alcohols, preferably ethanol or methanol.

Selective amide coupling of the aniline XI and a carboxylic acid to give the amide XIII can be effected with 4-(4,6-dimethoxy[1.3.5]triazin-2-yl)-4-methylmorpholinium chloride (DMTMM) hydrate in a solvent such as methanol.

Anilines of formula XI', wherein $R^{2'}$ has the meaning of halogen or lower alkyl, can further be transformed to iodo derivatives of formula XIII' by iodonium donating systems using iodides as an iodide source, like e.g. ammonium iodide, Scheme 1: Synthesis of XIII

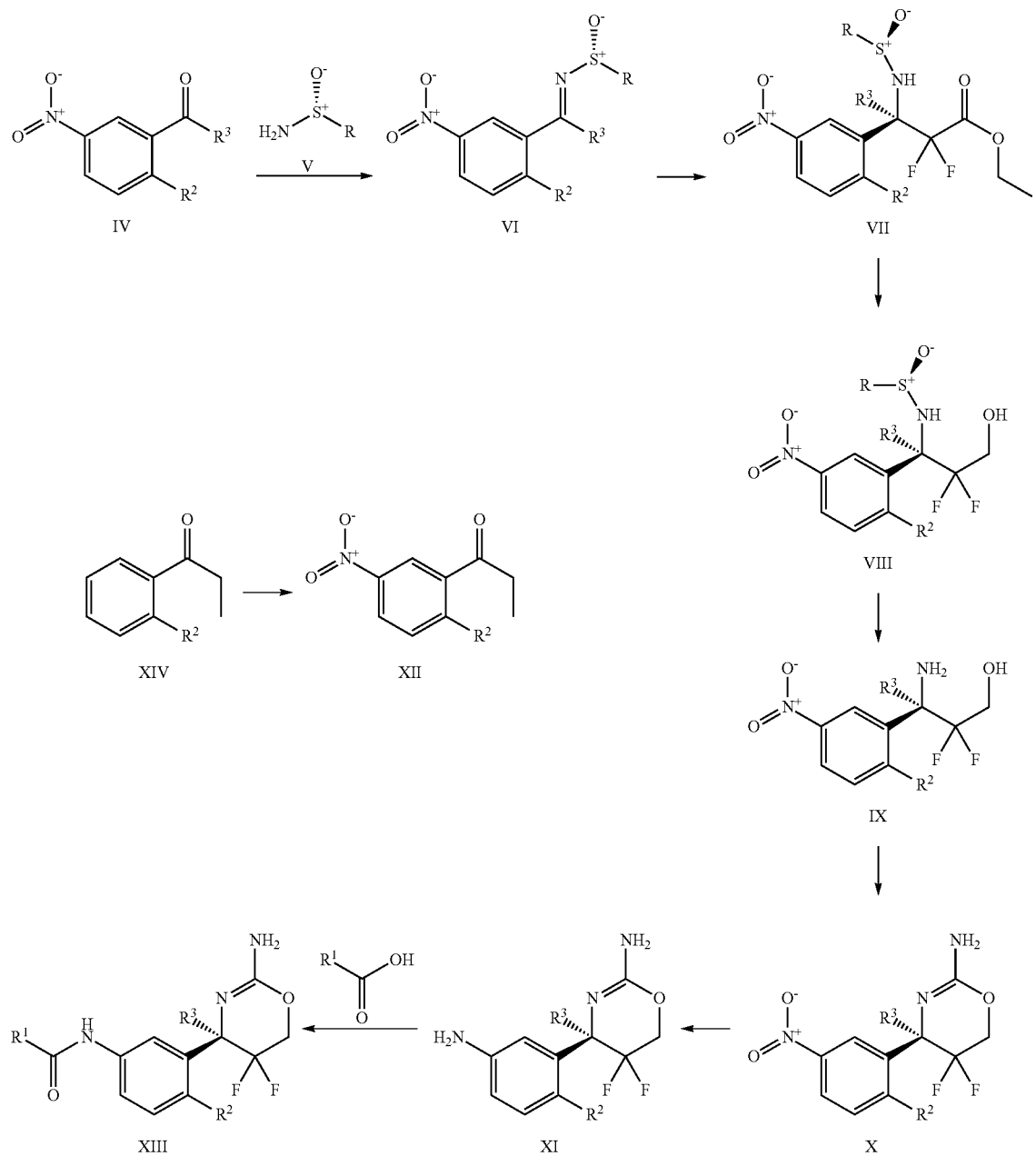

R = lower alkyl, preferably t-butyl together with a strong oxidising agent, like e.g. hydrogen peroxide, in a polar solvent, like e.g. acetic acid, and as described by N. Narender et al. in Tetrahedron Letters 48 (2007) 6124-6128.

Scheme 2: Syntheses of compounds of formula XIII and XIII′

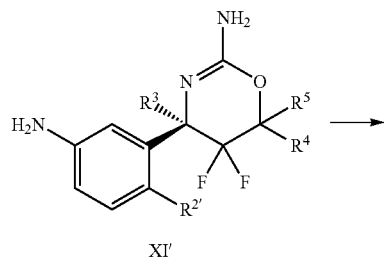

XI′

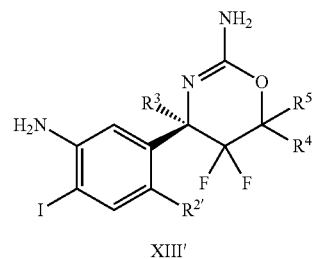

XIII′

Another typical procedure for the preparation of compounds of formula I is illustrated in Scheme 3.

Scheme 3: Synthesis of intermediates XI

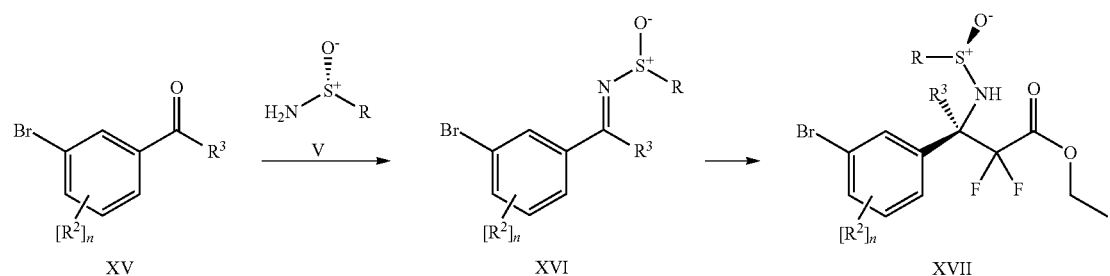

XV     XVI     XVII $R^3$: Me [198477-89-3]
$R^3$: Et [864774-65-2]

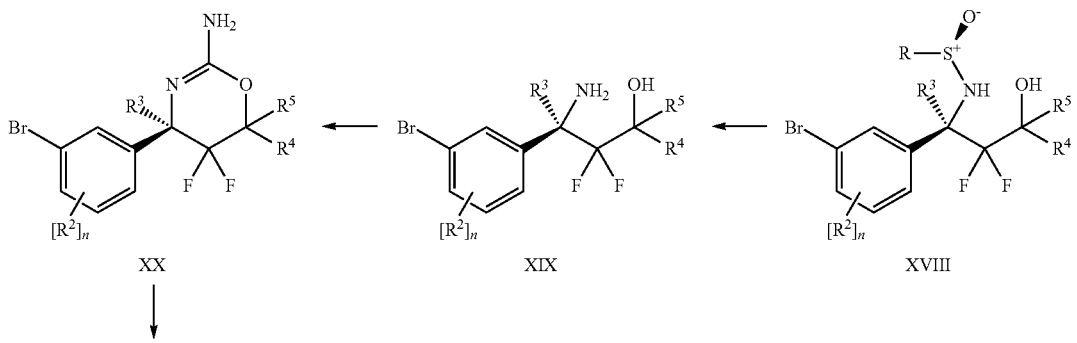

XX     XIX     XVIII

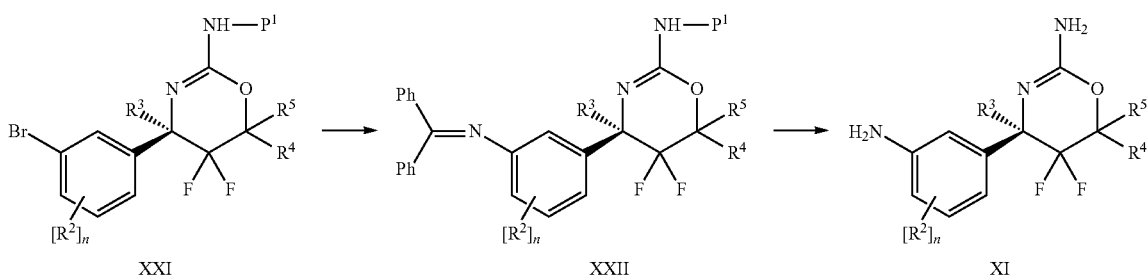

XXI     XXII     XI $P^1$: e.g. Tr, MMTr, DMTr, TMTr

Sulfinyl imines of general formula XVI can be prepared in analogy to the description mentioned above for the preparation of sulfinyl imines of general formula VI.

The conversion of the sulfinyl imine XVI to the sulfinamide ester XVII proceeds in an analogous manner as previously described for the preparation of sulfinamide ester VII. The alcohol of general formula XIX, wherein $R^4$ and $R^5$ are hydrogen, can be prepared again in an analogous manner as described above for the alcohol VIII. The alcohols of general formula XVIII, wherein $R^4$ and $R^5$ are $C_{1-7}$-alkyl, can be prepared by reacting the sulfinamide ester XVII with an excess of an organometallic reagent bearing the corresponding $C_{1-7}$-alkyl groups, such as a $C_{1-7}$-alkyllithium or $C_{1-7}$-alkylmagnesium halide compound, in etheral solvents, such as diethyl ether or THF, at temperatures between −78° C. and ambient temperature.

Hydrolysis of the chiral directing group in the sulfinamide alcohols of general formula XVIII proceeds in an analogous manner as described above for the sulfinamide ester VIII to give here the aminoalcohol XIX.

Aminooxazines of general formula XX can again be prepared as described above by reaction of aminoalcohol XIX with cyanogen bromide in a solvent such as an alcohol, preferably ethanol.

The protection of the amino group in compounds of general formula XX to produce aryl bromides of general formula XXI can be performed with triarylmethyl chlorides, such as triphenylmethyl chloride (Tr-Cl), p-methoxyphenyldiphenylmethyl chloride (MMTr-Cl), di(p-methoxyphenyl)phenylmethyl chloride (DMTr-Cl) or tri(p-methoxyphenyl)methyl chloride (TMTr-Cl), preferably DMTr-Cl, under basic conditions, e.g. in the presence of an amine, such as triethylamine or diisopropylethylamine, in a chlorinated solvent, such as dichloromethane or chloroform, at temperatures between 0° C. and ambient temperature.

Aryl bromides of general formula XXI can be reacted with ammonia equivalents, such as benzophenone imine, in the presence of a suitable transition metal catalyst, such as bis(dibenzylideneacetone)palladium (0) ((dba)$_2$Pd) or tris(dibenzylideneacetone)dipalladium (0) ((dba)$_3$Pd$_2$)), and a suitable ligand, such as rac-2,2'-bis(diphenylphosphino)-1,1'-binaphthyl (rac-BINAP), 2-dicyclohexylphosphino-2',4',6'-triisopropylbiphenyl (X-PHOS) or 2-di-tert-butylphosphino-2',4',6'-triisopropylbiphenyl (t-Bu X-phos), in the presence of a base, such as sodium tert-butoxide, potassium phosphate or cesium carbonate, in a suitable solvent, such as toluene or 1,4-dioxane, under an inert atmosphere, such as nitrogen or argon, at temperatures between 80 and 110° C., to produce compounds of general formula XXII.

Alternatively, the reaction of aryl bromides of general formula XXI with lithium hexamethyldisilazide in the presence of a suitable transition metal catalyst and a suitable ligand, such mentioned above following a protocol as for example described by J. F. Hartwing et al. in Organic Letters 3(17), 2729-32 (2001) can result in an amine of general formula M.

Deprotection of both amino groups in compounds of general formula XXII can be achieved by a one-pot procedure by first reacting it with a strong organic acid, such as trifluoroacetic acid, in chlorinated solvents, such as dichloromethane or chloroform, under anhydrous conditions at temperatures between 0° C. and ambient temperature to cleave the $P^1$-group, then by addition of water to cleave the benzophenone imine and reaction at ambient temperature to produce diamines of general formula XI, which can be transformed to compounds of general formula I as described above.

Scheme 4: Synthesis of compounds of formula I with $R^4$, $R^5$ = H

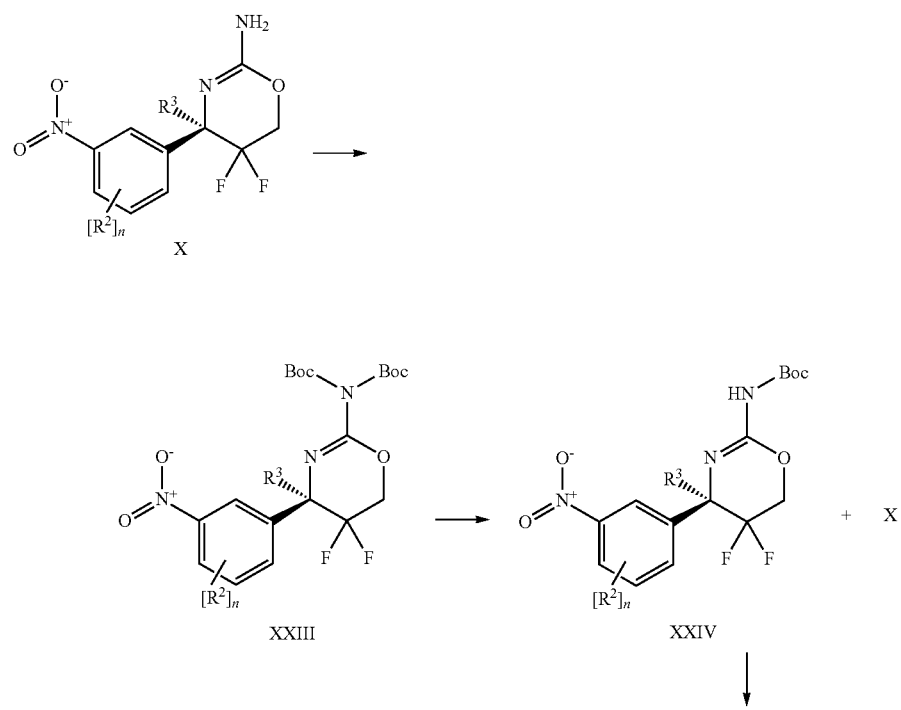

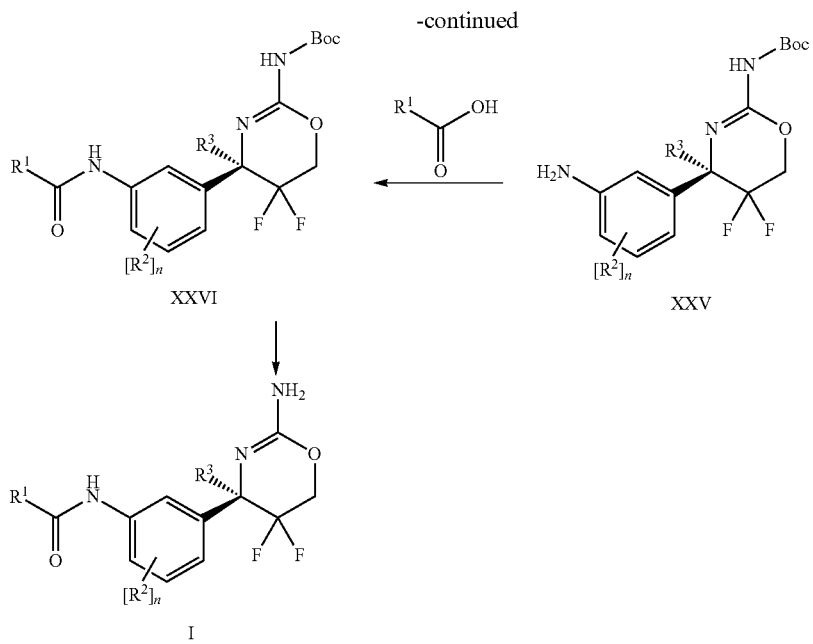

The protection of the amino group in compounds of general formula X to produce nitro aryl derivatives of general formula XXIII, wherein $R^2$ has the meaning of hydrogen, fluorine, chlorine or lower alkyl, can be performed with di-tert-butyl dicarbonate under basic conditions, e.g. in the presence of an amine, such as triethylamine or diisopropylethylamine, in a solvent, such as tetrahydrofuran, at temperatures between 0° C. and ambient temperature and in presence of 4-dimethylamino-pyridine as a catalyst.

Selective cleavage of one of the tert-butoxy carbonyl groups in compounds of general formula XXIII can be performed by acid, such as trifluoroacetic acid, to produce compounds of general formula XXIV together with small amounts of compounds of general formula X.

The reduction of the nitro group in the aminooxazine XXIV to the aniline XXV can be accomplished by hydrogenation using a catalysts such as Pd/C in protic solvents, such as alcohols, perferrably ethanol or methanol.

Amide coupling of the aniline XXV and a carboxylic acid to give the amides of general formula XXVI can be effected in a solvent such as methanol with 4-(4,6-dimethoxy[1.3.5]triazin-2-yl)-4-methylmorpholinium chloride hydrate (DMTMM) or other condensating agents, such as O-(benzotriazol-1-yl)-N,N,N',N'-tetramethyluronium.-hexafluorophosphate (HBTU) or O-(7-azabenzotriazol-1-yl)-N,N,N',N'-tetramethyluronium-hexafluorophosphate (HATU), in the presence of an amine, such as triethylamine or diisopropylethylamine, in a solvent, such as acetonitrile or N,N-dimthylformamide, at temperatures between 0° C. and ambient temperature.

The cleavage of the protecting tert-butoxy carbonyl group in compounds of general formula XXVI to produce compounds of general formula I can be effected by acid, such as trifluoroacetic acid, in inert solvents, such as dichloromethane, at temperatures between 0° C. and ambient temperature.

The corresponding pharmaceutically acceptable salts with acids can be obtained by standard methods known to the person skilled in the art, e.g. by dissolving the compound of formula I in a suitable solvent such as e.g. dioxan or THF and adding an appropriate amount of the corresponding acid. The products can usually be isolated by filtration or by chromatography. The conversion of a compound of formula I into a pharmaceutically acceptable salt with a base can be carried out by treatment of such a compound with such a base. One possible method to form such a salt is e.g. by addition of 1/n equivalents of a basic salt such as e.g. $M(OH)_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilisation.

Insofar as their preparation is not described in the examples, the compounds of formula I as well as all intermediate products can be prepared according to analogous methods or according to the methods set forth herewithin. Starting materials are commercially available, known in the art or can be prepared by methods known in the art or in analogy thereto.

It will be appreciated that the compounds of general formula I in this invention can be derivatised at functional groups to provide derivatives which are capable of conversion back to the parent compound in vivo.

Pharmacological Tests

The compounds of formula I and their pharmaceutically acceptable salts possess valuable pharmacological properties. Compounds of the present invention are associated with inhibition of BACE1 and/or BACE2 activity. The compounds were investigated in accordance with the test given hereinafter.

Cellular Aβ-Lowering Assay:

Human HEK293 cells which are stably transfected with a vector expressing a cDNA of the human APP wt gene (APP695) were used to assess the potency of the compounds in a cellular assay. The cells were seeded in 96-well microtiter plates in cell culture medium (Iscove, plus 10% (v/v) fetal bovine serum, glutamine, penicillin/streptomycin) to about 80% confluence and the compounds were added at a 10× concentration in 1/10 volume of medium without FCS containing 8% DMSO (final concentration of DMSO was kept at 0.8% v/v). After 18-20 hrs incubation at 37° C. and 5% $CO_2$ in a humidified incubator the culture supernatant was harvested for the determination of Aβ40 concentrations. 96 well ELISA plates (e.g., Nunc MaxiSorb) were coated with monoclonal antibody which specifically recognize the C-terminal end of Aβ40 (Brockhaus et al., NeuroReport 9, 1481-1486; 1998). After blocking of non-specific binding sites with e.g. 1% BSA and washing, the culture supernatants were added in suitable dilutions together with a horseradish peroxidase-coupled Aβ detection antibody (e.g., antibody 4G8, Senetek, Maryland Heights, Mo.) and incubated for 5 to 7 hrs. Subsequently the wells of the microtiter plate were washed extensively with Tris-buffered saline containing 0.05% Tween 20 and the assay was developed with tetramethylbenzidine/$H_2O_2$ in citric acid buffer. After stopping the reaction with one volume 1 $NH_2SO_4$ the reaction was measured in an ELISA reader at 450 nm wavelength. The concentrations of Aβ in the culture supernatants were calculated from a standard curve obtained with known amounts of pure Aβ peptide.

Assay for BACE Inhibition by Measuring Cellular TMEM27 Cleavage:

The assay uses the principle of inhibition of human TMEM27 cleavage by endogenous cellular BACE2 in the Ins1e rat cell line and shedding from the cell surface into the culture medium, followed by detection in an ELISA assay. Inhibition of BACE2 prevents the cleavage and shedding in a dose-dependent manner.

The stable cell line "INS-TMEM27" represents an INS1e-derived cell line with inducible expression (using the TetOn system) of full-length hTMEM27 in a doxycycline-dependent manner. The cells are cultured throughout the experiment in RPMI1640+Glutamax (Invitrogen) Penicillin/Streptomycin, 10% Fetal bovine serum, 100 mM pyruvate, 5 mM beta-mercatptoethanol, 100 micrograms/ml G418 and 100 microgram/ml hygromycin and are grown inadherent culture at 37° C. in a standard $CO_2$ cell culture incubator. INS-TMEM27 cells are seeded in 96-well plates. After 2 days in culture, BACE2 inhibitor is added in a range of concentrations as required by the assay and after a further two hours, doxycycline is added to a final concentration of 500 ng/ml. The cells are incubated for a further 46 hours and the supernatant harvested for detection of shed TMEM27.

An ELISA assay (using a pair of mouse anti-human-TMEM27 antibodies, raised against the extracellular domain of TMEM27) is used for detection of TMEM27 in the culture medium. An $EC_{50}$ for BACE2 inhibition is calculated using the ELISA readout for each inhibitor concentration with standard curve-fitting software such as XLFit for the Excel spreadsheet program.

TABLE 1

| | $IC_{50}$ values of selected examples | | |
|---|---|---|---|
| Exam. | Structure | BACE1 cell act. Aβ40 $IC_{50}$ [μM] | BACE2 cell act. $IC_{50}$ [μM] |
| 1 | | 0.010 | 0.035 |
| 2 | | 0.013 | 0.056 |
| 3 | | 0.087 | 0.052 |
| 4 | | 0.031 | 0.026 |

TABLE 1-continued
IC$_{50}$ values of selected examples
| Exam. | Structure | BACE1 cell act. Aβ40 IC$_{50}$ [μM] | BACE2 cell act. IC$_{50}$ [μM] |
|---|---|---|---|
| 5 | 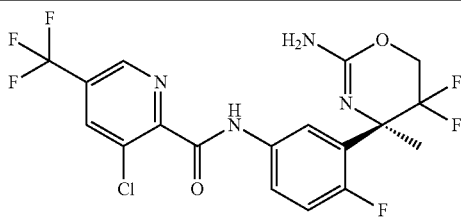 | 0.043 | 0.015 |
| 6 | 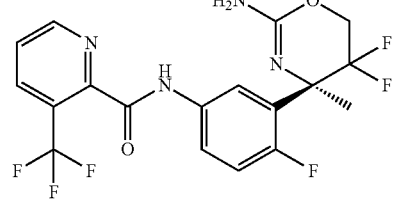 | 0.180 | 0.330 |
| 7 | 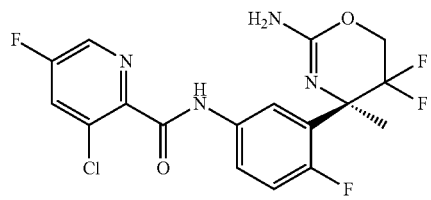 [SMILES: C[C@]1(c2cc(NC(=O)c3ncc(F)cc3Cl)ccc2F)N=C(N)OCC1(F)F] | 0.041 | 0.049 |
| 8 | 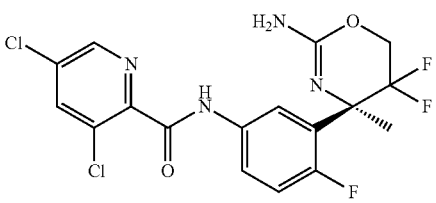 [SMILES: C[C@]1(c2cc(NC(=O)c3ncc(Cl)cc3Cl)ccc2F)N=C(N)OCC1(F)F] | 0.015 | 0.071 |
| 9 | 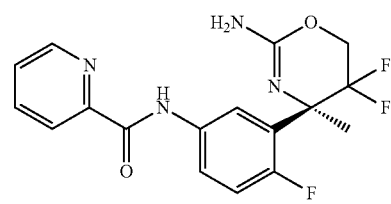 [SMILES: C[C@]1(c2cc(NC(=O)c3ccccn3)ccc2F)N=C(N)OCC1(F)F] | 0.180 | 0.082 |
| 10 | 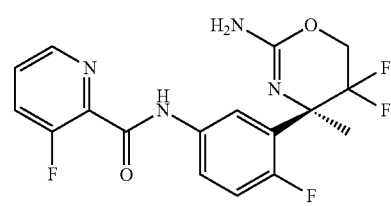 | 0.087 | 0.052 |
| 11 | 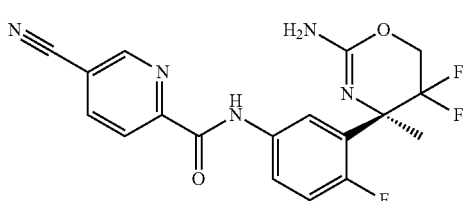 | 0.018 | 0.074 |

TABLE 1-continued

IC₅₀ values of selected examples

| Exam. | Structure | BACE1 cell act. Aβ40 IC$_{50}$ [μM] | BACE2 cell act. IC$_{50}$ [μM] |
|---|---|---|---|
| 12 | 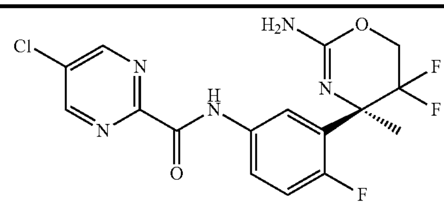 | 0.023 | 0.069 |
| 13 | 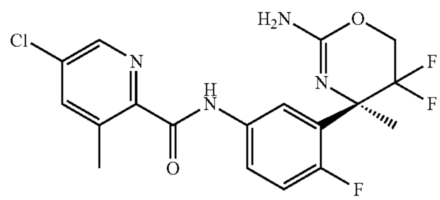 | 0.008 | 0.024 |
| 14 | 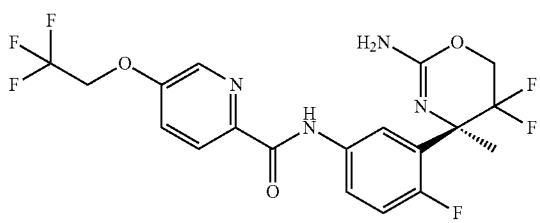 [SMILES: C[C@]1(c2cc(NC(=O)c3ccc(OCC(F)(F)F)cn3)ccc2F)N=C(N)OCC1(F)F] | 0.290 | 19.220 |
| 15 | 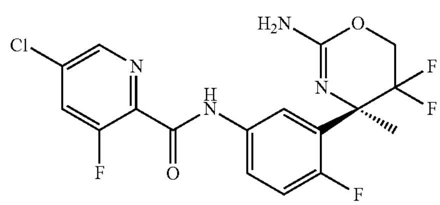 [SMILES: C[C@]1(c2cc(NC(=O)c3ncc(Cl)cc3F)ccc2F)N=C(N)OCC1(F)F] | 0.009 | 0.052 |
| 16 | 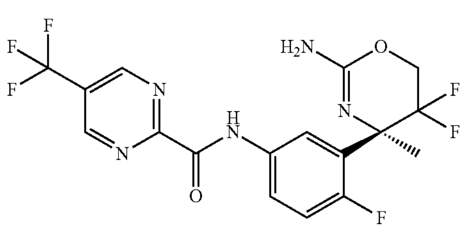 [SMILES: C[C@]1(c2cc(NC(=O)c3ncc(C(F)(F)F)cn3)ccc2F)N=C(N)OCC1(F)F] | 0.091 | 1.540 |
| 17 | 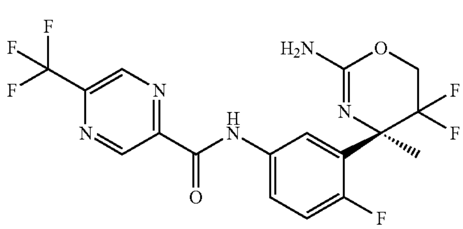 [SMILES: C[C@]1(c2cc(NC(=O)c3cnc(C(F)(F)F)cn3)ccc2F)N=C(N)OCC1(F)F] | 0.086 | 1.220 |
| 18 | 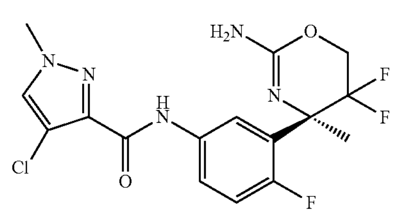 [SMILES: Cn1cc(Cl)c(C(=O)Nc2ccc(F)c([C@@]3(C)N=C(N)OCC3(F)F)c2)n1] | 0.061 | 0.015 |

TABLE 1-continued

IC$_{50}$ values of selected examples

| Exam. | Structure | BACE1 cell act. Aβ40 IC$_{50}$ [μM] | BACE2 cell act. IC$_{50}$ [μM] |
| --- | --- | --- | --- |
| 19 | 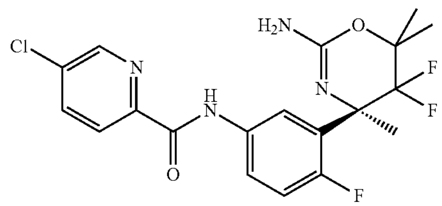 [SMILES: CC1(C)OC(N)=N[C@](C)(c2cc(NC(=O)c3ccc(Cl)cn3)ccc2F)C1(F)F] | 0.070 | 0.120 |
| 20 | 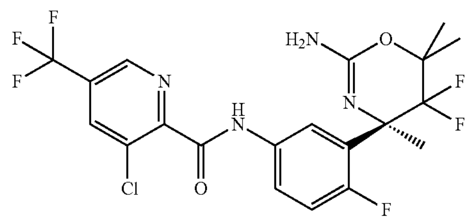 [SMILES: CC1(C)OC(N)=N[C@](C)(c2cc(NC(=O)c3ncc(C(F)(F)F)cc3Cl)ccc2F)C1(F)F] | 0.050 | 1.270 |
| 21 | 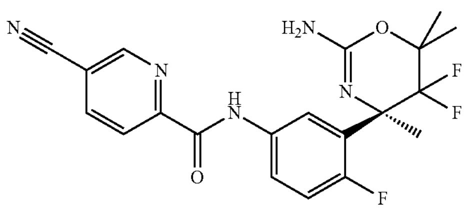 [SMILES: CC1(C)OC(N)=N[C@](C)(c2cc(NC(=O)c3ccc(C#N)cn3)ccc2F)C1(F)F] | 0.007 | 0.210 |
| 22 | 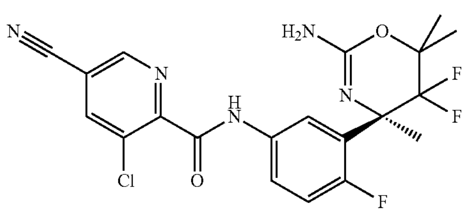 [SMILES: CC1(C)OC(N)=N[C@](C)(c2cc(NC(=O)c3ncc(C#N)cc3Cl)ccc2F)C1(F)F] | 0.007 | 0.175 |
| 23 | 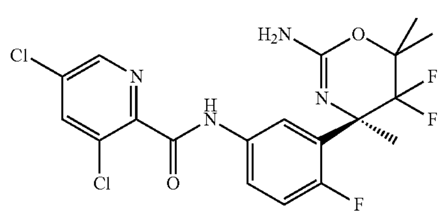 | 0.011 | 0.066 |
| 24 | 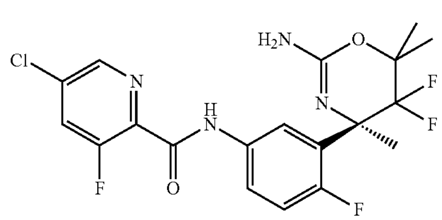 [SMILES: CC1(C)OC(N)=N[C@](C)(c2cc(NC(=O)c3ncc(Cl)cc3Cl)ccc2F)C1(F)F] | 0.012 | 0.070 |

TABLE 1-continued

IC$_{50}$ values of selected examples

| Exam. | Structure | BACE1 cell act. Aβ40 IC$_{50}$ [μM] | BACE2 cell act. IC$_{50}$ [μM] |
|---|---|---|---|
| 25 | 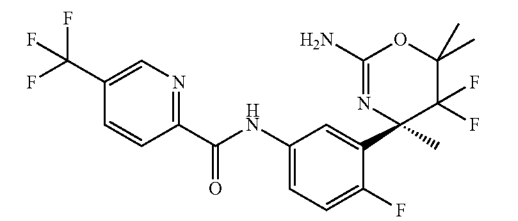 [SMILES: CC1(C)OC(N)=N[C@](C)(c2cc(NC(=O)c3ccc(C(F)(F)F)cn3)ccc2F)C1(F)F] | 0.025 | 2.253 |
| 26 | 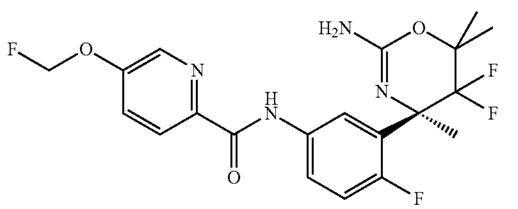 | 0.030 | 0.761 |
| 27 | 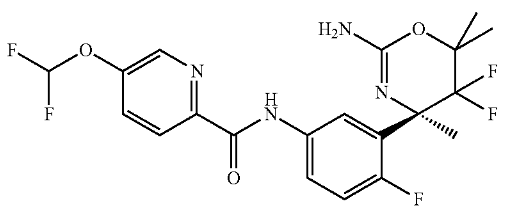 [SMILES: CC1(C)OC(N)=N[C@](C)(c2cc(NC(=O)c3ccc(OC(F)F)cn3)ccc2F)C1(F)F] | 0.047 | 5.354 |
| 28 | 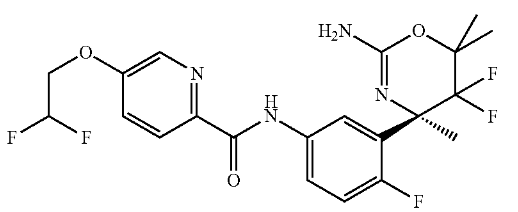 [SMILES: CC1(C)OC(N)=N[C@](C)(c2cc(NC(=O)c3ccc(OCC(F)F)cn3)ccc2F)C1(F)F] | 0.200 | |
| 29 | 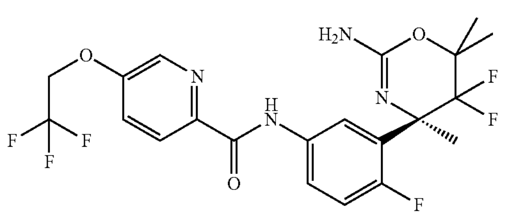 | 0.140 | 44.290 |
| 30 | 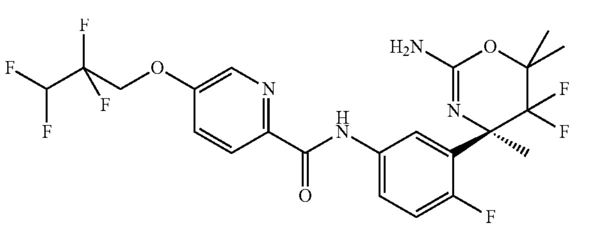 [SMILES: CC1(C)OC(N)=N[C@](C)(c2cc(NC(=O)c3ccc(OCC(F)(F)C(F)F)cn3)ccc2F)C1(F)F] | 0.230 | |

TABLE 1-continued

IC$_{50}$ values of selected examples

| Exam. | Structure | BACE1 cell act. Aβ40 IC$_{50}$ [μM] | BACE2 cell act. IC$_{50}$ [μM] |
|---|---|---|---|
| 31 | 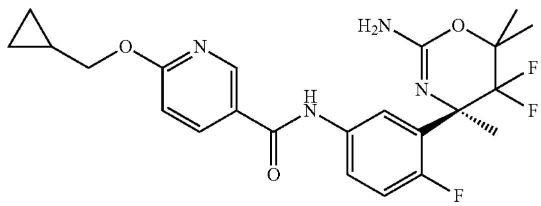 [SMILES: CC1(C)OC(N)=N[C@](C)(c2cc(NC(=O)c3ccc(OCC4CC4)nc3)ccc2F)C1(F)F] | 2.810 | |
| 32 | 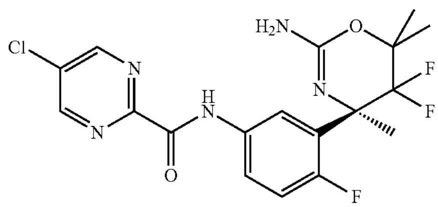 [SMILES: CC1(C)OC(N)=N[C@](C)(c2cc(NC(=O)c3ncc(Cl)cn3)ccc2F)C1(F)F] | 0.016 | 0.020 |
| 33 | 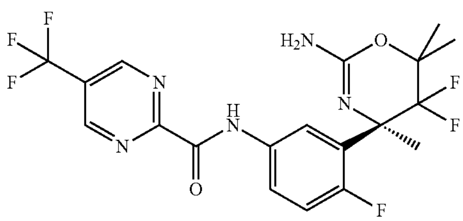 | 0.029 | 2.610 |
| 34 | 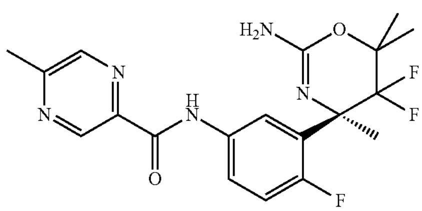 | 0.043 | 3.576 |
| 35 | 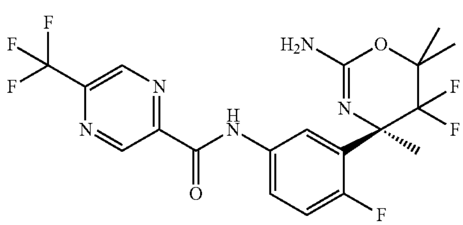 [SMILES: CC1(C)OC(N)=N[C@](C)(c2cc(NC(=O)c3cnc(C(F)(F)F)cn3)ccc2F)C1(F)F] | 0.040 | 4.750 |
| 36 | 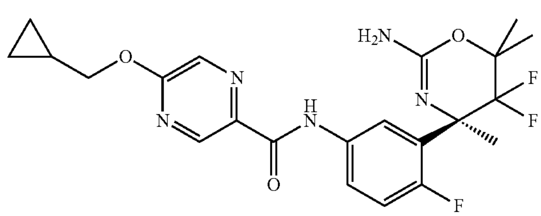 [SMILES: CC1(C)OC(N)=N[C@](C)(c2cc(NC(=O)c3cnc(OCC4CC4)cn3)ccc2F)C1(F)F] | 2.460 | |

TABLE 1-continued

IC₅₀ values of selected examples

| Exam. | Structure | BACE1 cell act. Aβ40 IC$_{50}$ [µM] | BACE2 cell act. IC$_{50}$ [µM] |
|---|---|---|---|
| 37 | 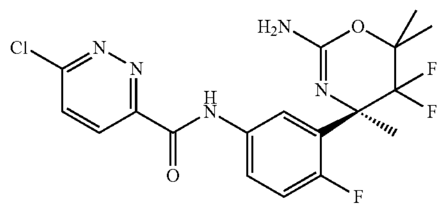 [SMILES: CC1(C)OC(N)=N[C@](C)(c2cc(NC(=O)c3ccc(Cl)nn3)ccc2F)C1(F)F] | 0.710 | 50.73 |
| 38 | 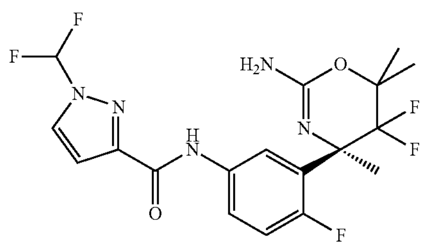 [SMILES: CC1(C)OC(N)=N[C@](C)(c2cc(NC(=O)c3ccn(C(F)F)n3)ccc2F)C1(F)F] | 0.006 | |
| 39 | 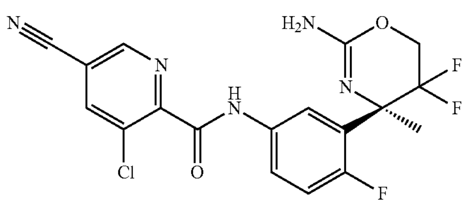 [SMILES: C[C@]1(c2cc(NC(=O)c3ncc(C#N)cc3Cl)ccc2F)N=C(N)OCC1(F)F] | 0.028 | 0.224 |
| 40 | 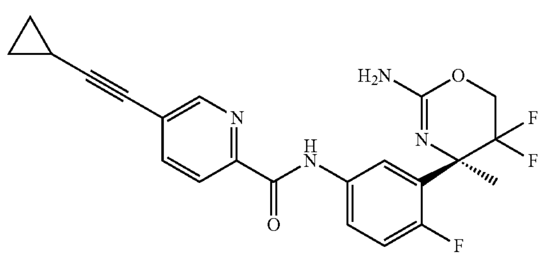 [SMILES: C[C@]1(c2cc(NC(=O)c3ccc(C#CC4CC4)cn3)ccc2F)N=C(N)OCC1(F)F] | 0.460 | |
| 41 | 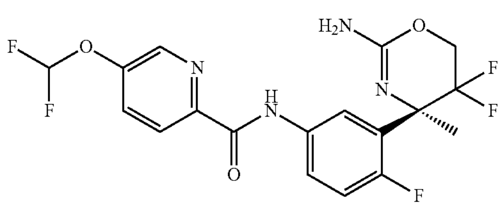 | 0.011 | 0.855 |
| 42 | 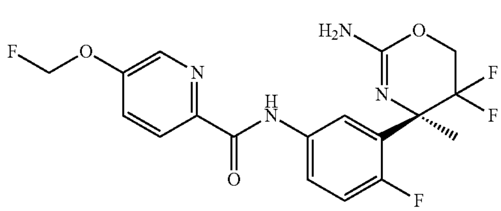 [SMILES: C[C@]1(c2cc(NC(=O)c3ccc(OCF)cn3)ccc2F)N=C(N)OCC1(F)F] | 0.029 | 0.300 |

TABLE 1-continued
IC$_{50}$ values of selected examples
| Exam. | Structure | BACE1 cell act. Aβ40 IC$_{50}$ [μM] | BACE2 cell act. IC$_{50}$ [μM] |
|---|---|---|---|
| 43 | 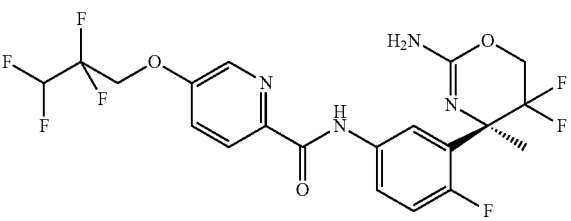 [SMILES: C[C@]1(c2cc(NC(=O)c3ccc(OCC(F)(F)C(F)F)cn3)ccc2F)N=C(N)OCC1(F)F] | 0.100 | |
| 44 | 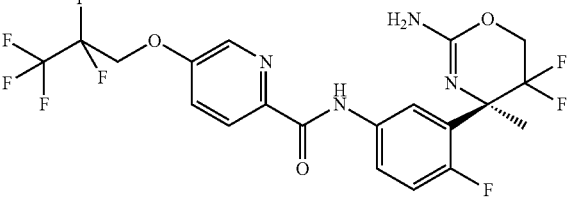 | 0.290 | 14.505 |
| 45 | 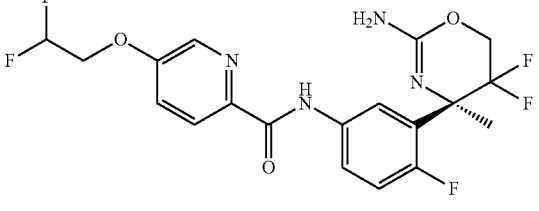 | 0.400 | 25.719 |
| 46 | 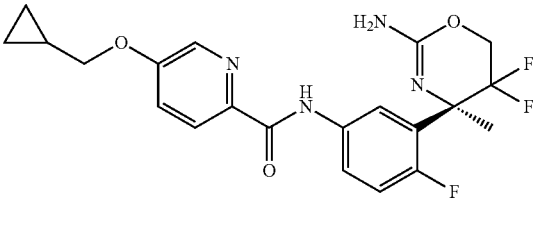 [SMILES: C[C@]1(c2cc(NC(=O)c3ccc(OCC4CC4)cn3)ccc2F)N=C(N)OCC1(F)F] | 0.070 | |
| 47 | 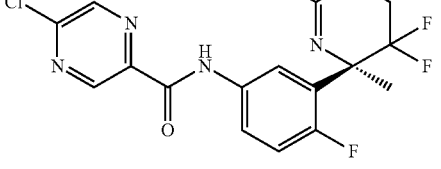 | 0.520 | 34.878 |
| 48 | 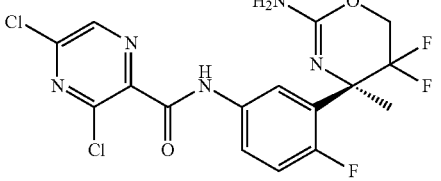 | 1.130 | 6.744 |

TABLE 1-continued

IC$_{50}$ values of selected examples

| Exam. | Structure | BACE1 cell act. Aβ40 IC$_{50}$ [μM] | BACE2 cell act. IC$_{50}$ [μM] |
|---|---|---|---|
| 49 | 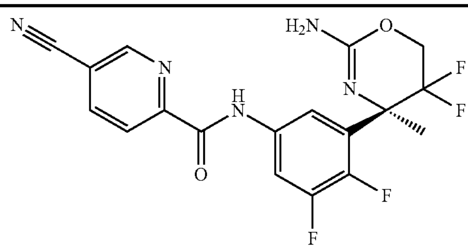 | 0.026 | 0.151 |
| 50 | 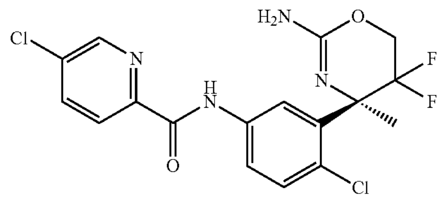 [SMILES: C[C@]1(c2cc(NC(=O)c3ccc(Cl)cn3)ccc2Cl)N=C(N)OCC1(F)F] | 0.017 | 0.024 |
| 51 | 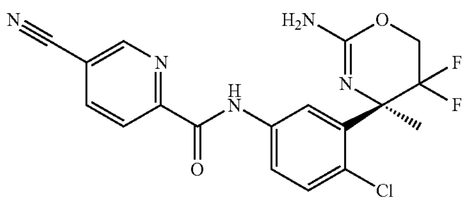 [SMILES: C[C@]1(c2cc(NC(=O)c3ccc(C#N)cn3)ccc2Cl)N=C(N)OCC1(F)F] | 0.020 | 0.327 |
| 52 | 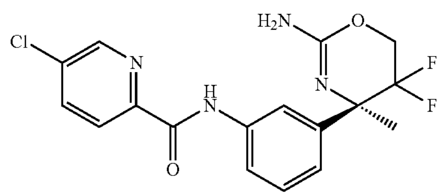 [SMILES: C[C@]1(c2cccc(NC(=O)c3ccc(Cl)cn3)c2)N=C(N)OCC1(F)F] | 0.009 | 0.035 |
| 53 | 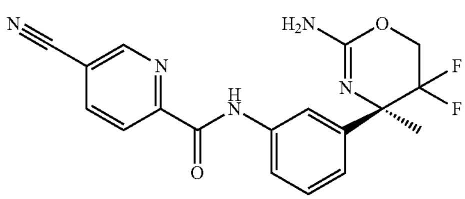 [SMILES: C[C@]1(c2cccc(NC(=O)c3ccc(C#N)cn3)c2)N=C(N)OCC1(F)F] | 0.013 | 0.349 |
| 54 | 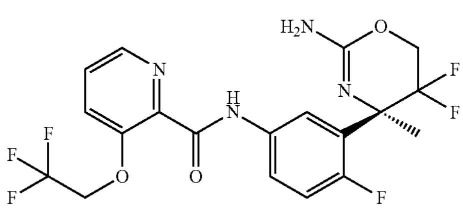 [SMILES: C[C@]1(c2cc(NC(=O)c3ncccc3OCC(F)(F)F)ccc2F)N=C(N)OCC1(F)F] | 0.635 | 0.245 |
| 55 | 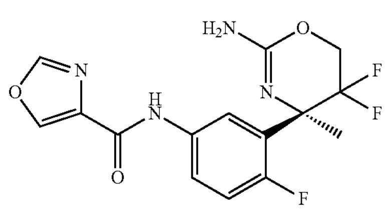 [SMILES: C[C@]1(c2cc(NC(=O)c3cocn3)ccc2F)N=C(N)OCC1(F)F] | 0.495 | |

TABLE 1-continued

IC$_{50}$ values of selected examples

| Exam. | Structure | BACE1 cell act. Aβ40 IC$_{50}$ [μM] | BACE2 cell act. IC$_{50}$ [μM] |
|---|---|---|---|
| 56 | 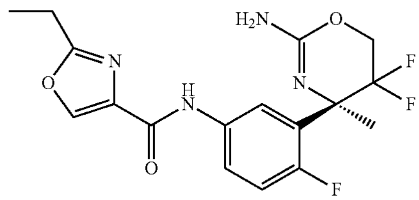 [SMILES: CCc1nc(C(=O)Nc2ccc(F)c([C@@]3(C)N=C(N)OCC3(F)F)c2)co1] | 0.140 | |
| 57 | 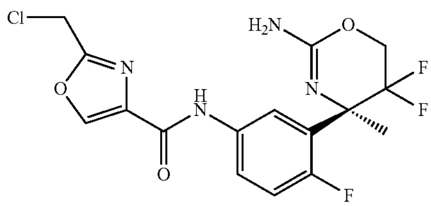 [SMILES: C[C@]1(c2cc(NC(=O)c3coc(CCl)n3)ccc2F)N=C(N)OCC1(F)F] | 0.073 | |
| 58 | 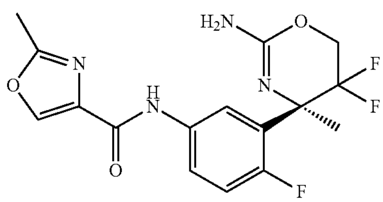 [SMILES: Cc1nc(C(=O)Nc2ccc(F)c([C@@]3(C)N=C(N)OCC3(F)F)c2)co1] | 0.015 | 0.025 |
| 59 | 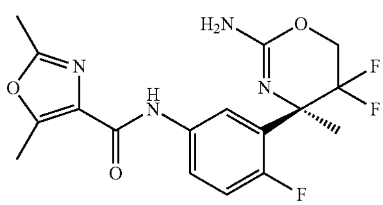 [SMILES: Cc1nc(C(=O)Nc2ccc(F)c([C@@]3(C)N=C(N)OCC3(F)F)c2)c(C)o1] | 0.043 | 0.097 |
| 60 | 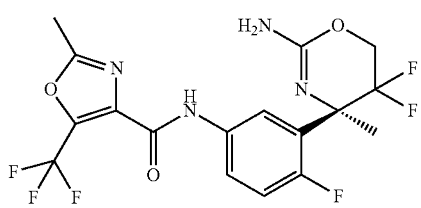 [SMILES: Cc1nc(C(=O)Nc2ccc(F)c([C@@]3(C)N=C(N)OCC3(F)F)c2)c(C(F)(F)F)o1] | 0.088 | 0.367 |
| 61 | 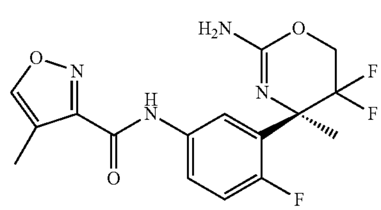 [SMILES: Cc1conc1C(=O)Nc1ccc(F)c([C@@]2(C)N=C(N)OCC2(F)F)c1] | 0.305 | |
| 63 | 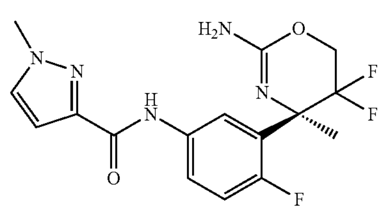 [SMILES: Cn1ccc(C(=O)Nc2ccc(F)c([C@@]3(C)N=C(N)OCC3(F)F)c2)n1] | 0.110 | 0.113 |

TABLE 1-continued

IC$_{50}$ values of selected examples

| Exam. | Structure | BACE1 cell act. Aβ40 IC$_{50}$ [μM] | BACE2 cell act. IC$_{50}$ [μM] |
|---|---|---|---|
| 64 | 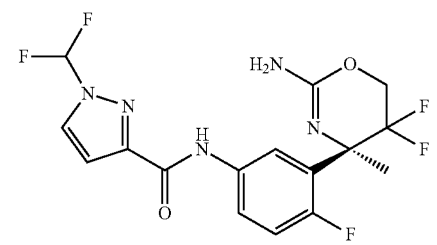 [SMILES: C[C@]1(c2cc(NC(=O)c3ccn(C(F)F)n3)ccc2F)N=C(N)OCC1(F)F] | 0.007 | 0.013 |
| 65 | 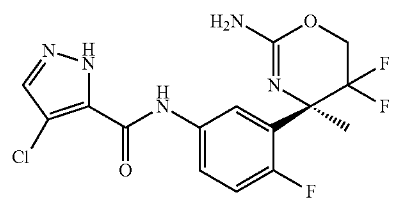 [SMILES: C[C@]1(c2cc(NC(=O)c3[nH]ncc3Cl)ccc2F)N=C(N)OCC1(F)F] | 0.404 | 0.543 |
| 66 | 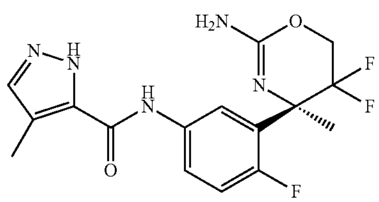 [SMILES: Cc1cn[nH]c1C(=O)Nc1ccc(F)c([C@@]2(C)N=C(N)OCC2(F)F)c1] | 0.622 | 0.465 |
| 68 | 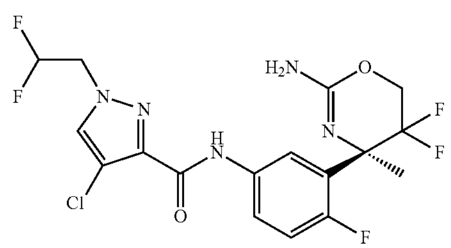 [SMILES: C[C@]1(c2cc(NC(=O)c3nn(CC(F)F)cc3Cl)ccc2F)N=C(N)OCC1(F)F] | 0.927 | 0.230 |
| 69 | 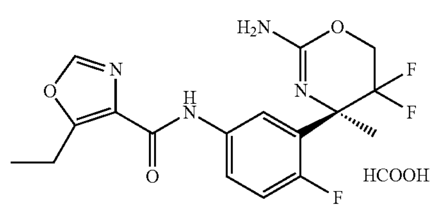 [SMILES: CCc1ocnc1C(=O)Nc1ccc(F)c([C@@]2(C)N=C(N)OCC2(F)F)c1 ; "HCOOH"] | 1.480 | |
| 71 | 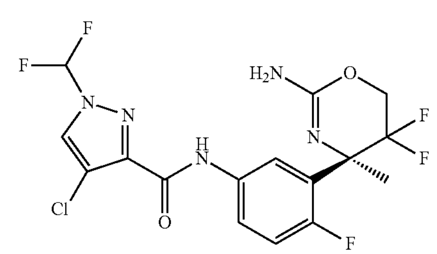 [SMILES: C[C@]1(c2cc(NC(=O)c3nn(C(F)F)cc3Cl)ccc2F)N=C(N)OCC1(F)F] | 0.007 | 0.030 |

TABLE 1-continued

IC$_{50}$ values of selected examples

| Exam. | Structure | BACE1 cell act. Aβ40 IC$_{50}$ [μM] | BACE2 cell act. IC$_{50}$ [μM] |
|---|---|---|---|
| 72 | 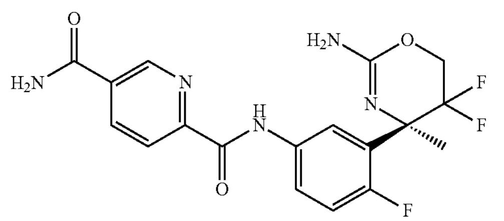 [SMILES: C[C@]1(c2cc(NC(=O)c3ccc(C(N)=O)cn3)ccc2F)N=C(N)OCC1(F)F] | 0.230 | |
| 73 | 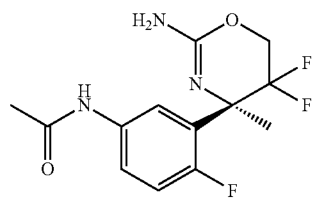 [SMILES: CC(=O)Nc1ccc(F)c([C@@]2(C)N=C(N)OCC2(F)F)c1] | 0.180 | |
| 74 | 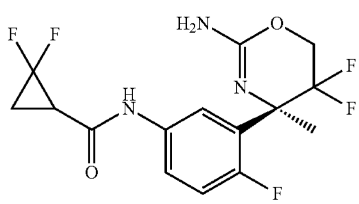 [SMILES: C[C@]1(c2cc(NC(=O)C3CC3(F)F)ccc2F)N=C(N)OCC1(F)F] | 0.510 | 0.590 |
| 75 | 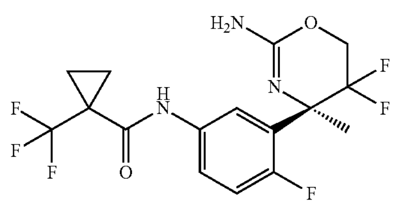 [SMILES: C[C@]1(c2cc(NC(=O)C3(C(F)(F)F)CC3)ccc2F)N=C(N)OCC1(F)F] | 1.490 | 1.010 |
| 76 | 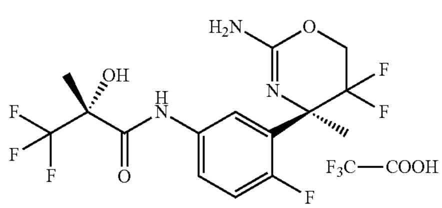 | 1.050 | 1.420 |
| 77 | 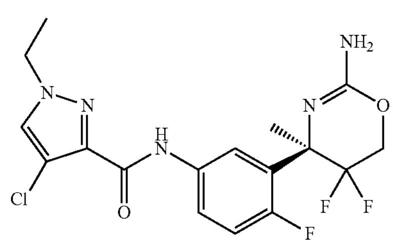 [SMILES: CCn1cc(Cl)c(C(=O)Nc2ccc(F)c([C@@]3(C)N=C(N)OCC3(F)F)c2)n1] | 0.100 | |

TABLE 1-continued

IC$_{50}$ values of selected examples

| Exam. | Structure | BACE1 cell act. Aβ40 IC$_{50}$ [μM] | BACE2 cell act. IC$_{50}$ [μM] |
|---|---|---|---|
| 78 | 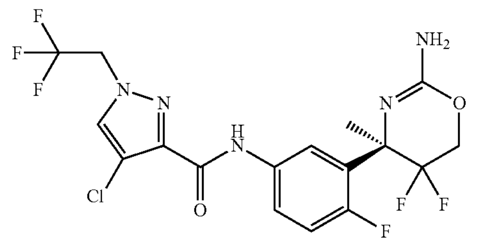 [SMILES: C[C@]1(c2cc(NC(=O)c3nn(CC(F)(F)F)cc3Cl)ccc2F)N=C(N)OCC1(F)F] | 1.77 | |
| 79 | 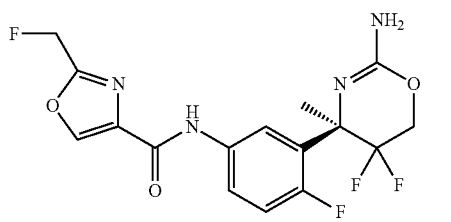 [SMILES: C[C@]1(c2cc(NC(=O)c3coc(CF)n3)ccc2F)N=C(N)OCC1(F)F] | 0.003 | |
| 81 | 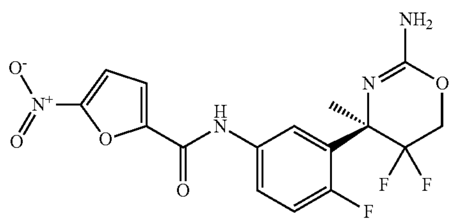 [SMILES: C[C@]1(c2cc(NC(=O)c3ccc([N+](=O)[O-])o3)ccc2F)N=C(N)OCC1(F)F] | 1.900 | |
| 82 | 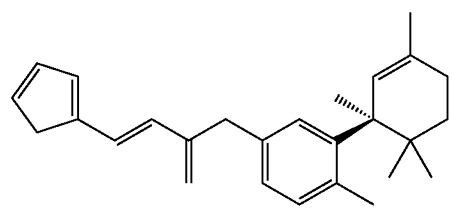 [SMILES: C=C(/C=C/C1=CC=CC1)Cc1ccc(C)c([C@@]2(C)C=C(C)CCC2(C)C)c1] | 0.910 | |
| 83 | 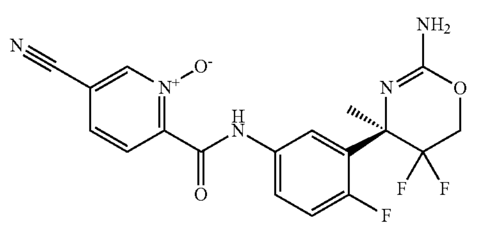 [SMILES: C[C@]1(c2cc(NC(=O)c3ccc(C#N)c[n+]3[O-])ccc2F)N=C(N)OCC1(F)F] | 0.310 | |

CYP Inhibition Assay

Inhibition of cytochromes P450 (CYPs) 2C9, 2D6 and 3A4 was assessed using human liver microsomes and CYP-selective substrate metabolism reactions. 50 μl incubations were made up containing (finally) 0.2 mg/ml pooled human liver microsomes, 5 μM substrate (diclofenac for CYP2C9 [4' hydroxylase], dextromethorphan for CYP2D6 [O-demethylase] or midazolam for CYP3A4 [1' hydroxylase]), 0.25 μL DMSO containing test inhibitor and NADPH regenerating system. Test inhibitor concentrations of 50, 16.7, 5.6, 1.9, 0.6 and 0.2 μM were assessed in singlicate. Incubations were prewarmed to 37° C. for 10 minutes before initiation by addition of NADPH regenerating system. Incubations were quenched after 5 minutes (20 minutes for dextromethorphan) by addition of 50 μl cold acetonitrile containing 20 ng/ml 4-OH-diclofenac-13C6, 20 ng/mL dextrorphan-D3 and 20 ng/mL 1-OH-midazolam-D4. Quenched incubates were stored at −20° C. for at least 1 hour before centrifugation (20,000×g, 20 minutes). Supernatants were removed and diluted 1:1 with water prior to analysis using a RapidFire sample injector system and API4000 mass spectrometer. Peak areas for substrate, metabolite and stable-labelled metabolite standard were determined using MS/MS. The peak area ratios between the metabolite generated by the enzymatic reaction and the internal standard were used in subsequent calculations. The percentage of (DMSO) control activity was calculated for each incubate and IC$_{50}$ values estimated by non-linear regression. Sulfaphenazole, quinidine or ketoconazole were tested in each CYP2C9, CYP2D6 or CYP3A4 inhibition experiment, respectively, to ensure assay sensitivity and reproducibility. (Validated assays for human cytochrome P450 activities, R. L. Walsky and R. S. Obach, Drug Metabolism and Disposition 32: 647-660, 2004. and S. Fowler and H. Zhang, The AAPS Journal, Vol. 10, No. 2, 410-424, 2008.)

PatchXpress hERG Inhibition Assay

The detailed method to quantify hERG channel inhibition by the automated patch clamp system PatchXpress® 7000A (Molecular Devices, Sunnyvale, Calif.) has been described by Guo et al. (Guo L, Guthrie H, Automated electrophysiology in the preclinical evaluation of drugs for potential QT prolongation. *Journal of Pharmacological & Toxicological Methods*, (2005) 52(1):123-35). In brief, Chinese hamster ovary (CHO) cells transfected with the human ether-a-go-go-related gene (hERG) was cultured in Ex-cell 302 media supplemented with 10% fetal bovine serum, 2 mM glutamine and 0.25 mg/ml geneticin and maintained in a CO$_2$ incubator at 37° C. For patch clamp electrophysiology, the external buffer contained (in mM): 150 NaCl, 10 Hepes, 4 KCl, 1.2 CaCl$_2$, 1 MgCl$_2$, pH 7.4 adjusted with HCl and the internal recording solution contained (in mM): 140 KCl, 6 EGTA, 5 Hepes, MgCl$_2$, 5 ATP-Na$_2$, pH 7.2 adjusted with KOH. Once the cell was loaded in the recording chamber and formed a giga ohm seal with the planar glass electrodes (Sealchip™), a whole-cell configuration was achieved by rupturing the cell membrane. The membrane potential was then clamped at −80 mV and the hERG channel activated by a 1-second depolarizing pulse delivered at 0.1 Hz, the hERG current was measured during the 500 ms-repolarizing pulse to −40 mV. After an acceptable hERG current recording was obtained, the cell was first exposed to 0.3% DMSO as the vehicle control, followed by the test article in three ascending, full-log interval concentrations and finally E-4031 at 1 µM (as the positive control) to block the hERG current completely. Each test article was tested on three or more cells and at concentrations up to 30 µM or the solubility limit determined the BD Gentest™ solubility scanner. The inhibition of hERG current at each concentration was normalized to that recorded in the vehicle control, and fitted with Hill equation to calculate IC$_{20}$ and/or IC$_{50}$.

Cathepsin D and Cathepsin E Fluorescent Substrate Kinetic Assays

General Assay Principle

The MR121 fluorescence assays described below are based on the fact that MR121 forms a non-fluorescent ground state complex with tryptophan. In solution this formation occurs at millimolar concentrations of tryptophan. The mechanism can be used to design a generic biochemical assay for proteases. A substrate peptide is labeled at the N-terminus with tryptophan and at the C-terminus with the fluorophore MR121 (for cathepsin D the 10 amino acid peptide WTSVLMAAPC-MR121 was used; for cathepsin E, MR121-CKLVFFAEDW was used). In absence of protease activity, the substrates remain intact and the MR121 fluorescence is reduced by the high local Trp-concentration. If the substrates are cleaved by the enzymes the MR121 fluorescence is recovered.

Assay Procedure

The fluorescent substrate cathepsin D and cathepsin E kinetic assays were performed at room temperature in 384-well microtiter plates (black with clear flat bottom, non binding surface plates from Corning) in a final volume of 51 µl. The test compounds were serially diluted in DMSO (15 concentrations, 1/3 dilution steps) and 1 µl of diluted compounds were mixed for 10 min with 40 µl of cathepsin D (from human liver, Calbiochem) diluted in assay buffer (100 mM sodium acetate, 0.05% BSA, pH 5.5; final concentration: 200 nM) or with 40 µl of recombinant human cathepsin E (R&D Systems) diluted in assay buffer (100 mM sodium acetate, 0.05% BSA, pH 4.5; final concentration: 0.01 nM). After addition of 10 µl of the cathepsin D substrate WTSVLMAAPC-MR121 diluted in cathepsin D assay buffer (final concentration: 300 nM) or 10 l of the cathepsin E substrate MR121-CKLVF-FAEDW diluted in cathepsin E assay buffer (final concentration: 300 nM), the plates were strongly shaken for 2 minutes. The enzymatic reaction was followed in a plate: vision reader (Perkin Elmer) (excitation wavelength: 630 nm; emission: 695 nm) for at least 30 minutes in a kinetic measurement detecting an increase of MR121 fluorescence during the reaction time. The slope in the linear range of the kinetic was calculated and the IC$_{50}$ of the test compounds were determined using a four parameter equation for curve fitting.

TABLE 2 biological data of selected examples

| Ex. | P-gP human [1] | GSH human [2] | hERG | in vivo effect [4] | Cathepsin E IC$_{50}$ [µM] | Cathepsin D IC$_{50}$ [µM] | CYP IC$_{50}$ [µM] [5] | | |
|---|---|---|---|---|---|---|---|---|---|
| | | | | | | | 3A4 | 2D6 | 2C9 |
| 1 | A | — | A | A | 109 | >200 | A | B | A |
| 5 | A | NF | A | A | >200 | >200 | A | B | — |
| 8 | A | — | A | A | >160 | >170 | A | A | A |
| 11 | A | NF | A | A | 73 | 69 | A | A | A |
| 20 | A | — | A | A | >200 | >200 | A | B | B |
| 21 | A | — | — | A | >200 | >200 | A | A | A |
| 22 | — | — | — | A | >200 | >200 | B | B | A |
| 39 | — | — | — | A | >200 | >200 | B | A | A |

[1] Efflux ratio: substrate category: A = not or weak substrate.
[2] NF = in vitro no significant adduct formation relative to control.
[3] A = less than 26% inhibition @ 1 µM.
[4] A = less than 50% of control @ 30 mg/kg p.o.
[5] A = IC$_{50}$ > 10 µM ; B = 1 µM < IC$_{50}$ < 10 µM; C = IC$_{50}$ < 1 µM Pharmaceutical Compositions The compounds of formula I and the pharmaceutically acceptable salts can be used as therapeutically active substances, e.g. in the form of pharmaceutical compositions. The pharmaceutical compositions can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injection solutions.

The compounds of formula I and the pharmaceutically acceptable salts thereof can be processed with pharmaceutically inert, inorganic or organic carriers for the production of pharmaceutical compositions. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain pharmaceutically acceptable auxiliary substances such as preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The invention further provides pharmaceutical compositions containing a compound of formula I or a pharmaceutically acceptable salt thereof and a therapeutically inert carrier, and a process for their production, which comprises bringing one or more compounds of formula I and/or pharmaceutically acceptable salts thereof and, if desired, one or more other therapeutically valuable substances into a galenical administration form together with one or more therapeutically inert carriers.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically acceptable salt thereof. The daily dosage can be administered as single dose or in divided doses and, in addition, the upper limit can also be exceeded when this is found to be indicated.

The following examples illustrate the present invention without limiting it, but serve merely as representative thereof. The pharmaceutical preparations conveniently contain about 1-500 mg, preferably 1-100 mg, of a compound of formula I. Examples of compositions according to the invention are:

EXAMPLE A

Tablets of the following composition are manufactured in the usual manner:

TABLE 3 possible tablet composition

| ingredient | mg/tablet | | | |
|---|---|---|---|---|
| | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure
1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

EXAMPLE B-1

Capsules of the following composition are manufactured:

TABLE 4 possible capsule ingredient composition

| ingredient | mg/capsule | | | |
|---|---|---|---|---|
| | 5 | 25 | 100 | 500 |
| Compound of formula I | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure
1. Mix ingredients 1, 2 and 3 in a suitable mixer for 30 minutes.
2. Add ingredients 4 and 5 and mix for 3 minutes.
3. Fill into a suitable capsule.

The compound of formula I, lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

EXAMPLE B-2

Soft Gelatin Capsules of the following composition are manufactured:

TABLE 5 possible soft gelatin capsule ingredient composition

| ingredient | mg/capsule |
|---|---|
| Compound of formula I | 5 |
| Yellow wax | 8 |
| Hydrogenated Soya bean oil | 8 |
| Partially hydrogenated plant oils | 34 |
| Soya bean oil | 110 |
| Total | 165 |

TABLE 6

| possible soft gelatin capsule composition | |
|---|---|
| ingredient | mg/capsule |
| Gelatin | 75 |
| Glycerol 85% | 32 |
| Karion 83 | 8 (dry matter) |
| Titan dioxide | 0.4 |
| Iron oxide yellow | 1.1 |
| Total | 116.5 |

Manufacturing Procedure

The compound of formula I is dissolved in a warm melting of the other ingredients and the mixture is filled into soft gelatin capsules of appropriate size. The filled soft gelatin capsules are treated according to the usual procedures.

EXAMPLE C

Suppositories of the following composition are manufactured:

TABLE 7

| possible suppository composition | |
|---|---|
| ingredient | mg/supp. |
| Compound of formula I | 15 |
| Suppository mass | 1285 |
| Total | 1300 |

Manufacturing Procedure

The suppository mass is melted in a glass or steel vessel, mixed thoroughly and cooled to 45° C. Thereupon, the finely powdered compound of formula I is added thereto and stirred until it has dispersed completely. The mixture is poured into suppository moulds of suitable size, left to cool; the suppositories are then removed from the moulds and packed individually in wax paper or metal foil.

EXAMPLE D

Injection solutions of the following composition are manufactured:

TABLE 8

| possible injection solution composition | |
|---|---|
| ingredient | mg/injection solution. |
| Compound of formula I | 3 |
| Polyethylene Glycol 400 | 150 |
| acetic acid | q.s. ad pH 5.0 |
| water for injection solutions | ad 1.0 ml |

Manufacturing Procedure

The compound of formula I is dissolved in a mixture of Polyethylene Glycol 400 and water for injection (part). The pH is adjusted to 5.0 by acetic acid. The volume is adjusted to 1.0 ml by addition of the residual amount of water. The solution is filtered, filled into vials using an appropriate overage and sterilized.

EXAMPLE E

Sachets of the following composition are manufactured:

TABLE 9

| possible sachet composition | |
|---|---|
| ingredient | mg/sachet |
| Compound of formula I | 50 |
| Lactose, fine powder | 1015 |
| Microcrystalline cellulose (AVICEL PH 102) | 1400 |
| Sodium carboxymethyl cellulose | 14 |
| Polyvinylpyrrolidon K 30 | 10 |
| Magnesium stearate | 10 |
| Flavoring additives | 1 |
| Total | 2500 |

Manufacturing Procedure

The compound of formula I is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

Experimental Part

The following examples are provided for illustration of the invention. They should not be considered as limiting the scope of the invention, but merely as being representative thereof.

Synthesis of the Intermediate 1-(2-fluoro-5-nitro-phenyl)-propan-1-one XII-1

To a solution of the 1-(2-fluoro-phenyl)-propan-1-one (99 mmol) in concentrated sulfuric acid (80 ml) cooled down to −30° C. was added slowly fuming nitric acid (8 ml) over 20 min and the solution was stirred at −30° C. for 15 min. The mixture was slowly poured into a stirred mixture of 200 ml of water and 400 g of ice. The aqueous phase was extracted with ethyl acetate, the organic layer was extracted again with water and aqueous 1 M $NaHCO_3$-solution. The organic layer was dried over $Na_2SO_4$, evaporated and the residue was chromatographed on silica using a mixture of heptane and ethylacetate as eluent to afford 16.5 g of the pure nitro intermediate XII-1. MS (ESI): m/z=198.1 $[M+H]^+$.

Synthesis of the Intermediate 1-(2,3-difluoro-5-nitro-phenyl)-ethanone XII-2

Under an inert atmosphere of nitrogen 1-(2,3-difluoro-phenyl)-ethanone (5.0 g (32 mmol) was added dropwise to sulphuric acid (95-97%, 20 ml), cooled to 0° C., at such a rate that the temperature was maintained below 5° C. Thereafter, the reaction mixture was cooled to −15° C. and a solution of nitric acid (3.22 ml, 46.4 mmol) in sulphuric acid (95-97%, 4.6 ml) was added dropwise at −15° C. After stirring at −10° C. for 45 minutes, the mixture was poured on ice. Ethyl acetate was added, then the organic layer separated, washed with water, dried over sodium sulphate, and evaporated at reduced pressure. Purification of the crude light yellow oil (5.64 g) by chromatography on silica gel using a gradient of heptane/ethyl acetate=100:0 to 0:100 yielded the 1-(2,3-difluoro-5-nitro-phenyl)-ethanone (1.83 g, 28% of theory) as a light yellow oil together with a mixture of 1-(2,3-difluoro-5-nitro-phenyl)-ethanone and 1-(2,3-difluoro-6-nitro-phenyl)-ethanone.

General Procedure A: Synthesis of the Intermediate Sulfinyl Imines VI and XVI

To a solution of the (R)-(+)-tert-butylsulfinamide (89.8 mmol) in THF (400 ml) was added subsequently the ketone (98.7 mmol) and titanium(IV) ethoxide (178.4 mmol) and the solution was stirred at reflux temperature for 3 to 18 h. The mixture was cooled to 22° C., treated with brine (400 ml); the suspension was stirred for 10 min and filtered over dicalite. The layers were separated, the aqueous layer was extracted with ethyl acetate, the combined organic layers were washed with water, dried and evaporated. The residue was chromatographed on silica using a mixture of heptane and ethyl acetate as eluent to give the pure sulfinyl imines VI or XVI.

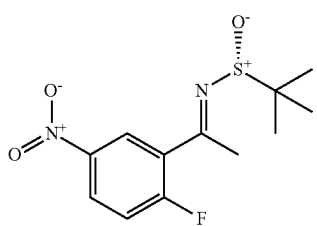 [SMILES: C/C(=N\[S@+]([O-])C(C)(C)C)c1cc([N+](=O)[O-])ccc1F]

Intermediate VI-2 ($R^2$=F; $R^3$=Me): Starting from 1-(2-fluoro-5-nitro-phenyl)-ethanone (89.7 mmol), the product (R)-2-methyl-propane-2-sulfinic acid [1-(2-fluoro-5-nitro-phenyl)-(E)-ethylidene]-amide (21.56 g) was obtained as a pale yellow solid. MS (ISP): m/z=287.0 $[M+H]^+$.

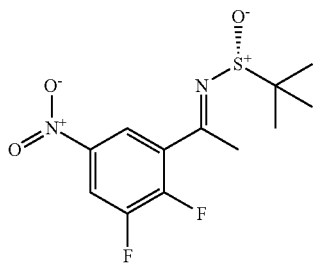 [SMILES: C/C(=N\[S@+]([O-])C(C)(C)C)c1cc([N+](=O)[O-])cc(F)c1F]

Intermediate VI-3 ($R^{2a}$ and $R^{2b}$=F; $R^3$=Me): Starting from 1-(2,3-difluoro-5-nitro-phenyl)-ethanone (19.9 mmol), the product (R)-2-methyl-propane-2-sulfinic acid [1-(2,3-difluoro-5-nitro-phenyl)-(E)-ethylidene]-amide (5.27 g) was obtained as a light yellow solid. MS (ISP): m/z=305.1 $[M+H]^+$.

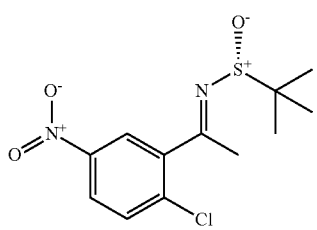 [SMILES: C/C(=N\[S@+]([O-])C(C)(C)C)c1cc([N+](=O)[O-])ccc1Cl]

Intermediate VI-4 ($R^2$=Cl; $R^3$=Me): Starting from 1-(2-chloro-5-nitro-phenyl)-ethanone (75.2 mmol), the product (R)-2-methyl-propane-2-sulfinic acid [1-(2-chloro-5-nitro-phenyl)-eth-(E)-ylidene]-amide (16.26 g) was obtained as a light yellow solid. MS (ISP): m/z=303.1 $[M+H]^+$.

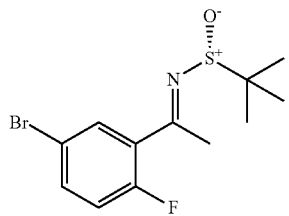 [SMILES: C/C(=N\[S@+]([O-])C(C)(C)C)c1cc(Br)ccc1F]

Intermediate VI-1 ($R^2$=F; $R^3$=Me): Starting from 1-(5-bromo-2-fluoro-phenyl)-ethanone (241 mmol), the product (R)-2-methyl-propane-2-sulfinic acid [1-(5-bromo-2-fluoro-phenyl)-(E)-ethylidene]-amide (63.6 g) was obtained as a light yellow solid. MS (ISP): m/z=320.0 $[M+H]^+$ and 322.0 $[M+2+H]^+$.

General Procedure B: Synthesis of the Intermediate Sulfinamide Difluoroesters VII and XVII In a dry apparatus a suspension of freshly activated zinc powder (1.28 g, 19.6 mmol) in dry diethyl ether (45 ml) was heated under inert atmosphere to reflux. A solution of the sulfinyl imine VI or XVI (3.14 g, 9.81 mmol) and ethyl 2-bromo-2,2-difluoroacetate (3.98 g, 2.52 ml, 19.6 mmol) in dry diethyl ether (25 ml) was added dropwise over a period of 15 minutes while internal temperature rose from 34° C. to 35° C. and reflux increased. The suspension was held at reflux for further 5 h, cooled to 23° C., filtered through celite and washed with ethyl acetate. The filtrate was poured into 300 mL sat $NH_4Cl$-solution and extracted with ethyl acetate (2×300 ml). The combined organic layers were dried over $Na_2SO_4$ and evaporated to give 4.59 g crude product as a brown oil, which was purified by flash chromatography (silica gel, 70 g) with heptane/ethyl acetate 8:1 to give the sulfinamide difluoroesters VII or XVII.

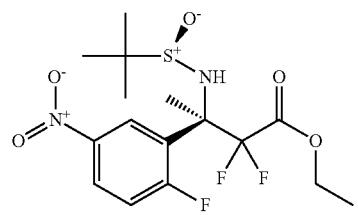 [SMILES: CCOC(=O)C(F)(F)[C@](C)(N[S@+]([O-])C(C)(C)C)c1cc([N+](=O)[O-])ccc1F]

Intermediate VII-1 ($R^2$=F; $R^3$=Me): Starting from (R)-2-methyl-propane-2-sulfinic acid [1-(2-fluoro-5-nitro-phenyl)-(E)-ethylidene]-amide (intermediate VI-1) (5.73 g, 20 mmol), the product (R)-2,2-difluoro-3-(2-fluoro-5-nitro-phenyl)-3-((R)-2-methyl-propane-2-sulfinylamino)-butyric acid ethyl ester (3.1 g) was obtained as an orange oil. MS (ISP): m/z=411.2 $[M+H]^+$.

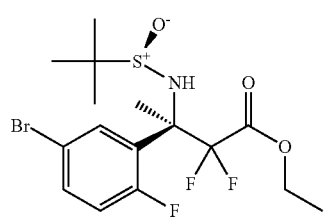 [SMILES: CCOC(=O)C(F)(F)[C@](C)(N[S@+]([O-])C(C)(C)C)c1cc(Br)ccc1F]

Intermediate XVII-1 ($R^2$=F; $R^3$=Me): Starting from (R)-2-methyl-propane-2-sulfinic acid [1-(5-bromo-2-fluoro-phenyl)-(E)-ethylidene]-amide (intermediate XVI-1) (9.8 mmol), the product (R)-3-(5-bromo-2-fluoro-phenyl)-2,2-difluoro-3-((R)-2-methyl-propane-2-sulfinylamino)-butyric acid ethyl ester (3.08 g) was obtained as an orange oil. MS (ISP): m/z=444.1 [M+H]$^+$ and 446.1 [M+2+H]$^+$.

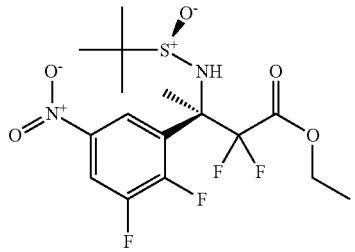 [SMILES: CCOC(=O)C(F)(F)[C@](C)(N[S@+]([O-])C(C)(C)C)c1cc([N+](=O)[O-])cc(F)c1F]

Intermediate VII-2 ($R^{2a}$ and $R^{2b}$=F; $R^3$=Me): Starting from (R)-2-methyl-propane-2-sulfinic acid [1-(2,3-difluoro-5-nitro-phenyl)-(E)-ethylidene]-amide (intermediate VI-3) (1.64 mmol), the product (R)-2,2-difluoro-3-(2,3-difluoro-5-nitro-phenyl)-3-((R)-2-methyl-propane-2-sulfinylamino)-butyric acid ethyl ester (340 mg) was obtained as a light yellow oil. MS (ISP): m/z=429.1 [M+H]$^+$.

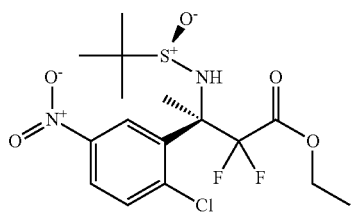

Intermediate VII-3 ($R^2$=Cl; $R^3$=Me): Starting from (R)-2-methyl-propane-2-sulfinic acid [1-(2-chloro-5-nitro-phenyl)-eth-(E)-ylidene]-amide (6.6 mol), the product (R)-2,2-difluoro-3-(2-chloro-5-nitro-phenyl)-3-(R)-2-methyl-propane-2-sulfinylamino)-butyric acid ethyl ester (1.69 g) was obtained as an orange oil. MS (ISP): m/z=427.0 [M+H]$^+$.

General Procedure C1: Synthesis of the Intermediate Sulfinamide Alcohols VIII and XVIII ($R^4$ and $R^5$=H)

A solution of the sulfinamide difluoroesters VII or XVII (4.4 mmol) in dry THF (24 ml) was cooled down to 0° C. was treated with lithium borohydride (9.0 mmol) and stirring was continued at 0° C. for 15 min. The reaction mixture was then let to warm up to room temperature and stirred for an additional 2 to 18 h. The reaction was quenched by addition of water, reaction volume was reduced in vacuo and diluted with ethylacetate. The organic phase was washed with brine, dried over Na$_2$SO$_4$ and evaporated to give a residue which was chromatographed on silica using a mixture of n-heptane and ethyl acetate as eluent to give the intermediate amino esters VIII or XVIII.

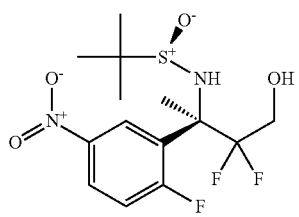

Intermediate VIII-1 ($R^2$=F; $R^3$=Me): Starting from (R)-2,2-difluoro-3-(2-fluoro-5-nitro-phenyl)-3-((R)-2-methyl-propane-2-sulfinylamino)-butyric acid ethyl ester (intermediate VI-1) (3.78 g, 9.2 mmol), the product (R)-2-methyl-propane-2-sulfinic acid [(R)-2,2-difluoro-1-(2-fluoro-5-nitro-phenyl)-3-hydroxy-1-methyl-propyl]-amide (2.9 g) was obtained as a light yellow solid. MS (ISP): m/z=369.0 [M+H]$^+$.

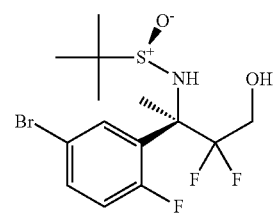 [SMILES: CC(C)(C)[S@@+]([O-])N[C@](C)(c1cc(Br)ccc1F)C(F)(F)CO]

Intermediate XVIII-1 ($R^2$=F; $R^3$=Me; $R^4$ and $R^5$=H): Starting from (R)-3-(5-bromo-2-fluoro-phenyl)-2,2-difluoro-3-((R)-2-methyl-propane-2-sulfinylamino)-butyric acid ethyl ester (intermediate XVII-1) (5.95 g, 13 mmol), the product (R)-2-methyl-propane-2-sulfinic acid [(R)-1-(5-bromo-2-fluoro-phenyl)-2,2-difluoro-3-hydroxy-1-methyl-propyl]-amide (5.3 g) was obtained as a yellow oil. MS (ISP): m/z=402.2 [M+H]$^+$ and 404.2 [M+2+H]$^+$.

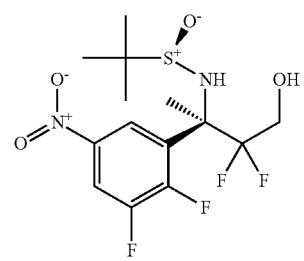 [SMILES: CC(C)(C)[S@@+]([O-])N[C@](C)(c1cc([N+](=O)[O-])cc(F)c1F)C(F)(F)CO]

Intermediate VIII-2 ($R^{2a}$ and $R^{2b}$=F; $R^3$=Me): Starting from (R)-2,2-difluoro-3-(2,3-difluoro-5-nitro-phenyl)-3-(R)-2-methyl-propane-2-sulfinylamino)-butyric acid ethyl ester (intermediate VII-2) (0.8 mmol), the product (R)-2-methyl-propane-2-sulfinic acid [(R)-2,2-difluoro-1-(2,3-difluoro-5-nitro-phenyl)-3-hydroxy-1-methyl-propyl]-amide (179 mg) was obtained as an off-white solid. MS (ISP): m/z=387.1 [M+H]$^+$.

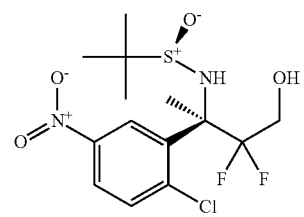

Intermediate VIII-3 ($R^2$=Cl; $R^3$=Me): Starting from (R)-2,2-difluoro-3-(2-chloro-5-nitro-phenyl)-3-(R)-2-methyl-propane-2-sulfinylamino)-butyric acid ethyl ester (2.34 mmol), the product (R)-2-methyl-propane-2-sulfinic acid [(R)-2,2-difluoro-1-(2-chloro-5-nitro-phenyl)-3-hydroxy-1-methyl-propyl]-amide (721 mg) was obtained as an off-white solid. MS (ISP): m/z=385.0 [M+H]$^+$.

General Procedure C2: Synthesis of the Intermediate Sulfinamide Alcohols XVIII ($R^4$ and $R^5$=Lower Alkyl)

A solution of the (R)-3-(5-bromo-2-fluoro-phenyl)-2,2-difluoro-3-((R)-2-methyl-propane-2-sulfinylamino)-butyric acid ethyl ester (intermediate XVII-1) (1.55 g, 3.5 mmol) in dry THF (60 ml) was cooled to −78° C., then a solution of the alkylmagnesium halide (here e.g. methylmagnesium bromide (3 M in diethyl ether, 11.6 ml, 34.9 mmol)) was dropwise added and stirring was continued −78° C. for 4 h, followed by warming up to 23° C. and stirring for another 18 h. The reaction mixture was poured into sat. $NH_4Cl$-solution, extracted with ethyl acetate, the organic layer was washed with brine and dried over $Na_2SO_4$, filtered and the solvent was evaporated totally to give the product (1.29 g, 86%) as light yellow oil.

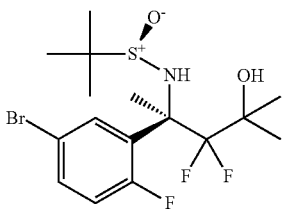 [SMILES: CC(C)(C)[S@@+]([O-])N[C@](C)(c1cc(Br)ccc1F)C(F)(F)C(C)(C)O]

Intermediate XVIII-2 ($R^2$=F; $R^3$, $R^4$ and $R^5$=Me): Starting from (R)-3-(5-bromo-2-fluoro-phenyl)-2,2-difluoro-3-((R)-2-methyl-propane-2-sulfinylamino)-butyric acid ethyl ester (intermediate XVII-1) (1.55 g, 3.5 mmol), the product (R)-2-methyl-propane-2-sulfinic acid [(R)-1-(5-bromo-2-fluoro-phenyl)-2,2-difluoro-3-hydroxy-1,3-dimethyl-butyl]-amide (1.29 g) was obtained as a light yellow oil. MS (ISN): m/z=427.9 $[M+H]^+$ and 429.9 $[M+2+H]^+$.

General Procedure D: Synthesis of the Intermediate Amino Alcohols IX and XIX

A solution of the sulfinamide alcohols VIII or XVIII (10.3 mmol) in methanol or THF (30 to 60 ml) was treated with a solution of HCl in 1,4-dioxane (4 M, 10-13 ml) and stirring was continued at 23° C. for 2 to 18 h. The mixture was partitioned between ethyl acetate and aqueous 2 M $Na_2CO_3$-solution, the organic layer was dried over $Na_2SO_4$, filtered and evaporated to give a residue which was chromatographed on silica using a mixture of n-heptane and ethyl acetate as eluent to give the pure aminoalcohols IX or XIX.

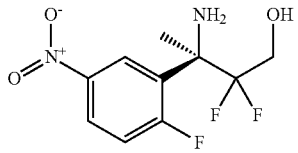

Intermediate XIX-1 ($R^2$=F; $R^3$=Me): Starting from (R)-2-methyl-propane-2-sulfinic acid [(R)-2,2-difluoro-1-(2-fluoro-5-nitro-phenyl)-3-hydroxy-1-methyl-propyl]-amide (intermediate C1) (3.79 g, 10.3 mmol), the product (R)-3-amino-2,2-difluoro-3-(2-fluoro-5-nitro-phenyl)-butan-1-ol (2.5 g) was obtained as a light yellow solid. MS (ISP): m/z=265.1 $[M+H]^+$.

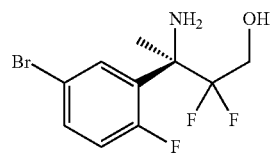 [SMILES: C[C@@](N)(c1cc(Br)ccc1F)C(F)(F)CO]

Intermediate XIX-1 ($R^2$=F; $R^3$=Me; $R^4$ and $R^5$=H): Starting from [(R)-1-(5-bromo-2-fluoro-phenyl)-2,2-difluoro-3-hydroxy-1-methyl-propyl]-amide (intermediate XVIII-1) (7.1 g, 17.7 mmol), the product (R)-3-amino-3-(5-bromo-2-fluoro-phenyl)-2,2-difluoro-butan-1-ol (4.75 g) was obtained as a light brown oil. MS (ISP): m/z=298.2 $[M+H]^+$ and 300.2 $[M+2+H]^+$.

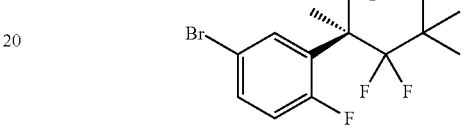

Intermediate XIX-2 ($R^2$=F; $R^3$, $R^4$ and $R^5$=Me): Starting from (R)-2-methyl-propane-2-sulfinic acid [(R)-1-(5-bromo-2-fluoro-phenyl)-2,2-difluoro-3-hydroxy-1,3-dimethyl-butyl]-amide (intermediate XVIII-2) (2.9 g, 6.7 mmol), the product (R)-4-amino-4-(5-bromo-2-fluoro-phenyl)-3,3-difluoro-2-methyl-pentan-2-ol (1.44 g) was obtained as a white solid. MS (ISP): m/z=326.2 $[M+H]^+$ and 328.2 $[M+2+H]^+$.

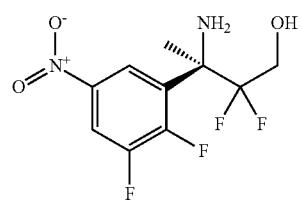 [SMILES: C[C@@](N)(c1cc([N+](=O)[O-])cc(F)c1F)C(F)(F)CO]

Intermediate IX-2 ($R^{2a}$ and $R^{2b}$=F; $R^3$=Me): Starting from (R)-2-methyl-propane-2-sulfinic acid [(R)-2,2-difluoro-1-(2,3-difluoro-5-nitro-phenyl)-3-hydroxy-1-methyl-propyl]-amide, the product (R)-3-amino-3-(2,3-difluoro-5-nitro-phenyl)-2,2-difluoro-butan-1-ol (116 mg) was obtained as a light yellow oil. MS (ISP): m/z=283.1 $[M+H]^+$.

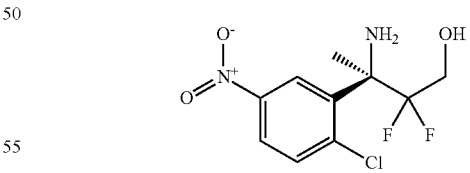

Intermediate IX-3 ($R^2$=Cl; $R^3$=Me): Starting from (R)-2-methyl-propane-2-sulfinic acid [(R)-2,2-difluoro-1-(2-chloro-5-nitro-phenyl)-3-hydroxy-1-methyl-propyl]-amide (1.87 mmol), the product (R)-3-amino-3-(2-chloro-5-nitro-phenyl)-2,2-difluoro-butan-1-ol (455 mg) was obtained as a light yellow solid. MS (ISP): m/z=281.1 $[M+H]^+$.

General Procedure E: Synthesis of the Intermediate Amino Oxazines X and XX

To a solution of the amino alcohols IX or XIX (8.4 mmol) in ethanol (40 ml) at 23° C. was added under argon cyanogen bromide (1.33 g, 12.6 mmol) and the light yellow reaction solution was stirred in a sealed tube for 24 hours at 85° C. Cooled to 23° C., some ice was added to the reaction mixture was added some ice, followed by extraction with DCM/water/sat, NaHCO$_3$-sol. solution (pH=8). The organic layer was dried over Na$_2$SO$_4$, filtered and evaporated to give the crude product, which was either used in the next step without further purification or purified by chromatography on silica gel using a mixture of n-heptane and ethyl acetate as eluent to afford pure amino oxazine X or XX.

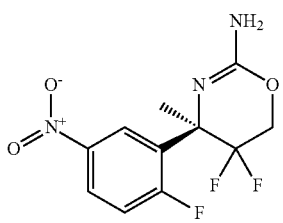 [SMILES: C[C@]1(c2cc([N+](=O)[O-])ccc2F)N=C(N)OCC1(F)F]

Intermediate X-1 (R$^2$=F; R$^3$=Me): Starting from (R)-3-amino-2,2-difluoro-3-(2-fluoro-5-nitro-phenyl)-butan-1-ol (intermediate D1) (1.5 g, 5.7 mmol), the product (R)-5,5-difluoro-4-(2-fluoro-5-nitro-phenyl)-4-methyl-5,6-dihydro-4H-[1,3]oxazin-2-ylamine (1.3 g) was obtained as a light yellow solid. MS (ISP): m/z=290.2 [M+H]$^+$.

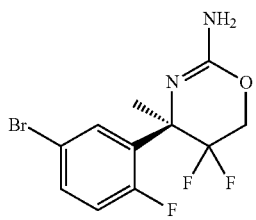 [SMILES: C[C@]1(c2cc(Br)ccc2F)N=C(N)OCC1(F)F]

Intermediate XX-1 (R$^2$=F; R$^3$=Me; R$^4$ and R$^5$=H): Starting from (R)-3-amino-3-(5-bromo-2-fluoro-phenyl)-2,2-difluoro-butan-1-ol (intermediate XIX-1) (2.5 g, 8.4 mmol), the product (R)-4-(5-bromo-2-fluoro-phenyl)-5,5-difluoro-4-methyl-5,6-dihydro-4H-[1,3]oxazin-2-ylamine (2.36 g) was obtained as a light yellow oil. MS (ISP): m/z=323.1 [M+H]$^+$ and 325.1 [M+2+H]$^+$.

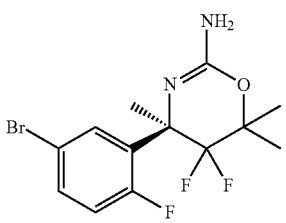 [SMILES: CC1(C)OC(N)=N[C@](C)(c2cc(Br)ccc2F)C1(F)F]

Intermediate XX-2 (R$^2$=F; R$^3$, R$^4$ and R$^5$=Me): Starting from (R)-4-amino-4-(5-bromo-2-fluoro-phenyl)-3,3-difluoro-2-methyl-pentan-2-ol (intermediate XIX-2) (0.76 g, 2.3 mmol), the product (R)-4-(5-bromo-2-fluoro-phenyl)-5,5-difluoro-4,6,6-trimethyl-5,6-dihydro-4H-[1,3]oxazin-2-ylamine (0.77 g) was obtained as a colorless oil. MS (ISP): m/z=351.1 [M+H]$^+$ and 353.1[M+2+H]$^+$.

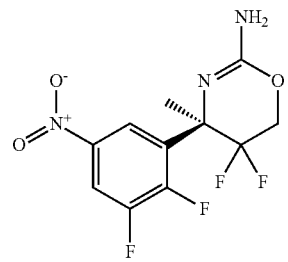 [SMILES: C[C@]1(c2cc([N+](=O)[O-])cc(F)c2F)N=C(N)OCC1(F)F]

Intermediate X-2 (R$^{2a}$ and R$^{2b}$=F; R$^3$=Me): Starting from (R)-3-amino-3-(2,3-difluoro-5-nitro-phenyl)-2,2-difluoro-butan-1-ol (0.41 mmol) (intermediate IX-2), the product (R)-5,5-difluoro-4-(2,3-difluoro-5-nitro-phenyl)-4-methyl-5,6-dihydro-4H-[1,3]oxazin-2-ylamine (100 mg) was obtained as a light yellow oil. MS (ISP): m/z=308.1 [M+H]$^+$.

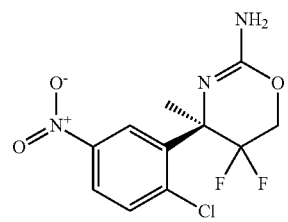 [SMILES: C[C@]1(c2cc([N+](=O)[O-])ccc2Cl)N=C(N)OCC1(F)F]

Intermediate X-3 (R$^2$=Cl; R$^3$=Me): Starting from (R)-3-amino-3-(2-chloro-5-nitro-phenyl)-2,2-difluoro-butan-1-ol (1.60 mmol), the product (R)-4-(2-chloro-5-nitro-phenyl)-5,5-difluoro-4-methyl-5,6-dihydro-4H-[1,3]oxazin-2-ylamine (400 mg) was obtained as a colorless gum. MS (ISP): m/z=306.1 [M+H]$^+$.

General Procedure F: Synthesis of the Intermediate DMTr-Protected Amino Oxazines XXI To a solution of the amino oxazine XX (2.4 mmol) and triethylamine (0.66 ml; 4.8 mmol) in dichloromethane (25 ml) at 0° C. was added 4,4'-dimethoxytrityl chloride (DMTr-Cl) (0.89 g; 2.6 mmol) and the green reaction mixture was stirred at 23° C. for 2 hours. Extraction with water, then drying of the organic layer over Na$_2$SO$_4$, filtration and evaporation gave a crude product which was purified by silica gel column chromatography with n-heptane and ethyl acetate to give the pure DMTr-protected amino oxazine XXI.

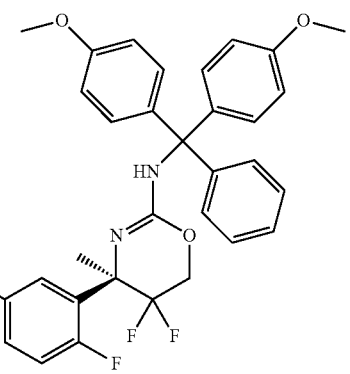

Intermediate XXI-1 (R$^2$=F; R$^3$=Me; R$^4$ and R$^5$=H): Starting from (R)-4-(5-bromo-2-fluoro-phenyl)-5,5-difluoro-4-methyl-5,6-dihydro-4H-[1,3]oxazin-2-ylamine (intermediate XX-1) (0.77 g, 2.4 mmol), the product [bis-(4-methoxyphenyl)-phenyl-methyl]-[(R)-4-(5-bromo-2-fluoro-phenyl)-5,5-difluoro-4-methyl-5,6-dihydro-4H-[1,3]oxazin-2-yl]-amine (1.11 g) was obtained as a white foam. MS (ISP): m/z=625.3 [M+H]$^+$ and 627.4 [M+2+H]$^+$.

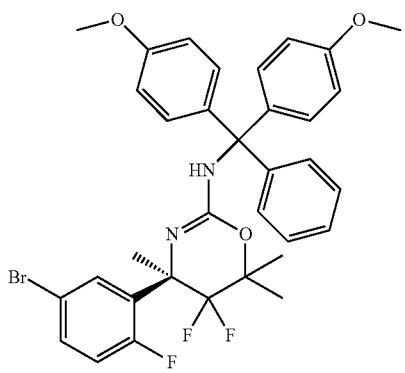 [SMILES: COc1ccc(C(NC2=N[C@](C)(c3cc(Br)ccc3F)C(F)(F)C(C)(C)O2)(c2ccccc2)c2ccc(OC)cc2)cc1]

Intermediate XXI-2 (R$^2$=F; R$^3$, R$^4$ and R$^5$=Me): Starting from (R)-4-(5-bromo-2-fluoro-phenyl)-5,5-difluoro-4,6,6-trimethyl-5,6-dihydro-4H-[1,3]oxazin-2-ylamine (intermediate XX-2) (0.77 g, 2.2 mmol), the product [bis-(4-methoxyphenyl)-phenyl-methyl]-[(R)-4-(5-bromo-2-fluoro-phenyl)-5,5-difluoro-4,6,6-trimethyl-5,6-dihydro-4H-[1,3]oxazin-2-yl]-amine (1.10 g) was obtained as a white foam. MS (ISP): m/z=653.3 [M+H]$^+$ and 655.3 [M+2+H]$^+$.

General Procedure G1: Synthesis of the Intermediate Diamines XI (from Nitro Compounds X)

To a solution of nitro compound X (4.47 mmol) in ethanol (35 ml) was added at 23° C. under inert atmosphere palladium on carbon (10% Pd/C, 238 mg, 5 mol %) and the mixture was stirred under hydrogen atmosphere (balloon) at 23° C. for 1 h. The catalyst was filtered off and washed twice with ethanol. The solvent was removed under reduced pressure to give the intermediate diamine XI as a crude product which was used without further purification.

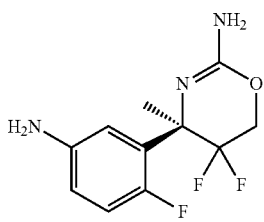 [SMILES: C[C@]1(c2cc(N)ccc2F)N=C(N)OCC1(F)F]

Intermediate XI-1 (R$^2$=F; R$^3$=Me): Starting from (R)-5,5-difluoro-4-(2-fluoro-5-nitro-phenyl)-4-methyl-5,6-dihydro-4H-[1,3]oxazin-2-ylamine (intermediate X-1) (1.29 g, 4.47 mmol), the product (R)-4-(5-amino-2-fluoro-phenyl)-5,5-difluoro-4-methyl-5,6-dihydro-4H-[1,3]oxazin-2-ylamine (1.14 g) was obtained as a colorless foam. MS (ISP): m/z=260.1 [M+H]$^+$. Intermediate XI-2 (R$^{2a}$ and R$^{2b}$=F; R$^3$=Me): Starting from (R)-5,5-difluoro-4-(2,3-difluoro-5-nitro-phenyl)-4-methyl-5,6-dihydro-4H-[1,3]oxazin-2-ylamine (intermediate X-2) (0.33 mmol), the product (R)-4-(5-amino-2,3-difluoro-phenyl)-5,5-difluoro-4-methyl-5,6-dihydro-4H-[1,3]oxazin-2-ylamine (57 mg) was obtained as a yellow gum. MS (ISP): m/z=278.1 [M+H]$^+$.

Synthesis of Intermediate XI-3 (R$^2$=Cl; R$^3$=Me)

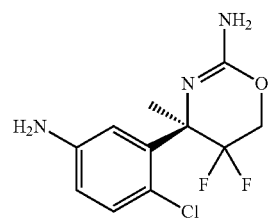 [SMILES: C[C@]1(c2cc(N)ccc2Cl)N=C(N)OCC1(F)F]

Under an inert atmosphere of argon a solution of (R)-4-(2-chloro-5-nitro-phenyl)-5,5-difluoro-4-methyl-5,6-dihydro-4H-[1,3]oxazin-2-ylamine (intermediate X-3) (50 mg, 0.16 mmol) in tetrahydrofurane (1 ml) was treated at 0° C. with Raney nickel (50% in water, 0.07 ml). The mixture was stirred under hydrogen atmosphere at 0° C. for 15 minutes. The catalyst was filtered off and the filtrate was evaporated at reduced pressure to give the (R)-4-(5-amino-2-chloro-phenyl)-5,5-difluoro-4-methyl-5,6-dihydro-4H-[1,3]oxazin-2-ylamine (42 mg, 93% of theory) as a yellow oil which was used without further purification. MS (ISP): m/z=276.1 [M+H]$^+$.

Synthesis of Intermediate XI-4 (R$^2$=H; R$^3$=Me)

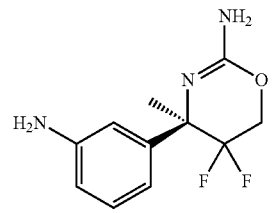 [SMILES: C[C@]1(c2cccc(N)c2)N=C(N)OCC1(F)F]

Starting from (R)-4-(2-chloro-5-nitro-phenyl)-5,5-difluoro-4-methyl-5,6-dihydro-4H-[1,3]oxazin-2-ylamine (intermediate X-3) (0.33 mmol) and following general procedure G1 the product (R)-4-(3-amino-phenyl)-5,5-difluoro-4-methyl-5,6-dihydro-4H-[1,3]oxazin-2-ylamine (65 mg) was obtained as a foam. MS (ISP): m/z=242.3 [M+H]

General Procedure G2: Synthesis of the Intermediate Diamines XI (from Benzophenone Imines XXII)

To a solution of intermediate benzophenone imine XXII (1.6 mmol) in methylene chloride (24 ml) at 23° C. was added trifluoroacetic acid (TFA) (6 ml) turning the mixture immediately into an orange solution. After 1 hour mass spectroscopy showed no trityl-group anymore but still benzophenone imine present. Then 1 M HCl (10 ml) and 1,4-dioxane (40 ml) were added and the mixture was stirred vigorously at 23° C. for 1-18 h. Poured into 1 M Na$_2$CO$_3$-solution, extracted with methylene chloride, washed the organic layer with brine and dried over Na$_2$SO$_4$. Removal of the solvent in vacuum left a green oil which was purified by chromatographed on SiO$_2$—NH$_2$ with methylene chloride to methylene chloride/methanol 19:1 to give the pure intermediate diamine XI.

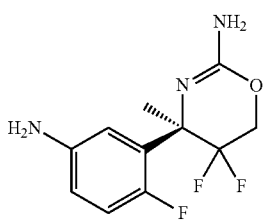 [SMILES: C[C@]1(c2cc(N)ccc2F)N=C(N)OCC1(F)F]

Intermediate XI-1 ($R^2$=F; $R^3$=Me; $R^4$ and $R^5$=H): Starting from {(R)-4-[5-(benzhydrylidene-amino)-2-fluoro-phenyl]-5,5-difluoro-4-methyl-5,6-dihydro-4H-[1,3]oxazin-2-yl}-[bis-(4-methoxy-phenyl)-phenyl-methyl]-amine (intermediate XXII-1) (1.15 g, 1.6 mmol), the product (R)-4-(5-amino-2-fluoro-phenyl)-5,5-difluoro-4-methyl-5,6-dihydro-4H-[1,3]oxazin-2-ylamine (0.34 g) was obtained as an off-white foam. MS (ISP): m/z=260.1 [M+H]$^+$.

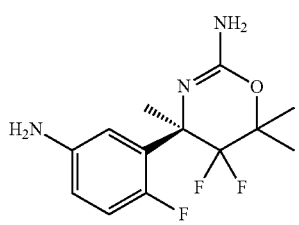 [SMILES: CC1(C)OC(N)=N[C@](C)(c2cc(N)ccc2F)C1(F)F]

Intermediate XI-2 ($R^2$=F; $R^3$, $R^4$ and $R^5$=Me): Starting from {(R)-4-[5-(benzhydrylidene-amino)-2-fluoro-phenyl]-5,5-difluoro-4,6,6-trimethyl-5,6-dihydro-4H-[1,3]oxazin-2-yl}-[bis-(4-methoxy-phenyl)-phenyl-methyl]-amine (intermediate XXII-2) (1.29 g, 1.7 mmol), the product (R)-4-(5-amino-2-fluoro-phenyl)-5,5-difluoro-4,6,6-trimethyl-5,6-dihydro-4H-[1,3]oxazin-2-ylamine (0.365 g) was obtained as an off-white foam. MS (ISP): m/z=288.0 [M+H]$^+$.

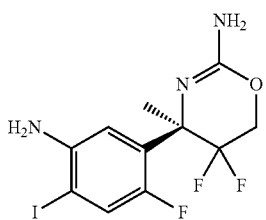 [SMILES: C[C@]1(c2cc(N)c(I)cc2F)N=C(N)OCC1(F)F]

Intermediate XI-3 ($R^{2a}$=F; $R^{2b}$=I; $R^3$=Me; $R^4$ and $R^5$=H): A solution of (R)-4-(5-amino-2-fluoro-phenyl)-5,5-difluoro-4-methyl-5,6-dihydro-4H-[1,3]oxazin-2-ylamine (intermediate XI-1) (500 mg, 1.9 mmol) and ammonium iodide (308 mg, 2.1 mmol) in acetic acid (9.6 ml) was treated at room temperature with an aqueous solution of hydrogen peroxide (35%, 0.19 ml, 2.1 mmol). After stirring overnight 50% of the starting material was left. Another equivalent of ammonium iodide and hydrogen peroxide was added and stirring continued at room temperature overnight. For the workup, the reaction mixture was filtered, the filtrate treated with sodium thiosulphate, then extracted with ethyl acetate (3×). The combined organic layers were washed with a saturated solution of sodium hydrogen carbonate, then dried over sodium sulphate and evaporated at reduced pressure. In order to eliminate residual acetic acid, the crude product was dissolved in dichloromethane and extracted again with a saturated solution of sodium hydrogen carbonate. The crude product was purified by chromatography on an Isolute flash NH$_2$ column using a gradient of heptane/ethyl acetate=100/0 to 0/100 as the eluent. The (R)-4-(5-amino-2-fluoro-4-iodo-phenyl)-5,5-difluoro-4-methyl-5,6-dihydro-4H-[1,3]oxazin-2-ylamine was obtained as a yellow solid (415 mg, 56% of theory). MS (ISP): m/z=386.0 [M+H]$^+$.

General Procedure H: Synthesis of the Intermediate Benzophenone Imines XXII

Under argon in a sealed tube were added to a solution of the DMTr-protected amino oxazine XXI (1.8 mmol) in toluene (20 mL) sodium tert-butoxide (507 mg, 5.3 mmol), 2-di-tert-butylphosphino-2',4',6'-triisopropylbiphenyl (t-Bu X-phos) (75 mg, 10 mol %) and tris(dibenzylideneacetone)dipalladium (0) ((dba)$_3$Pd$_2$.CHCl$_3$) (55 mg, 3 mol %). Benzophenone imine (0.59 ml, 3.5 mmol) was added finally via syringe. The tube was sealed under argon and the mixture was stirred at 105° C. for 2-18 h. The brown solution was extracted with ethyl acetate and water. The organic layer was washed with brine, dried over Na$_2$SO$_4$, filtered and evaporated to give a brown residue which was purified by silica gel column chromatography with n-heptane and ethyl acetate to give the pure intermediate benzophenone imines XXII.

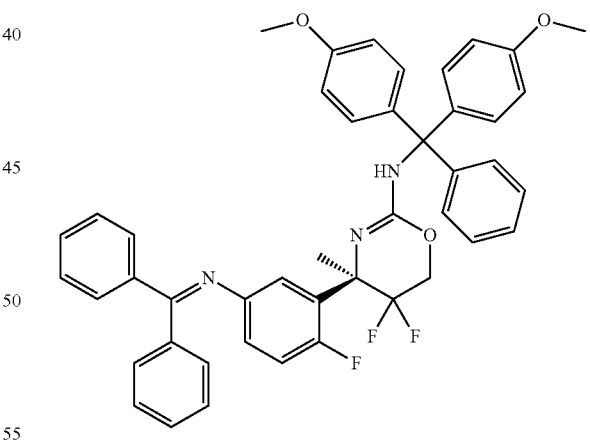

Intermediate XXII-1 ($R^2$=F; $R^3$=Me; $R^4$ and $R^5$=H): Starting from [bis-(4-methoxy-phenyl)-phenyl-methyl]-[(R)-4-(5-bromo-2-fluoro-phenyl)-5,5-difluoro-4-methyl-5,6-dihydro-4H-[1,3]oxazin-2-yl]-amine (intermediate XXI-1) (1.1 g, 1.8 mmol), the product {(R)-4-[5-(benzhydrylidene-amino)-2-fluoro-phenyl]-5,5-difluoro-4-methyl-5,6-dihydro-4H-[1,3]oxazin-2-yl}-[bis-(4-methoxy-phenyl)-phenyl-methyl]-amine (1.15 g) was obtained as a light brown foam. MS (ISP): m/z=726.4 [M+H]$^+$.

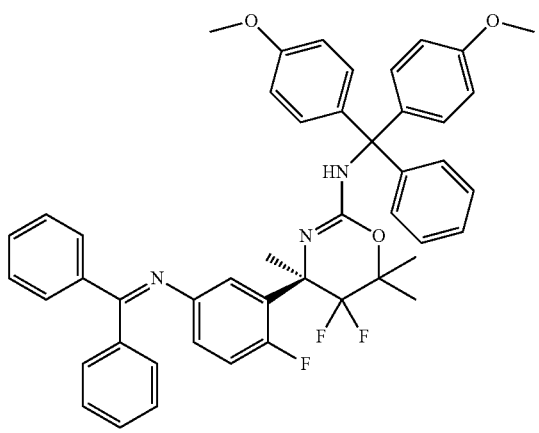 [SMILES: COc1ccc(C(NC2=N[C@](C)(c3cc(N=C(c4ccccc4)c4ccccc4)ccc3F)C(F)(F)C(C)(C)O2)(c2ccccc2)c2ccc(OC)cc2)cc1]

Intermediate XXII-2 (R²=F; R³, R⁴ and R⁵=Me): Starting from [bis-(4-methoxy-phenyl)-phenyl-methyl]-[(R)-4-(5-bromo-2-fluoro-phenyl)-5,5-difluoro-4,6,6-trimethyl-5,6-dihydro-4H-[1,3]oxazin-2-yl]-amine (intermediate XXI-2) (1.1 g, 1.7 mmol), the product {(R)-4-[5-(benzhydrylidene-amino)-2-fluoro-phenyl]-5,5-difluoro-4,6,6-trimethyl-5,6-dihydro-4H-[1,3]oxazin-2-yl}-[bis-(4-methoxy-phenyl)-phenyl-methyl]-amine (1.29 g) was obtained as a light brown foam. MS (ISP): m/z=754.5 [M+H]⁺.

General Procedure I: Synthesis of the Amides I

To a solution of the carboxylic acid (0.23 mmol) in methanol (5 ml) at 0° C. was added 4-(4,6-dimethoxy[1.3.5]triazin-2-yl)-4-methylmorpholinium chloride hydrate (DMTMM) (80 mg, 0.27 mmol). The colorless solution was stirred at 0° C. for 30 min, then a solution of the intermediate diamine XI (0.21 mmol) in methanol (5 ml) was added dropwise at 0° C. via syringe. The reaction mixture was stirred at 23° C. for 18-60 h. Poured into 1 M Na₂CO₃-solution, extracted with methylene chloride, washed the organic layer with brine and dried over Na₂SO₄. Removal of the solvent in vacuum left a light brown oil which was purified by silica gel column chromatography with 0-10% methanol in methylene chloride to give the pure amides I.

General Procedure J: Synthesis of the Intermediate di-Boc-Protected Amino Oxazines XXIII A solution of the amino oxazine X (8.7 mmol) in tetrahydrofuran (87 ml) was treated with triethylamine (3.16 ml, 22.7 mmol). The solution was stirred for 5 minutes, then di-tert-butyl dicarbonate 3.99 g, 18.3 mmol) was added followed by 4-dimethylamino-pyridine (0.32 g, 2.61 mmol). The mixture was stirred at room temperature and the progress of the reaction followed by thin layer chromatography (heptane:ethyl acetate=1:1). After 2 hours the reaction mixture was evaporated at reduced pressure. Purification of the crude product by flash chromatography on silica gel using a gradient of heptane and ethyl acetate as the eluent yielded the di-protected amino oxazine XXIII.

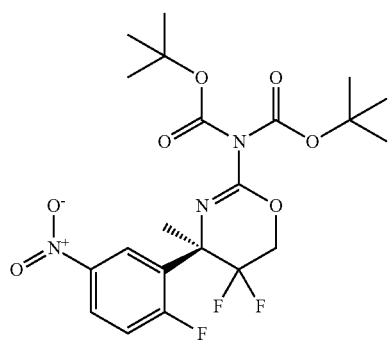 [SMILES: CC(C)(C)OC(=O)N(C(=O)OC(C)(C)C)C1=N[C@](C)(c2cc([N+](=O)[O-])ccc2F)C(F)(F)CO1]

Intermediate XXIII-1 (R²=F; R³=Me; R⁴ and R⁵=H): Starting from (R)-5,5-difluoro-4-(2-fluoro-5-nitro-phenyl)-4-methyl-5,6-dihydro-4H-[1,3]oxazin-2-ylamine (intermediate X-1) (2.52 g, 8.7 mmol), the product [(R)-5,5-difluoro-4-(2-fluoro-5-nitro-phenyl)-4-methyl-5,6-dihydro-4H-[1,3]oxazin-2-yl]-dicarbamic acid bis-tert-butyl ester (3.48 g) was obtained as a white crystalline solid. MS (ISP): m/z=490.2 [M+H]⁺, 334.2 [M-Boc-tert-butyl+H]⁺.

General Procedure K: Synthesis of the Intermediate Boc-Protected Amino Oxazines XXIV A solution of the amino oxazine XXXIII (4.5 mmol) in dichloromethane (9 ml) was cooled to 0° C. and treated dropwise with trifluoroacetic acid (0.69 ml, 9 mmol). The solution was stirred at 0° C. overnight. The reaction mixture was warmed to room temperature. In order to complete the transformation, the reaction mixture was cooled again to 0° C., another equivalent of trifluoroacetic acid was added and the mixture left to warm to room temperature. After 4 hours the solution was poured into a saturated solution of sodium hydrogencarbonate, then extracted with ethyl acetate. The combined organic layers were dried over sodium sulphate and evaporated. Purification of the crude product by flash chromatography on silica gel using a gradient of heptane and ethyl acetate as the eluent yielded the amino oxazine XXIV together with starting material and amino oxazine X.

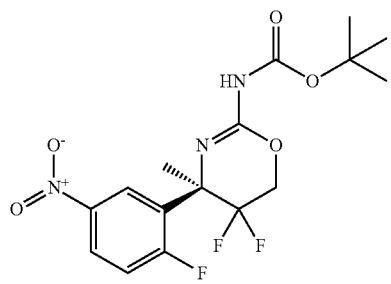 [SMILES: CC(C)(C)OC(=O)NC1=N[C@](C)(c2cc([N+](=O)[O-])ccc2F)C(F)(F)CO1]

Intermediate XXIV-1 (R²=F; R³=Me; R⁴ and R⁵=H): Starting from [(R)-5,5-difluoro-4-(2-fluoro-5-nitro-phenyl)-4-methyl-5,6-dihydro-4H-[1,3]oxazin-2-yl]-dicarbamic acid bis-tert-butyl ester (intermediate XXIII-1) (2.2 g, 4.5 mmol), the product [(R)-5,5-difluoro-4-(2-fluoro-5-nitro-phenyl)-4-methyl-5,6-dihydro-4H-[1,3]oxazin-2-yl]-carbamic acid tert-butyl ester (0.96 g) was obtained as a white foam. MS (ISP): m/z=388.1 [M–H]⁻.

General Procedure L: Synthesis of the Intermediate Diamines XXV (from Nitro Compounds XXIV)

To a solution of nitro compound XXIV (3.42 mmol) (intermediate XXIII-1) in a mixture of ethanol (33 ml) and tetrahydrofuran (33 ml) was added at 23° C. under inert atmosphere palladium on carbon (133 mg, 1.25 mmol). The mixture was evacuated and flushed with hydrogen three times, then stirred overnight. After completion, the mixture was filtered and concentrated at reduced pressure. The crude product was purified by flash chromatography using a gradient of heptane and ethyl acetate as the eluent to yield the Boc-protected diamine XXV.

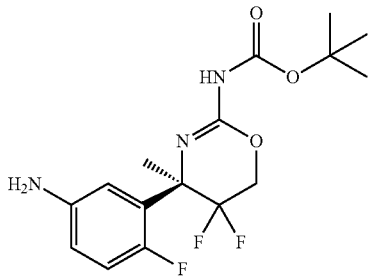 [SMILES: CC(C)(C)OC(=O)NC1=N[C@](C)(c2cc(N)ccc2F)C(F)(F)CO1]

Intermediate XXV-1 ($R^2$=F; $R^3$=Me; $R^4$ and $R^5$=H): Starting from [(R)-5,5-difluoro-4-(2-fluoro-5-nitro-phenyl)-4-methyl-5,6-dihydro-4H-[1,3]oxazin-2-yl]-carbamic acid tert-butyl ester (1.33 g, 3.42 mmol), the product [(R)-4-(5-amino-2-fluoro-phenyl)-5,5-difluoro-4-methyl-5,6-dihydro-4H-[1,3]oxazin-2-yl]-carbamic acid tert-butyl ester (0.83 g) was obtained as a white foam. MS (ISP): m/z=358.0 [M−H]⁻.

The following examples have a basic group. Depending on the reaction and purification conditions they were isolated in either the free base form, or as a salt, or in both free base and salt forms.

EXAMPLE 1

5-Chloro-pyridine-2-carboxylic acid [3-((R)-2-amino-5,5-difluoro-4-methyl-5,6-dihydro-4H-[1,3]oxazin-4-yl)-4-fluoro-phenyl]-amide The condensation of (R)-4-(5-amino-2-fluoro-phenyl)-5,5-difluoro-4-methyl-5,6-dihydro-4H-[1,3]oxazin-2-ylamine (intermediate XI-1) and 5-chloro-pyridine-2-carboxylic acid following procedure I yielded the title compound as a colorless oil. MS (ISP): m/z=399.2 [M+H]⁺.

EXAMPLE 2

5-Fluoro-pyridine-2-carboxylic acid [3-((R)-2-amino-5,5-difluoro-4-methyl-5,6-dihydro-4H-[1,3]oxazin-4-yl)-4-fluoro-phenyl]-amide The condensation of (R)-4-(5-amino-2-fluoro-phenyl)-5,5-difluoro-4-methyl-5,6-dihydro-4H-[1,3]oxazin-2-ylamine (intermediate XI-1) and 5-fluoro-pyridine-2-carboxylic acid following procedure I yielded the title compound as a colorless oil. MS (ISP): m/z=383.2 [M+H]⁺.

EXAMPLE 3

3-Chloro-pyridine-2-carboxylic acid [3-((R)-2-amino-5,5-difluoro-4-methyl-5,6-dihydro-4H-[1,3]oxazin-4-yl)-4-fluoro-phenyl]-amide The condensation of (R)-4-(5-amino-2-fluoro-phenyl)-5,5-difluoro-4-methyl-5,6-dihydro-4H-[1,3]oxazin-2-ylamine (intermediate XI-1) and 3-chloro-pyridine-2-carboxylic acid following procedure I yielded the title compound as a colorless solid. MS (ISP): m/z=399.1 [M+H]⁺.

EXAMPLE 4

3,5-Difluoro-pyridine-2-carboxylic acid [3-((R)-2-amino-5,5-difluoro-4-methyl-5,6-dihydro-4H-[1,3]oxazin-4-yl)-4-fluoro-phenyl]-amide The condensation of (R)-4-(5-amino-2-fluoro-phenyl)-5,5-difluoro-4-methyl-5,6-dihydro-4H-[1,3]oxazin-2-ylamine (intermediate XI-1) and 3,5-difluoro-pyridine-2-carboxylic acid following procedure I yielded the title compound as a colorless solid. MS (ISP): m/z=401.2 [M+H]⁺.

EXAMPLE 5

3-Chloro-5-trifluoromethyl-pyridine-2-carboxylic acid [3-((R)-2-amino-5,5-difluoro-4-methyl-5,6-dihydro-4H-[1,3]oxazin-4-yl)-4-fluoro-phenyl]-amide The condensation of (R)-4-(5-amino-2-fluoro-phenyl)-5,5-difluoro-4-methyl-5,6-dihydro-4H-[1,3]oxazin-2-ylamine (intermediate XI-1) and 3-chloro-5-trifluoromethyl-pyridine-2-carboxylic acid following procedure I yielded the title compound as a light yellow oil. MS (ISP): m/z=467.2 [M+H]⁺.

EXAMPLE 6

3-Trifluoromethyl-pyridine-2-carboxylic acid [3-((R)-2-amino-5,5-difluoro-4-methyl-5,6-dihydro-4H-[1,3]oxazin-4-yl)-4-fluoro-phenyl]-amide The condensation of (R)-4-(5-amino-2-fluoro-phenyl)-5,5-difluoro-4-methyl-5,6-dihydro-4H-[1,3]oxazin-2-ylamine (intermediate XI-1) and 3-trifluoromethyl-pyridine-2-carboxylic acid following procedure I yielded the title compound as a colorless solid. MS (ISP): m/z=433.2 [M+H]⁺.

EXAMPLE 7

3-Chloro-5-fluoro-pyridine-2-carboxylic acid [3-((R)-2-amino-5,5-difluoro-4-methyl-5,6-dihydro-4H-[1,3]oxazin-4-yl)-4-fluoro-phenyl]-amide The condensation of (R)-4-(5-amino-2-fluoro-phenyl)-5,5-difluoro-4-methyl-5,6-dihydro-4H-[1,3]oxazin-2-ylamine (intermediate XI-1) and 3-chloro-5-fluoro-pyridine-2-carboxylic acid following procedure I yielded the title compound as a colorless solid. MS (ISP): m/z=417.2 [M+H]⁺.

EXAMPLE 8

3,5-Dichloro-pyridine-2-carboxylic acid [3-((R)-2-amino-5,5-difluoro-4-methyl-5,6-dihydro-4H-[1,3]oxazin-4-yl)-4-fluoro-phenyl]-amide The condensation of (R)-4-(5-amino-2-fluoro-phenyl)-5,5-difluoro-4-methyl-5,6-dihydro-4H-[1,3]oxazin-2-ylamine (intermediate XI-1) and 3,5-dichloro-pyridine-2-carboxylic

EXAMPLE 9

Pyridine-2-carboxylic acid [3-((R)-2-amino-5,5-difluoro-4-methyl-5,6-dihydro-4H-[1,3]oxazin-4-yl)-4-fluoro-phenyl]-amide The condensation of (R)-4-(5-amino-2-fluoro-phenyl)-5,5-difluoro-4-methyl-5,6-dihydro-4H-[1,3]oxazin-2-ylamine (intermediate XI-1) and pyridine-2-carboxylic acid following procedure I yielded the title compound as a colorless solid. MS (ISP): m/z=365.2 [M+H]$^+$.

EXAMPLE 10

3-Fluoro-pyridine-2-carboxylic acid [3-((R)-2-amino-5,5-difluoro-4-methyl-5,6-dihydro-4H-[1,3]oxazin-4-yl)-4-fluoro-phenyl]-amide The condensation of (R)-4-(5-amino-2-fluoro-phenyl)-5,5-difluoro-4-methyl-5,6-dihydro-4H-[1,3]oxazin-2-ylamine (intermediate XI-1) and 3-fluoro-pyridine-2-carboxylic acid following procedure I yielded the title compound as a colorless solid. MS (ISP): m/z=383.2 [M+H]$^+$.

EXAMPLE 11

5-Cyano-pyridine-2-carboxylic acid [3-((R)-2-amino-5,5-difluoro-4-methyl-5,6-dihydro-4H-[1,3]oxazin-4-yl)-4-fluoro-phenyl]-amide and example 11a) 5-Cyano-pyridine-2-carboxylic acid [3-((R)-2-amino-5,5-difluoro-4-methyl-5,6-dihydro-4H-[1,3]oxazin-4-yl)-4-fluoro-phenyl]-amide hydrochloride The condensation of (R)-4-(5-amino-2-fluoro-phenyl)-5,5-difluoro-4-methyl-5,6-dihydro-4H-[1,3]oxazin-2-ylamine (intermediate XI-1) and 5-cyano-pyridine-2-carboxylic acid following procedure I yielded the title compound as a colorless solid. MS (ISP): m/z=390.2 [M+H]$^+$. After dissolution in ethanol followed by treatment with hydrochloric acid (1N) and evaporation the residue was dissolved again in water and evaporated. The 5-cyano-pyridine-2-carboxylic acid [3-((R)-2-amino-5,5-difluoro-4-methyl-5,6-dihydro-4H-[1,3]oxazin-4-yl)-4-fluoro-phenyl]-amide hydrochloride was obtained as a white solid.

EXAMPLE 12

5-Chloro-pyrimidine-2-carboxylic acid [3-((R)-2-amino-5,5-difluoro-4-methyl-5,6-dihydro-4H-[1,3]oxazin-4-yl)-4-fluoro-phenyl]-amide The condensation of (R)-4-(5-amino-2-fluoro-phenyl)-5,5-difluoro-4-methyl-5,6-dihydro-4H-[1,3]oxazin-2-ylamine (intermediate XI-1) and 5-chloro-pyrimidine-2-carboxylic acid following procedure I yielded the title compound as a colorless solid. MS (ISP): m/z=400.0 [M+H]$^+$.

EXAMPLE 13

5-Chloro-3-methyl-pyridine-2-carboxylic acid [3-((R)-2-amino-5,5-difluoro-4-methyl-5,6-dihydro-4H-[1,3]oxazin-4-yl)-4-fluoro-phenyl]-amide The condensation of (R)-4-(5-amino-2-fluoro-phenyl)-5,5-difluoro-4-methyl-5,6-dihydro-4H-[1,3]oxazin-2-ylamine (intermediate XI-1) and 5-chloro-3-methyl-pyridine-2-carboxylic acid following procedure I yielded the title compound as a colorless solid. MS (ISP): m/z=413.3 [M+H]$^+$.

EXAMPLE 14

5-(2,2,2-Trifluoro-ethoxy)-pyridine-2-carboxylic acid [3-((R)-2-amino-5,5-difluoro-4-methyl-5,6-dihydro-4H-[1,3]oxazin-4-yl)-4-fluoro-phenyl]-amide The condensation of (R)-4-(5-amino-2-fluoro-phenyl)-5,5-difluoro-4-methyl-5,6-dihydro-4H-[1,3]oxazin-2-ylamine (intermediate XI-1) and 5-(2,2,2-trifluoro-ethoxy)-pyridine-2-carboxylic acid following procedure I yielded the title compound as a colorless solid. MS (ISP): m/z=463.2 [M+H]$^+$.

EXAMPLE 15

5-Chloro-3-fluoro-pyridine-2-carboxylic acid [3-((R)-2-amino-5,5-difluoro-4-methyl-5,6-dihydro-4H-[1,3]oxazin-4-yl)-4-fluoro-phenyl]-amide The condensation of (R)-4-(5-amino-2-fluoro-phenyl)-5,5-difluoro-4-methyl-5,6-dihydro-4H-[1,3]oxazin-2-ylamine (intermediate XI-1) and 5-chloro-3-fluoro-pyridine-2-carboxylic acid following procedure I yielded the title compound as a colorless solid. MS (ISP): m/z=463.2 [M+H]$^+$.

EXAMPLE 16

5-Trifluoromethyl-pyrimidine-2-carboxylic acid [3-((R)-2-amino-5,5-difluoro-4-methyl-5,6-dihydro-4H-[1,3]oxazin-4-yl)-4-fluoro-phenyl]-amide The condensation of (R)-4-(5-amino-2-fluoro-phenyl)-5,5-difluoro-4-methyl-5,6-dihydro-4H-[1,3]oxazin-2-ylamine (intermediate XI-1) and 5-trifluoromethyl-pyrimidine-2-carboxylic acid following procedure I yielded the title compound as a colorless oil. MS (ISP): m/z=434.2 [M+H]$^+$.

EXAMPLE 17

5-Trifluoromethyl-pyrazine-2-carboxylic acid [3-((R)-2-amino-5,5-difluoro-4-methyl-5,6-dihydro-4H-[1,3]oxazin-4-yl)-4-fluoro-phenyl]-amide The condensation of (R)-4-(5-amino-2-fluoro-phenyl)-5,5-difluoro-4-methyl-5,6-dihydro-4H-[1,3]oxazin-2-ylamine (intermediate XI-1) and 5-trifluoromethyl-pyrazine-2-carboxylic acid following procedure I yielded the title compound as a colorless oil. MS (ISP): m/z=434.2 [M+H]$^+$.

EXAMPLE 18

4-Chloro-1-methyl-1H-pyrazole-3-carboxylic acid [3-((R)-2-amino-5,5-difluoro-4-methyl-5,6-dihydro-4H-[1,3]oxazin-4-yl)-4-fluoro-phenyl]-amide The condensation of (R)-4-(5-amino-2-fluoro-phenyl)-5,5-difluoro-4-methyl-5,6-dihydro-4H-[1,3]oxazin-2-ylamine (intermediate XI-1) and 4-chloro-1-methyl-1H-pyrazole-3-carboxylic acid following procedure I yielded the title compound as a colorless amorphous material. MS (ISP): m/z=402.3 [M+H]$^+$.

(Top of page 83, continuing from previous: acid following procedure I yielded the title compound as a colorless solid. MS (ISP): m/z=433.2 [M+H]$^+$.)

EXAMPLE 19

5-Chloro-pyridine-2-carboxylic acid [3-((R)-2-amino-5,5-difluoro-4,6,6-trimethyl-5,6-dihydro-4H-[1,3]oxazin-4-yl)-4-fluoro-phenyl]-amide The condensation of (R)-4-(5-amino-2-fluoro-phenyl)-5,5-difluoro-4,6,6-trimethyl-5,6-dihydro-4H-[1,3]oxazin-2-ylamine (intermediate XI-2) and 5-chloro-pyridine-2-carboxylic acid following procedure I yielded the title compound as a white foam. MS (ISP): m/z=427.2 [M+H]$^+$.

EXAMPLE 20

3-Chloro-5-trifluoromethyl-pyridine-2-carboxylic acid [3-((R)-2-amino-5,5-difluoro-4,6,6-trimethyl-5,6-dihydro-4H-[1,3]oxazin-4-yl)-4-fluoro-phenyl]-amide and example 20a) 3-Chloro-5-trifluoromethyl-pyridine-2-carboxylic acid [3-((R)-2-amino-5,5-difluoro-4,6,6-trimethyl-5,6-dihydro-4H-[1,3]oxazin-4-yl)-4-fluoro-phenyl]-amide hydrochloride The condensation of (R)-4-(5-amino-2-fluoro-phenyl)-5,5-difluoro-4,6,6-trimethyl-5,6-dihydro-4H-[1,3]oxazin-2-ylamine (intermediate XI-2) and 3-chloro-5-trifluoromethyl-pyridine-2-carboxylic acid following procedure I yielded the title compound as a white foam. MS (ISP): m/z=495.1 [M+H]$^+$. After treatment of the title compound with hydrochloric acid in dioxane (4N), evaporation and trituration with diethylether, the 3-chloro-5-trifluoromethyl-pyridine-2-carboxylic acid [3-((R)-2-amino-5,5-difluoro-4,6,6-trimethyl-5,6-dihydro-4H-[1,3]oxazin-4-yl)-4-fluoro-phenyl]-amide hydrochloride was obtained as a white solid.

EXAMPLE 21

5-Cyano-pyridine-2-carboxylic acid [3-((R)-2-amino-5,5-difluoro-4,6,6-trimethyl-5,6-dihydro-4H-[1,3]oxazin-4-yl)-4-fluoro-phenyl]-amide The condensation of (R)-4-(5-amino-2-fluoro-phenyl)-5,5-difluoro-4,6,6-trimethyl-5,6-dihydro-4H-[1,3]oxazin-2-ylamine (intermediate XI-2) and 5-cyano-pyridine-2-carboxylic acid following procedure I yielded the title compound as an off-white foam. MS (ISP): m/z=418.2 [M+H]$^+$.

EXAMPLE 22

3-Chloro-5-cyano-pyridine-2-carboxylic acid [3-((R)-2-amino-5,5-difluoro-4,6,6-trimethyl-5,6-dihydro-4H-[1,3]oxazin-4-yl)-4-fluoro-phenyl]-amide and example 22a) 3-Chloro-5-cyano-pyridine-2-carboxylic acid [3-((R)-2-amino-5,5-difluoro-4,6,6-trimethyl-5,6-dihydro-4H-[1,3]oxazin-4-yl)-4-fluoro-phenyl]-amide hydrochloride The condensation of (R)-4-(5-amino-2-fluoro-phenyl)-5,5-difluoro-4,6,6-trimethyl-5,6-dihydro-4H-[1,3]oxazin-2-ylamine (intermediate XI-2) and 3-chloro-5-cyano-pyridine-2-carboxylic acid following procedure I yielded the 3-chloro-5-cyano-pyridine-2-carboxylic acid [3-((R)-2-amino-5,5-difluoro-4,6,6-trimethyl-5,6-dihydro-4H-[1,3]oxazin-4-yl)-4-fluoro-phenyl]-amide which, after treatment with hydrochloric acid in dioxane (4N), evaporation and trituration with diethylether, gave the title compound as a white solid. MS (ISP): m/z=452.1 [M+H]$^+$.

EXAMPLE 23

3,5-Dichloro-pyridine-2-carboxylic acid [3-((R)-2-amino-5,5-difluoro-4,6,6-trimethyl-5,6-dihydro-4H-[1,3]oxazin-4-yl)-4-fluoro-phenyl]-amide and example 23a) 3,5-Dichloro-pyridine-2-carboxylic acid [3-((R)-2-amino-5,5-difluoro-4,6,6-trimethyl-5,6-dihydro-4H-[1,3]oxazin-4-yl)-4-fluoro-phenyl]-amide hydrochloride The condensation of (R)-4-(5-amino-2-fluoro-phenyl)-5,5-difluoro-4,6,6-trimethyl-5,6-dihydro-4H-[1,3]oxazin-2-ylamine (intermediate XI-2) and 3,5-dichloro-pyridine-2-carboxylic acid following procedure I yielded the 3,5-dichloro-pyridine-2-carboxylic acid [3-((R)-2-amino-5,5-difluoro-4,6,6-trimethyl-5,6-dihydro-4H-[1,3]oxazin-4-yl)-4-fluoro-phenyl]-amide which, after treatment with hydrochloric acid in dioxane (4N), evaporation and trituration with diethylether, gave the title compound as a white solid. MS (ISP): m/z=461.2 [M+H]$^+$, 463.1 [M+2+H]$^+$.

EXAMPLE 24

5-Chloro-3-fluoro-pyridine-2-carboxylic acid [3-((R)-2-amino-5,5-difluoro-4,6,6-trimethyl-5,6-dihydro-4H-[1,3]oxazin-4-yl)-4-fluoro-phenyl]-amide The condensation of (R)-4-(5-amino-2-fluoro-phenyl)-5,5-difluoro-4,6,6-trimethyl-5,6-dihydro-4H-[1,3]oxazin-2-ylamine (intermediate XI-2) and 5-chloro-3-fluoro-pyridine-2-carboxylic acid following procedure I yielded the title compound as a white foam. MS (ISP): m/z=445.2 [M+H]$^+$, 447.2 [M+2+H]$^+$.

EXAMPLE 25

5-Trifluoromethyl-pyridine-2-carboxylic acid [3-((R)-2-amino-5,5-difluoro-4,6,6-trimethyl-5,6-dihydro-4H-[1,3]oxazin-4-yl)-4-fluoro-phenyl]-amide The condensation of (R)-4-(5-amino-2-fluoro-phenyl)-5,5-difluoro-4,6,6-trimethyl-5,6-dihydro-4H-[1,3]oxazin-2-ylamine (intermediate XI-2) and 5-trifluoromethyl-pyridine-2-carboxylic acid following procedure I yielded the title compound as a white foam. MS (ISP): m/z=461.2 [M+H]$^+$.

EXAMPLE 26

5-Fluoromethoxy-pyridine-2-carboxylic acid [3-((R)-2-amino-5,5-difluoro-4,6,6-trimethyl-5,6-dihydro-4H-[1,3]oxazin-4-yl)-4-fluoro-phenyl]-amide The condensation of (R)-4-(5-amino-2-fluoro-phenyl)-5,5-difluoro-4,6,6-trimethyl-5,6-dihydro-4H-[1,3]oxazin-2-ylamine (intermediate XI-2) and 5-fluoromethoxy-pyridine-2-carboxylic acid (CAS1174321-03-9, WO2009091016) following procedure I yielded the title compound as a white solid. MS (ISP): m/z=441.3 [M+H]$^+$.

EXAMPLE 27

5-Difluoromethoxy-pyridine-2-carboxylic acid [3-((R)-2-amino-5,5-difluoro-4,6,6-trimethyl-5,6-dihydro-4H-[1,3]oxazin-4-yl)-4-fluoro-phenyl]-amide The condensation of (R)-4-(5-amino-2-fluoro-phenyl)-5,5-difluoro-4,6,6-trimethyl-5,6-dihydro-4H-[1,3]oxazin-2- ylamine (intermediate XI-2) and 5-difluoromethoxy-pyridine-2-carboxylic acid (CAS1174323-34-2, WO2009091016) following procedure I yielded the title compound as a white foam. MS (ISP): m/z=459.2 [M+H]$^+$.

EXAMPLE 28

5-(2,2-Difluoro-ethoxy)-pyridine-2-carboxylic acid [3-((R)-2-amino-5,5-difluoro-4,6,6-trimethyl-5,6-dihydro-4H-[1,3]oxazin-4-yl)-4-fluoro-phenyl]-amide The condensation of (R)-4-(5-amino-2-fluoro-phenyl)-5,5-difluoro-4,6,6-trimethyl-5,6-dihydro-4H-[1,3]oxazin-2-ylamine (intermediate XI-2) and 5-(2,2-difluoro-ethoxy)-pyridine-2-carboxylic acid (CAS1097730-45-4, WO2009091016) following procedure I yielded the title compound as a white solid. MS (ISP): m/z=473.1 [M+H]$^+$.

EXAMPLE 29

5-(2,2,2-Trifluoro-ethoxy)-pyridine-2-carboxylic acid [3-((R)-2-amino-5,5-difluoro-4,6,6-trimethyl-5,6-dihydro-4H-[1,3]oxazin-4-yl)-4-fluoro-phenyl]-amide The condensation of (R)-4-(5-amino-2-fluoro-phenyl)-5,5-difluoro-4,6,6-trimethyl-5,6-dihydro-4H-[1,3]oxazin-2-ylamine (intermediate XI-2) and 5-(2,2,2-trifluoro-ethoxy)-pyridine-2-carboxylic acid following procedure I yielded the title compound as a white foam. MS (ISP): m/z=491.2 [M+H]$^+$.

The 5-(2,2,2-trifluoro-ethoxy)-pyridine-2-carboxylic acid was obtained as follows:
a) 5-(2,2,2-Trifluoro-ethoxy)-pyridine-2-carboxylic acid methyl ester
Under an atmosphere of nitrogen a solution of 5-hydroxy-pyridine-2-carboxylic acid methyl ester (200 mg, 1.31 mmol) in N,N-dimethylformamide (2 ml) was treated at room temperature with sodium hydride (55% dispersion in oil, 64 mg). After the gas formation had ceased, the suspension was cooled to 0° C. and trifluoro-methanesulphonic acid 2,2,2-trifluoro-ethyl ester (364 mg, 1.57 mmol) was added. After stirring at room temperature for 2 hours about 50% of the starting material was left. Another 364 mg of trifluoro-methanesulphonic acid 2,2,2-trifluoro-ethyl ester were added and after 30 minutes the reaction was complete. For the workup, the reaction mixture was treated with a saturated solution of sodium carbonate, then extracted with ethyl acetate (3×). The combined organic layers were washed with brine, dried over sodium sulphate, and evaporated at reduced pressure. The crude product was purified by chromatography on silica gel using a 3:1-mixture of heptane and ethyl acetate as the eluent. The 5-(2,2,2-trifluoro-ethoxy)-pyridine-2-carboxylic acid methyl ester was obtained as a white solid (216 mg, 70% of theory). MS (ISP): m/z=236.3 [M+H]$^+$.
b) 5-(2,2,2-Trifluoro-ethoxy)-pyridine-2-carboxylic acid
Under an atmosphere of nitrogen a solution of 5-(2,2,2-trifluoro-ethoxy)-pyridine-2-carboxylic acid methyl ester (216 mg, 0.92 mmol) in methanol (1 ml) was treated with a solution of lithium hydroxide monohydrate (78 mg, 1.84 mmol) in methanol (0.1 ml). After stirring for 2 hours the reaction mixture was evaporated at reduced pressure. The residue was treated with hydrochloric acid (1N), the solid material was filtered then washed with water, finally dried at high vacuum.

The 5-(2,2,2-trifluoro-ethoxy)-pyridine-2-carboxylic acid was obtained as a white solid (125 mg, 61% of theory).

EXAMPLE 30

5-(2,2,3,3-Tetrafluoro-propoxy)-pyridine-2-carboxylic acid [3-((R)-2-amino-5,5-difluoro-4,6,6-trimethyl-5,6-dihydro-4H-[1,3]oxazin-4-yl)-4-fluoro-phenyl]-amide and example 30a) 5-(2,2,3,3-Tetrafluoro-propoxy)-pyridine-2-carboxylic acid [3-((R)-2-amino-5,5-difluoro-4,6,6-trimethyl-5,6-dihydro-4H-[1,3]oxazin-4-yl)-4-fluoro-phenyl]-amide hydrochloride The condensation of (R)-4-(5-amino-2-fluoro-phenyl)-5,5-difluoro-4,6,6-trimethyl-5,6-dihydro-4H-[1,3]oxazin-2-ylamine (intermediate XI-2) and 5-(2,2,3,3-tetrafluoro-propoxy)-pyridine-2-carboxylic acid following procedure I yielded the 5-(2,2,3,3-tetrafluoro-propoxy)-pyridine-2-carboxylic acid [3-((R)-2-amino-5,5-difluoro-4,6,6-trimethyl-5,6-dihydro-4H-[1,3]oxazin-4-yl)-4-fluoro-phenyl]-amide which, after treatment with hydrochloric acid in dioxane (4N), evaporation and trituration with diethylether, gave the title compound as an off-white solid. MS (ISP): m/z=523.3 [M+H]$^+$.

The 5-(2,2,3,3-tetrafluoro-propoxy)-pyridine-2-carboxylic acid was prepared as follows:
a) 5-(2,2,3,3-Tetrafluoro-propoxy)-pyridine-2-carboxylic acid methyl ester
A solution of 5-hydroxy-pyridine-2-carboxylic acid methyl ester (2.0 g, 13.1 mmol) in acetone (40 ml) was treated with potassium carbonate (5.415 g, 39.2 mmol) and trifluoro-methanesulphonic acid 2,2,3,3-tetrafluoropropyl ester. After 4 hours stirring at room temperature the suspension was diluted with diethylether. After filtration the solution was evaporated and the yellow solid purified by chromatography on silica gel using a gradient of heptane/ethyl acetate=100:0 to 30:70 as the eluent. The 5-(2,2,3,3-tetrafluoro-propoxy)-pyridine-2-carboxylic acid methyl ester was obtained as a light yellow solid (3.49 g, 76% of theory). MS (ISP): m/z=468.1 [M+H]$^+$.
b) 5-(2,2,3,3-Tetrafluoro-propoxy)-pyridine-2-carboxylic acid
In a manner analogous to that described in example 29b), the hydrolysis of the 5-(2,2,3,3-tetrafluoro-propoxy)-pyridine-2-carboxylic acid methyl ester with lithium hydroxide yielded the title compound as a light yellow solid (yield 94% of theory). MS (ISP): m/z=253 [M]$^+$.

EXAMPLE 31

N-[3-((R)-2-Amino-5,5-difluoro-4,6,6-trimethyl-5,6-dihydro-4H-[1,3]oxazin-4-yl)-4-fluoro-phenyl]-6-cyclopropylmethoxy-nicotinamide The condensation of (R)-4-(5-amino-2-fluoro-phenyl)-5,5-difluoro-4,6,6-trimethyl-5,6-dihydro-4H-[1,3]oxazin-2-ylamine (intermediate XI-2) and 6-cyclopropylmethoxy-nicotinic acid (CAS1019546-29-2, WO2008130320) following procedure I yielded the title compound as a light yellow solid. MS (ISP): m/z=463.2 [M+H]$^+$.

EXAMPLE 32

5-Chloro-pyrimidine-2-carboxylic acid [3-((R)-2-amino-5,5-difluoro-4,6,6-trimethyl-5,6-dihydro-4H-[1,3]oxazin-4-yl)-4-fluoro-phenyl]-amide The condensation of (R)-4-(5-amino-2-fluoro-phenyl)-5,5-difluoro-4,6,6-trimethyl-5,6-dihydro-4H-[1,3]oxazin-2- ylamine (intermediate XI-2) and 5-chloro-pyrimidine-2-carboxylic acid following procedure I yielded the title compound as a white solid. MS (ISP): m/z=428.2 [M+H]⁺.

EXAMPLE 33

5-Trifluoromethyl-pyrimidine-2-carboxylic acid [3-((R)-2-amino-5,5-difluoro-4,6,6-trimethyl-5,6-dihydro-4H-[1,3]oxazin-4-yl)-4-fluoro-phenyl]-amide The condensation of (R)-4-(5-amino-2-fluoro-phenyl)-5,5-difluoro-4,6,6-trimethyl-5,6-dihydro-4H-[1,3]oxazin-2-ylamine (intermediate XI-2) and 5-trifluoromethyl-pyrimidine-2-carboxylic acid following procedure I yielded the title compound as a white foam. MS (ISP): m/z=462.2 [M+H]⁺.

EXAMPLE 34

5-Methyl-pyrazine-2-carboxylic acid [3-((R)-2-amino-5,5-difluoro-4,6,6-trimethyl-5,6-dihydro-4H-[1,3]oxazin-4-yl)-4-fluoro-phenyl]-amide The condensation of (R)-4-(5-amino-2-fluoro-phenyl)-5,5-difluoro-4,6,6-trimethyl-5,6-dihydro-4H-[1,3]oxazin-2-ylamine (intermediate XI-2) and 5-methyl-pyrazine-2-carboxylic acid following procedure I yielded the title compound as a white solid. MS (ISP): m/z=408.3 [M+H]⁺.

EXAMPLE 35

5-Trifluoromethyl-pyrazine-2-carboxylic acid [3-((R)-2-amino-5,5-difluoro-4,6,6-trimethyl-5,6-dihydro-4H-[1,3]oxazin-4-yl)-4-fluoro-phenyl]-amide and example 35a) 5-Trifluoromethyl-pyrazine-2-carboxylic acid [3-((R)-2-amino-5,5-difluoro-4,6,6-trimethyl-5,6-dihydro-4H-[1,3]oxazin-4-yl)-4-fluoro-phenyl]-amide hydrochloride The condensation of (R)-4-(5-amino-2-fluoro-phenyl)-5,5-difluoro-4,6,6-trimethyl-5,6-dihydro-4H-[1,3]oxazin-2-ylamine (intermediate XI-2) and 5-trifluoromethyl-pyrazine-2-carboxylic acid following procedure I yielded the title compound as a light yellow foam. After treatment with hydrochloric acid in dioxane (4N), evaporation and trituration with diethylether the 5-trifluoromethyl-pyrazine-2-carboxylic acid [3-((R)-2-amino-5,5-difluoro-4,6,6-trimethyl-5,6-dihydro-4H-[1,3]oxazin-4-yl)-4-fluoro-phenyl]-amide hydrochloride was obtained as a light yellow solid. MS (ISP): m/z=462.2 [M+H]⁺.

EXAMPLE 36

5-Cyclopropylmethoxy-pyrazine-2-carboxylic acid [3-((R)-2-amino-5,5-difluoro-4,6,6-trimethyl-5,6-dihydro-4H-[1,3]oxazin-4-yl)-4-fluoro-phenyl]-amide The condensation of (R)-4-(5-amino-2-fluoro-phenyl)-5,5-difluoro-4,6,6-trimethyl-5,6-dihydro-4H-[1,3]oxazin-2-ylamine (intermediate XI-2) and 5-cyclopropylmethoxy-pyrazine-2-carboxylic acid following procedure I yielded the title compound as a white solid. MS (ISP): m/z=464.3 [M+H]⁺.

The 5-cyclopropylmethoxy-pyrazine-2-carboxylic acid was obtained as follows: A solution of 5-chloro-pyrazine-2-carboxylic acid (1.5 g, 9.46 mmol) in dry dimethylsulphoxide (5 ml) was treated with cyclopropyl-methanol (1.15 ml, 14.1 mmol) and powdered potassium hydroxide (2.12 g, 37.8 mmol). The mixture was irradiated in a microwave vessel at 80° C. for 45 minutes. In order to complete the transformation the irradiation was continued for another 45 minutes at 80° C. For the workup, the reaction mixture was quenched with a solution of citric acid (10%), then extracted with ethyl acetate (5×30 ml) followed by a 20:80-mixture of methanol and dichloromethane (200 ml). The combined organic layers were dried over sodium sulphate, evaporated at reduced pressure and, finally, lyophilized to remove residual dimethylsulphoxide. Further purification by flash chromatography on silica gel yielded the 5-cyclopropylmethoxy-pyrazine-2-carboxylic acid as an off-white solid (1.83 g, 27% of theory). MS (ISP): m/z=195 [M+H]⁺.

EXAMPLE 37

6-Chloro-pyridazine-3-carboxylic acid [3-((R)-2-amino-5,5-difluoro-4,6,6-trimethyl-5,6-dihydro-4H-[1,3]oxazin-4-yl)-4-fluoro-phenyl]-amide and example 37a) 6-Chloro-pyridazine-3-carboxylic acid [3-((R)-2-amino-5,5-difluoro-4,6,6-trimethyl-5,6-dihydro-4H-[1,3]oxazin-4-yl)-4-fluoro-phenyl]-amide hydrochloride The condensation of (R)-4-(5-amino-2-fluoro-phenyl)-5,5-difluoro-4,6,6-trimethyl-5,6-dihydro-4H-[1,3]oxazin-2-ylamine (intermediate XI-2) and 6-chloro-pyridazine-3-carboxylic acid following procedure I yielded the 6-chloro-pyridazine-3-carboxylic acid [3-((R)-2-amino-5,5-difluoro-4,6,6-trimethyl-5,6-dihydro-4H-[1,3]oxazin-4-yl)-4-fluoro-phenyl]-amide which, after treatment with hydrochloric acid in dioxane (4N), evaporation and trituration with diethylether, gave the title compound as a white solid. MS (ISP): m/z=428.2 [M+H]⁺.

EXAMPLE 38

1-Difluoromethyl-1H-pyrazole-3-carboxylic acid [3-((R)-2-amino-5,5-difluoro-4,6,6-trimethyl-5,6-dihydro-4H-[1,3]oxazin-4-yl)-4-fluoro-phenyl]-amide The condensation of (R)-4-(5-amino-2-fluoro-phenyl)-5,5-difluoro-4,6,6-trimethyl-5,6-dihydro-4H-[1,3]oxazin-2-ylamine (intermediate XI-2) and 1-difluoromethyl-1H-pyrazole-3-carboxylic acid following procedure I yielded the title compound as a white solid. MS (ISP): m/z=432.2.

EXAMPLE 39

3-Chloro-5-cyano-pyridine-2-carboxylic acid [3-((R)-2-amino-5,5-difluoro-4-methyl-5,6-dihydro-4H-[1,3]oxazin-4-yl)-4-fluoro-phenyl]-amide The condensation of (R)-4-(5-amino-2-fluoro-phenyl)-5,5-difluoro-4-methyl-5,6-dihydro-4H-[1,3]oxazin-2-ylamine (intermediate XI-1) and 3-chloro-5-cyano-pyridine-2-carboxylic acid following procedure I yielded the title compound as a white solid. MS (ISP): m/z=424.1 [M+H]⁺.

EXAMPLE 40

5-Cyclopropylethynyl-pyridine-2-carboxylic acid [3-((R)-2-amino-5,5-difluoro-4-methyl-5,6-dihydro-4H-[1,3]oxazin-4-yl)-4-fluoro-phenyl]-amide The condensation of (R)-4-(5-amino-2-fluoro-phenyl)-5,5-difluoro-4-methyl-5,6-dihydro-4H-[1,3]oxazin-2-ylamine (intermediate XI-1) and 5-cyclopropylethynyl-pyridine-2-carboxylic acid (CAS1174322-62-3, WO2009091016) following procedure I yielded the title compound as a white solid. MS (ISP): m/z=429.3 [M+H]$^+$.

EXAMPLE 41

5-Difluoromethoxy-pyridine-2-carboxylic acid [3-((R)-2-amino-5,5-difluoro-4-methyl-5,6-dihydro-4H-[1,3]oxazin-4-yl)-4-fluoro-phenyl]-amide The condensation of (R)-4-(5-amino-2-fluoro-phenyl)-5,5-difluoro-4-methyl-5,6-dihydro-4H-[1,3]oxazin-2-ylamine (intermediate XI-1) and 5-difluoromethoxy-pyridine-2-carboxylic acid (CAS1174323-34-2, WO2009091016) following procedure I yielded the title compound as a white solid. MS (ISP): m/z=431.3 [M+H]$^+$.

EXAMPLE 42

5-Fluoromethoxy-pyridine-2-carboxylic acid [3-((R)-2-amino-5,5-difluoro-4-methyl-5,6-dihydro-4H-[1,3]oxazin-4-yl)-4-fluoro-phenyl]-amide The condensation of (R)-4-(5-amino-2-fluoro-phenyl)-5,5-difluoro-4-methyl-5,6-dihydro-4H-[1,3]oxazin-2-ylamine (intermediate XI-1) and 5-fluoromethoxy-pyridine-2-carboxylic acid (CAS1174321-03-9, WO2009091016) following procedure I yielded the title compound as a colorless oil. MS (ISP): m/z=413.3 [M+H]$^+$.

EXAMPLE 43

5-(2,2,3,3-Tetrafluoro-propoxy)-pyridine-2-carboxylic acid [3-((R)-2-amino-5,5-difluoro-4-methyl-5,6-dihydro-4H-[1,3]oxazin-4-yl)-4-fluoro-phenyl]-amide The condensation of (R)-4-(5-amino-2-fluoro-phenyl)-5,5-difluoro-4-methyl-5,6-dihydro-4H-[1,3]oxazin-2-ylamine (intermediate XI-1) and 5-(2,2,3,3-tetrafluoro-propoxy)-pyridine-2-carboxylic acid [example 30a), b)] following procedure I yielded the title compound as a white solid. MS (ISP): m/z=495.2 [M+H]$^+$.

EXAMPLE 44

5-(2,2,3,3,3-Pentafluoro-propoxy)-pyridine-2-carboxylic acid [3-((R)-2-amino-5,5-difluoro-4-methyl-5,6-dihydro-4H-[1,3]oxazin-4-yl)-4-fluoro-phenyl]-amide The condensation of (R)-4-(5-amino-2-fluoro-phenyl)-5,5-difluoro-4-methyl-5,6-dihydro-4H-[1,3]oxazin-2-ylamine (intermediate XI-1) and 5-(2,2,3,3,3-pentafluoro-propoxy)-pyridine-2-carboxylic acid following procedure I yielded the title compound as a white solid. MS (ISP): m/z=513.1 [M+H]$^+$.

The 5-(2,2,3,3,3-pentafluoro-propoxy)-pyridine-2-carboxylic acid was obtained as follows:

a) In a manner analogous to that described in example 30a), the alkylation of the 5-hydroxy-pyridine-2-carboxylic acid methyl ester with potassium carbonate and trifluoro-methanesulphonic acid 2,2,3,3,3-pentafluoropropyl ester yielded the 5-(2,2,3,3,3-pentafluoro-propoxy)-pyridine-2-carboxylic acid methyl ester as a light yellow oil. MS (ISP): m/z=285 [M]$^+$.

b) In a manner analogous to that described in example 30b), the hydrolysis of the 5-(2,2,3,3,3-pentafluoro-propoxy)-pyridine-2-carboxylic acid methyl ester with lithium hydroxide yielded the 5-(2,2,3,3,3-pentafluoro-propoxy)-pyridine-2-carboxylic acid as a white solid. MS (ISP): m/z=271 [M+H]$^+$.

EXAMPLE 45

5-(2,2-Difluoro-ethoxy)-pyridine-2-carboxylic acid [3-((R)-2-amino-5,5-difluoro-4-methyl-5,6-dihydro-4H-[1,3]oxazin-4-yl)-4-fluoro-phenyl]-amide The condensation of (R)-4-(5-amino-2-fluoro-phenyl)-5,5-difluoro-4-methyl-5,6-dihydro-4H-[1,3]oxazin-2-ylamine (intermediate XI-1) and 5-(2,2-difluoro-ethoxy)-pyridine-2-carboxylic acid (CAS1097730-45-4, WO2009091016) following procedure I yielded the title compound as a white solid. MS (ISP): m/z=445.2 [M+H]$^+$.

EXAMPLE 46

5-Cyclopropylmethoxy-pyrazine-2-carboxylic acid [3-((R)-2-amino-5,5-difluoro-4-methyl-5,6-dihydro-4H-[1,3]oxazin-4-yl)-4-fluoro-phenyl]-amide The condensation of (R)-4-(5-amino-2-fluoro-phenyl)-5,5-difluoro-4-methyl-5,6-dihydro-4H-[1,3]oxazin-2-ylamine (intermediate XI-1) and 5-cyclopropylmethoxy-pyrazine-2-carboxylic acid (example 36) following procedure I yielded the title compound as a white solid. MS (ISP): m/z=436.2 [M+H]$^+$.

EXAMPLE 47

5-Chloro-pyrazine-2-carboxylic acid [3-((R)-2-amino-5,5-difluoro-4-methyl-5,6-dihydro-4H-[1,3]oxazin-4-yl)-4-fluoro-phenyl]-amide The condensation of (R)-4-(5-amino-2-fluoro-phenyl)-5,5-difluoro-4-methyl-5,6-dihydro-4H-[1,3]oxazin-2-ylamine (intermediate XI-1) and 5-chloro-pyrazine-2-carboxylic acid following procedure I yielded the title compound as a white solid. MS (ISP): m/z=400.1 [M+H]$^+$.

EXAMPLE 48

3,5-Dichloro-pyrazine-2-carboxylic acid [3-((R)-2-amino-5,5-difluoro-4-methyl-5,6-dihydro-4H-[1,3]oxazin-4-yl)-4-fluoro-phenyl]-amide The condensation of (R)-4-(5-amino-2-fluoro-phenyl)-5,5-difluoro-4-methyl-5,6-dihydro-4H-[1,3]oxazin-2-ylamine (intermediate XI-1) and 3,5-dichloro-pyrazine-2-carboxylic acid following procedure I yielded the title compound as a white solid. MS (ISP): m/z=434.1 [M+H]$^+$, 436.1 [M+2+H]$^+$.

EXAMPLE 49

5-Cyano-pyridine-2-carboxylic acid [3-((R)-2-amino-5,5-difluoro-4-methyl-5,6-dihydro-4H-[1,3]oxazin-4-yl)-4,5-difluoro-phenyl]-amide The condensation of (R)-4-(5-amino-2,3-difluoro-phenyl)-5,5-difluoro-4-methyl-5,6-dihydro-4H-[1,3]oxazin-2-ylamine (intermediate XI-2) and 5-cyano-pyridine-2-carboxylic acid following procedure I yielded the title compound as a light yellow solid. MS (ISP): m/z=408.3 [M+H]$^+$.

EXAMPLE 50

5-Chloro-pyridine-2-carboxylic acid [3-((R)-2-amino-5,5-difluoro-4-methyl-5,6-dihydro-4H-[1,3]oxazin-4-yl)-4-chloro-phenyl]-amide The condensation of (R)-4-(5-amino-2-chloro-phenyl)-5,5-difluoro-4-methyl-5,6-dihydro-4H-[1,3]oxazin-2-ylamine (intermediate XI-3) and 5-chloro-pyridine-2-carboxylic acid following procedure I yielded the title compound as an off-white solid. MS (ISP): m/z=415.2 [M+H]$^+$, 417.1 [M+2+H]$^+$.

EXAMPLE 51

5-Cyano-pyridine-2-carboxylic acid [3-((R)-2-amino-5,5-difluoro-4-methyl-5,6-dihydro-4H-[1,3]oxazin-4-yl)-4-chloro-phenyl]-amide The condensation of (R)-4-(5-amino-2-chloro-phenyl)-5,5-difluoro-4-methyl-5,6-dihydro-4H-[1,3]oxazin-2-ylamine (intermediate XI-3) and 5-cyano-pyridine-2-carboxylic acid following procedure I yielded the title compound as an off-white solid. MS (ISP): m/z=406.3 [M+H]$^+$.

EXAMPLE 52

5-Chloro-pyridine-2-carboxylic acid [3-((R)-2-amino-5,5-difluoro-4-methyl-5,6-dihydro-4H-[1,3]oxazin-4-yl)-phenyl]-amide The condensation of (R)-4-(3-amino-phenyl)-5,5-difluoro-4-methyl-5,6-dihydro-4H-[1,3]oxazin-2-ylamine (intermediate XI-4) and 5-chloro-pyridine-2-carboxylic acid following procedure I yielded the title compound as an off-white solid. MS (ISP): m/z=381.2 [M+H]$^+$.

EXAMPLE 53

5-Cyano-pyridine-2-carboxylic acid [3-((R)-2-amino-5,5-difluoro-4-methyl-5,6-dihydro-4H-[1,3]oxazin-4-yl)-phenyl]-amide The condensation of (R)-4-(3-amino-phenyl)-5,5-difluoro-4-methyl-5,6-dihydro-4H-[1,3]oxazin-2-ylamine (intermediate XI-4) and 5-cyano-pyridine-2-carboxylic acid following procedure I yielded the title compound as an off-white solid. MS (ISP): m/z=372.1 [M+H]$^+$.

EXAMPLE 54

3-(2,2,2-Trifluoro-ethoxy)-pyridine-2-carboxylic acid [3-((R)-2-amino-5,5-difluoro-4-methyl-5,6-dihydro-4H-[1,3]oxazin-4-yl)-4-fluoro-phenyl]-amide The condensation of (R)-4-(5-amino-2-fluoro-phenyl)-5,5-difluoro-4-methyl-5,6-dihydro-4H-[1,3]oxazin-2-ylamine (intermediate XI-1) and 3-(2,2,2-trifluoro-ethoxy)-pyridine-2-carboxylic acid following procedure I yielded the title compound. MS (ISP): m/z=463.1 [M+H]$^+$. The 3-(2,2,2-trifluoro-ethoxy)-pyridine-2-carboxylic acid was prepared as follows:
a) To a solution of 3-hydroxy-pyridine-2-carboxylic acid methyl ester (200 mg, 1.3 mmol) in N,N-dimethylformamide (2.0 ml) was added at 22° C. sodium hydride (55% in oil, 64 mg) and stirring was continued until gas evolution ceased. The suspension was cooled to 0° C. and treated with trifluoroethyl trifluormethanesulfonate (728 mg) and stirring was continued at 22° C. for 2 hours. The mixture was partitioned between saturated sodium hydrogen-carbonate solution and ethyl acetate, and the organic layer was dried and evaporated. The residue was purified by chromatography on silica using n-heptane and ethyl acetate (3:1) as the eluent to give 3-(2,2,2-trifluoro-ethoxy)-pyridine-2-carboxylic acid methyl ester as a pale green oil. Mass (calculated) $C_9H_8F_3NO_3$ [235.16]; (found) [M+H]$^+$=236.
b) A solution of 3-(2,2,2-trifluoro-ethoxy)-pyridine-2-carboxylic acid methyl ester (216 mg, 0.9 mmol) in methanol (1 ml) was treated with a solution of lithium hydroxide (78 mg, 3.3 mmol) in water (0.1 ml) and stirring was continued at 22° C. for 2 hours. The solution was evaporated and the residue triturated with 1N aqueous hydrochloric acid. The suspension was filtered, the residue washed with water and dried to give 3-(2,2,2-trifluoro-ethoxy)-pyridine-2-carboxylic acid as a colorless solid. Mass (calculated) $C_8H_6F_3NO_3$ [221.14]; (found) [M−H]$^-$=220.

EXAMPLE 55

Oxazole-4-carboxylic acid [3-((R)-2-amino-5,5-difluoro-4-methyl-5,6-dihydro-4H-[1,3]oxazin-4-yl)-4-fluoro-phenyl]-amide The condensation of (R)-4-(5-amino-2-fluoro-phenyl)-5,5-difluoro-4-methyl-5,6-dihydro-4H-[1,3]oxazin-2-ylamine (intermediate XI-1) and oxazole-4-carboxylic acid following procedure I yielded the title compound as a white solid. MS (ISP): m/z=353.3 [M−H]$^-$.

EXAMPLE 56

2-Ethyl-oxazole-4-carboxylic acid [3-((R)-2-amino-5,5-difluoro-4-methyl-5,6-dihydro-4H-[1,3]oxazin-4-yl)-4-fluoro-phenyl]-amide The condensation of (R)-4-(5-amino-2-fluoro-phenyl)-5,5-difluoro-4-methyl-5,6-dihydro-4H-[1,3]oxazin-2-ylamine (intermediate XI-1) and 2-ethyl-oxazole-4-carboxylic acid following procedure I yielded the title compound as a brown oil. MS (ISP): m/z=383.3 [M+H]$^+$.

EXAMPLE 57

2-Chloromethyl-oxazole-4-carboxylic acid [3-((R)-2-amino-5,5-difluoro-4-methyl-5,6-dihydro-4H-[1,3]oxazin-4-yl)-4-fluoro-phenyl]-amide The condensation of (R)-4-(5-amino-2-fluoro-phenyl)-5,5-difluoro-4-methyl-5,6-dihydro-4H-[1,3]oxazin-2-ylamine (intermediate XI-1) and 2-chloromethyl-oxazole-4-carboxylic acid following procedure I yielded the title compound as a colorless viscous oil. MS (ISP): m/z=403.3 [M+H]$^+$.

EXAMPLE 58

2-Methyl-oxazole-4-carboxylic acid [3-((R)-2-amino-5,5-difluoro-4-methyl-5,6-dihydro-4H-[1,3]oxazin-4-yl)-4-fluoro-phenyl]-amide The condensation of (R)-4-(5-amino-2-fluoro-phenyl)-5,5-difluoro-4-methyl-5,6-dihydro-4H-[1,3]oxazin-2-ylamine (intermediate XI-1) and 2-methyl-oxazole-4-carboxylic acid following procedure I yielded the title compound as a white solid. MS (ISP): m/z=369.1 [M+H]$^+$.

EXAMPLE 59

2,5-Dimethyl-oxazole-4-carboxylic acid [3-((R)-2-amino-5,5-difluoro-4-methyl-5,6-dihydro-4H-[1,3]oxazin-4-yl)-4-fluoro-phenyl]-amide The condensation of (R)-4-(5-amino-2-fluoro-phenyl)-5,5-difluoro-4-methyl-5,6-dihydro-4H-[1,3]oxazin-2-ylamine (intermediate XI-1) and 2,5-dimethyl-oxazole-4-carboxylic acid following procedure I yielded the title compound as a white solid. MS (ISP): m/z=383.2 [M+H]$^+$.

EXAMPLE 60

2-Methyl-5-trifluoromethyl-oxazole-4-carboxylic acid [3-((R)-2-amino-5,5-difluoro-4-methyl-5,6-dihydro-4H-[1,3]oxazin-4-yl)-4-fluoro-phenyl]-amide The condensation of (R)-4-(5-amino-2-fluoro-phenyl)-5,5-difluoro-4-methyl-5,6-dihydro-4H-[1,3]oxazin-2-ylamine (intermediate XI-1) and 2-methyl-5-trifluoromethyl-oxazole-4-carboxylic acid following procedure I yielded the title compound as a colorless foam. MS (ISP): m/z=437.1 [M+H]$^+$.

EXAMPLE 61

4-Methyl-isoxazole-3-carboxylic acid [3-((R)-2-amino-5,5-difluoro-4-methyl-5,6-dihydro-4H-[1,3]oxazin-4-yl)-4-fluoro-phenyl]-amide The condensation of (R)-4-(5-amino-2-fluoro-phenyl)-5,5-difluoro-4-methyl-5,6-dihydro-4H-[1,3]oxazin-2-ylamine (intermediate XI-1) and 4-methyl-isoxazole-3-carboxylic acid following procedure I yielded the title compound as a white solid. MS (ISP): m/z=369.2 [M+H]$^+$.

EXAMPLE 62

5-Isopropyl-oxazole-4-carboxylic acid [3-((R)-2-amino-5,5-difluoro-4-methyl-5,6-dihydro-4H-[1,3]oxazin-4-yl)-4-fluoro-phenyl]-amide The condensation of (R)-4-(5-amino-2-fluoro-phenyl)-5,5-difluoro-4-methyl-5,6-dihydro-4H-[1,3]oxazin-2-ylamine (intermediate XI-1) and 5-isopropyl-oxazole-4-carboxylic acid following procedure I yielded the title compound as a white solid. MS (ISP): m/z=397.2 [M+H]$^+$.

EXAMPLE 63

1-Methyl-1H-pyrazole-3-carboxylic acid [3-((R)-2-amino-5,5-difluoro-4-methyl-5,6-dihydro-4H-[1,3]oxazin-4-yl)-4-fluoro-phenyl]-amide The condensation of (R)-4-(5-amino-2-fluoro-phenyl)-5,5-difluoro-4-methyl-5,6-dihydro-4H-[1,3]oxazin-2-ylamine (intermediate XI-1) and 1-methyl-1H-pyrazole-3-carboxylic acid following procedure I yielded the title compound as a white solid. MS (ISP): m/z=368.1 [M+H]$^+$.

EXAMPLE 64

1-Difluoromethyl-1H-pyrazole-3-carboxylic acid [3-((R)-2-amino-5,5-difluoro-4-methyl-5,6-dihydro-4H-[1,3]oxazin-4-yl)-4-fluoro-phenyl]-amide The condensation of (R)-4-(5-amino-2-fluoro-phenyl)-5,5-difluoro-4-methyl-5,6-dihydro-4H-[1,3]oxazin-2-ylamine (intermediate XI-1) and 1-difluoromethyl-1H-pyrazole-3-carboxylic acid following procedure I yielded the title compound as a white solid. MS (ISP): m/z=404.3 [M+H]$^+$.

EXAMPLE 65

4-Chloro-2H-pyrazole-3-carboxylic acid [3-((R)-2-amino-5,5-difluoro-4-methyl-5,6-dihydro-4H-[1,3]oxazin-4-yl)-4-fluoro-phenyl]-amide The condensation of (R)-4-(5-amino-2-fluoro-phenyl)-5,5-difluoro-4-methyl-5,6-dihydro-4H-[1,3]oxazin-2-ylamine (intermediate XI-1) and 4-chloro-2H-pyrazole-3-carboxylic acid following procedure I yielded the title compound. MS (ISP): m/z=388.1 [M+H]$^+$.

EXAMPLE 66

4-Methyl-2H-pyrazole-3-carboxylic acid [3-((R)-2-amino-5,5-difluoro-4-methyl-5,6-dihydro-4H-[1,3]oxazin-4-yl)-4-fluoro-phenyl]-amide The condensation of (R)-4-(5-amino-2-fluoro-phenyl)-5,5-difluoro-4-methyl-5,6-dihydro-4H-[1,3]oxazin-2-ylamine (intermediate XI-1) and 4-methyl-2H-pyrazole-3-carboxylic acid (CAS82231-51-4; B. Pelcman et al., WO2006032851) following procedure I yielded the title compound as a white solid. MS (ISP): m/z=368.1 [M+H]$^+$.

EXAMPLE 67

4-Chloro-5-cyclopropyl-2H-pyrazole-3-carboxylic acid [3-((R)-2-amino-5,5-difluoro-4-methyl-5,6-dihydro-4H-[1,3]oxazin-4-yl)-4-fluoro-phenyl]-amide The condensation of (R)-4-(5-amino-2-fluoro-phenyl)-5,5-difluoro-4-methyl-5,6-dihydro-4H-[1,3]oxazin-2-ylamine (intermediate XI-1) and 4-chloro-5-cyclopropyl-2H-pyrazole-3-carboxylic acid following procedure I yielded the title compound as a white foam. MS (ISP): m/z=428.3 [M+H]$^+$.

The 4-chloro-5-cyclopropyl-2H-pyrazole-3-carboxylic acid was obtained as follows:

a) To a solution of 5-cyclopropyl-2H-pyrazole-3-carboxylic acid ethyl ester (202 mg) in N,N-dimethylformamide (4 ml) was added at 0° C. N-chlorosuccinimide (199 mg) and stirring was continued at 22° C. for 15 hours. For the workup, The mixture was partitioned between water and ethyl acetate, the organic layer was dried, evaporated and the residue purified by chromatography on silica using a 8:1-mixture of n-heptane and ethyl acetate as the eluent to give 4-chloro-5-cyclopropyl-2H-pyrazole-3-carboxylic acid ethyl ester (215 mg) as a pale yellow liquid. MS (ISP): m/z=215.2 [M+H]$^+$.

b) To a solution of 4-chloro-5-cyclopropyl-2H-pyrazole-3-carboxylic acid ethyl ester (210 mg) in dioxane (4 ml) was added at 22° C. a solution of sodium hydroxide (3.0 M, 0.65 ml), and stirring was continued at 22° C. for 15 hours and at 60° C. for 3 hours. For the workup, the mixture was partitioned between aqueous hydrochloric acid (1.0 M) and ethyl acetate, the organic layer was dried and evaporated to give the title compound (161 mg) as a pale yellow solid. MS (ISP): m/z=184.8 [M–H]$^-$.

EXAMPLE 68

4-Chloro-1-(2,2-difluoro-ethyl)-1H-pyrazole-3-carboxylic acid [3-((R)-2-amino-5,5-difluoro-4-methyl-5,6-dihydro-4H-[1,3]oxazin-4-yl)-4-fluoro-phenyl]-amide The condensation of (R)-4-(5-amino-2-fluoro-phenyl)-5,5-difluoro-4-methyl-5,6-dihydro-4H-[1,3]oxazin-2-ylamine (intermediate XI-1) and 4-chloro-1-(2,2-difluoro-ethyl)-1H-pyrazole-3-carboxylic acid following procedure I yielded the title compound. MS (ISP): m/z=452.1 [M+H]$^+$.

EXAMPLE 69

5-Ethyl-oxazole-4-carboxylic acid [3-((R)-2-amino-5,5-difluoro-4,6,6-trimethyl-5,6-dihydro-4H-[1,3] oxazin-4-yl)-4-fluoro-phenyl]-amide formate The condensation of (R)-4-(5-amino-2-fluoro-phenyl)-5,5-difluoro-4-methyl-5,6-dihydro-4H-[1,3]oxazin-2-ylamine (intermediate XI-1) and 5-ethyl-oxazole-4-carboxylic acid (CAS898227-93-5) following procedure I yielded the title compound after purification on preparative HPLC as a colorless foam. MS (ISP): m/z=383.1 [M+H]$^+$.

EXAMPLE 70

5-Cyclopropyl-oxazole-4-carboxylic acid [3-((R)-2-amino-5,5-difluoro-4,6,6-trimethyl-5,6-dihydro-4H-[1,3]oxazin-4-yl)-4-fluoro-phenyl]-amide formate The condensation of (R)-4-(5-amino-2-fluoro-phenyl)-5,5-difluoro-4-methyl-5,6-dihydro-4H-[1,3]oxazin-2-ylamine (intermediate XI-1) and 5-cyclopropyl-oxazole-4-carboxylic acid (CAS917828-31-0) following procedure I yielded the title compound after purification on preparative HPLC as a colorless foam. MS (ISP): m/z=395.1 [M+H]$^+$.

EXAMPLE 71

4-Chloro-1-difluoromethyl-1H-pyrazole-3-carboxylic acid [3-((R)-2-amino-5,5-difluoro-4,6,6-trimethyl-5,6-dihydro-4H-[1,3]oxazin-4-yl)-4-fluoro-phenyl]-amide The condensation of (R)-4-(5-amino-2-fluoro-phenyl)-5,5-difluoro-4-methyl-5,6-dihydro-4H-[1,3]oxazin-2-ylamine (intermediate XI-1) and 4-chloro-1-difluoromethyl-1H-pyrazole-3-carboxylic acid (CAS917828-31-0) following procedure I yielded the title compound as a white solid. MS (ISP): m/z=438.1 [M+H]$^+$.

The 4-chloro-1-difluoromethyl-1H-pyrazole-3-carboxylic acid was obtained as follows:
a) 1-Difluoromethyl-1H-pyrazole-3-carboxylic acid methyl ester
A solution of 1-difluoromethyl-1H-pyrazole-3-carboxylic acid (CAS925179-02-8) (500 mg, 3.1 mmol) in methanol (18 ml) was cooled to 0° C. and treated with sulphuric acid (98%, 0.2 ml, 3.1 mmol). The mixture was heated to reflux for 2 hours. For the workup, the solution was cooled and concentrated at reduced pressure. The residue was partitioned between ethyl acetate (25 ml) and water (30 ml). The organic layer was separated, washed with water until the water phase showed a neutral pH. After drying over sodium sulphate, the organic layer was evaporated at reduced pressure. The 1-difluoromethyl-1H-pyrazole-3-carboxylic acid methyl ester was obtained as a colorless liquid (535 mg, 99% of theory) pure enough to be engaged in the next step without further purification. MS (ISP): m/z=177.1 [M+H]$^+$.
b) 4-Chloro-1-difluoromethyl-1H-pyrazole-3-carboxylic acid methyl ester
A mixture of 1-difluoromethyl-1H-pyrazole-3-carboxylic acid methyl ester (535 mg, 3 mmol) and N-chloro-succinimide (1.22 g, 9.1 mmol) in N,N-dimethylformamide (5 ml) was heated at 50° C. overnight. The reaction mixture was cooled, poured into water (20 ml), then extracted with ethyl acetate. The organic layer was separated, washed with water, dried over sodium sulphate, finally evaporated at reduced pressure. The yellowish crude material was purified by chromatography on silica gel using a 3:1-mixture of cyclohexane and ethyl acetate as the eluent. The 4-chloro-1-difluoromethyl-1H-pyrazole-3-carboxylic acid methyl ester was obtained as a white solid (540 mg, 84% of theory). MS (ISP): m/z=209.9 [M]$^+$.
c) 4-Chloro-1-difluoromethyl-1H-pyrazole-3-carboxylic acid
A solution of 4-chloro-1-difluoromethyl-1H-pyrazole-3-carboxylic acid methyl ester (540 mg, 2.6 mmol) in tetrahydrofuran (18 ml) was treated at room temperature with a solution of lithium hydroxide (135 mg, 5.6 mmol) in a 1:1-mixture of water and methanol (12 ml). After 1 hour the reaction was complete, and the solvents were evaporated at reduced pressure. The residue was dissolved in water (10 ml) and acidified with hydrochloric acid (2M). Extraction with ethyl acetate, drying of the organic layer over sodium sulphate, and evaporation at reduced pressure yielded a white solid (555 mg) which was triturated with pentane (10 ml). The solid material was filtered, washed with pentane and dried. After drying at reduced pressure the 4-chloro-1-difluoromethyl-1H-pyrazole-3-carboxylic acid was obtained as a white solid (477 mg, 95% of theory). MS (ISP): m/z=195.0 [M–H]$^-$.

EXAMPLE 72

Pyridine-2,5-dicarboxylic acid 5-amide 2-{[3-((R)-2-amino-5,5-difluoro-4,6,6-trimethyl-5,6-dihydro-4H-[1,3]oxazin-4-yl)-4-fluoro-phenyl]-amide}

The condensation of (R)-4-(5-amino-2-fluoro-phenyl)-5,5-difluoro-4-methyl-5,6-dihydro-4H-[1,3]oxazin-2-ylamine (intermediate XI-1) and 5-carbamoyl-pyridine-2-carboxylic acid following procedure I yielded the title compound as a white solid. MS (ISP): m/z=408.3 [M+H]$^+$.

EXAMPLE 73

N-[3-((R)-2-Amino-5,5-difluoro-4-methyl-5,6-dihydro-4H-[1,3]oxazin-4-yl)-4-fluoro-phenyl]-acetamide The condensation of (R)-4-(5-amino-2-fluoro-phenyl)-5,5-difluoro-4-methyl-5,6-dihydro-4H-[1,3]oxazin-2-ylamine (intermediate XI-1) and acetic acid following procedure I yielded the title compound as a white solid. MS (ISP): m/z=302.3 [M+H]$^+$.

EXAMPLE 74

(RS)-2,2-Difluoro-cyclopropanecarboxylic acid [3-((R)-2-amino-5,5-difluoro-4-methyl-5,6-dihydro-4H-[1,3]oxazin-4-yl)-4-fluoro-phenyl]-amide The condensation of (R)-4-(5-amino-2-fluoro-phenyl)-5,5-difluoro-4-methyl-5,6-dihydro-4H-[1,3]oxazin-2-ylamine (intermediate XI-1) and (RS)-2,2-difluoro-cyclopropanecarboxylic acid following procedure I yielded the title compound as a colorless solid. MS (ISP): m/z=364.2 [M+H]$^+$.

EXAMPLE 75

1-Trifluoromethyl-cyclopropanecarboxylic acid [3-((R)-2-amino-5,5-difluoro-4-methyl-5,6-dihydro-4H-[1,3]oxazin-4-yl)-4-fluoro-phenyl]-amide The condensation of (R)-4-(5-amino-2-fluoro-phenyl)-5,5-difluoro-4-methyl-5,6-dihydro-4H-[1,3]oxazin-2-ylamine (intermediate XI-1) and 1-trifluoromethyl-cyclopropanecarboxylic acid following procedure I yielded the title compound as a colorless solid. MS (ISP): m/z=396.1 [M+H]$^+$.

EXAMPLE 76

(R)—N-[3-((R)-2-Amino-5,5-difluoro-4-methyl-5,6-dihydro-4H-[1,3]oxazin-4-yl)-4-fluoro-phenyl]-3,3,3-trifluoro-2-hydroxy-2-methyl-propionamide 2,2,2-trifluoroacetate a) {(R)-5,5-Difluoro-4-[2-fluoro-5-((R)-3,3,3-trifluoro-2-hydroxy-2-methyl-propionylamino)-phenyl]-4-methyl-5,6-dihydro-4H-[1,3]oxazin-2-yl}-carbamic acid tert-butyl ester
A solution of (R)-3,3,3-trifluoro-2-hydroxy-2-methyl-propionic acid (CAS44864-47-3) (20 mg, 0.125 mmol) in N,N-dimethylformamide (1 ml), O-(7-azabenzotriazol-1-yl)-N,N,N',N'-tetramethyluronium-hexafluorophosphate (HATU) (66 mg, 0.167 mmol) and diisopropylethylamine (35 mg, 0.267 mmol) was stirred at room temperature for 45 minutes. Thereafter, [(R)-4-(5-amino-2-fluoro-phenyl)-5,5-difluoro-4-methyl-5,6-dihydro-4H-[1,3]oxazin-2-yl]-carbamic acid tert-butyl ester (30 mg, 0.063 mmol) (intermediate XXV-1) was added and stirring continued at room temperature overnight. For the workup, formic acid was added to the incomplete reaction, the mixture was divided in two portions and directly injected on a preparative HPLC column using a gradient of water (+0.1% of formic acid)/acetonitrile=90:10 to 5:95 as the eluent. The {(R)-5,5-difluoro-4-[2-fluoro-5-((R)-3,3,3-trifluoro-2-hydroxy-2-methyl-propionylamino)-phenyl]-4-methyl-5,6-dihydro-4H-[1,3]oxazin-2-yl}-carbamic acid tert-butyl ester was obtained as a colorless, amorphous solid (8 mg, 25% of theory). MS (ISP): m/z=500.2 [M+H]$^+$.
b) (R)—N-[3-((R)-2-Amino-5,5-difluoro-4-methyl-5,6-dihydro-4H-[1,3]oxazin-4-yl)-4-fluoro-phenyl]-3,3,3-trifluoro-2-hydroxy-2-methyl-propionamide 2,2,2-trifluoroacetate
A solution of the {(R)-5,5-difluoro-4-[2-fluoro-5-((R)-3,3,3-trifluoro-2-hydroxy-2-methyl-propionyl-amino)-phenyl]-4-methyl-5,6-dihydro-4H-[1,3]oxazin-2-yl}-carbamic acid tert-butyl ester (8 mg, 0.016 mmol) in 2,2,2-trifluoroacetic acid was stirred at room temperature during 1 hour. Thereafter, the reaction mixture was evaporated at reduced pressure and kept under high vacuum overnight to yield the title compound as yellow oil in quantitative yield. MS (ISP): m/z=400.1 [M+H]$^+$.

EXAMPLE 77

4-Chloro-1-ethyl-1H-pyrazole-3-carboxylic acid [3-((R)-2-amino-5,5-difluoro-4-methyl-5,6-dihydro-4H-[1,3]oxazin-4-yl)-4-fluoro-phenyl]-amide The condensation of (R)-4-(5-amino-2-fluoro-phenyl)-5,5-difluoro-4-methyl-5,6-dihydro-4H-[1,3]oxazin-2-ylamine (intermediate XI-1) and 4-chloro-1-ethyl-1H-pyrazole-3-carboxylic acid (CAS512810-20-7) following procedure I yielded the title compound as a white solid. MS (ISP): m/z=416.3 [M+H]$^+$.

EXAMPLE 78

4-Chloro-1-(2,2,2-trifluoro-ethyl)-1H-pyrazole-3-carboxylic acid [3-((R)-2-amino-5,5-difluoro-4-methyl-5,6-dihydro-4H-[1,3]oxazin-4-yl)-4-fluoro-phenyl]-amide The condensation of (R)-4-(5-amino-2-fluoro-phenyl)-5,5-difluoro-4-methyl-5,6-dihydro-4H-[1,3]oxazin-2-ylamine (intermediate XI-1) and 4-chloro-1-(2,2,2-trifluoro-ethyl)-1H-pyrazole-3-carboxylic acid (CAS1006448-63-0) following procedure I yielded the title compound as a white solid. MS (ISP): m/z=470.2 [M+H]$^+$.

EXAMPLE 79

2-Fluoromethyl-oxazole-4-carboxylic acid [3-((R)-2-amino-5,5-difluoro-4-methyl-5,6-dihydro-4H-[1,3]oxazin-4-yl)-4-fluoro-phenyl]-amide formate The condensation of (R)-4-(5-amino-2-fluoro-phenyl)-5,5-difluoro-4-methyl-5,6-dihydro-4H-[1,3]oxazin-2-ylamine (intermediate XI-1) and 2-fluoromethyl-oxazole-4-carboxylic acid following procedure I yielded the title compound after purification by preparative HPLC as a white solid. MS (ISP): m/z=387.1 [M+H]$^+$.

The 2-fluoromethyl-oxazole-4-carboxylic acid was obtained as follows:

a) 2-Fluoromethyl-oxazole-4-carboxylic acid methyl ester
A solution of methyl 2-(chloromethyl)oxazole-4-carboxylate (CAS208465-72-9) (150 mg, 0.85 mmol) in acetonitrile (4.27 ml) was treated with tetra-n-butylammonium fluoride (2.56 ml, 2.56 mmol). The blue solution turned to orange and was left under stirring at room temperature overnight. For the workup, the reaction mixture was poured in water and extracted two times with ethyl acetate. The combined organic layers were washed with brine, dried over sodium sulphate, and concentrated at reduced pressure. The crude material was purified by chromatography on a flash NH$_2$ column using a gradient of heptane/ethyl acetate=100/0 to 50/50 as the eluent. The 2-fluoromethyl-oxazole-4-carboxylic acid methyl ester was obtained as a white solid (64 mg, 47% of theory). MS (ISP): m/z=160.1 [M+H]$^+$.

b) 2-Fluoromethyl-oxazole-4-carboxylic acid
In a manner analogous to that described in example 71c), the hydrolysis of the 2-fluoromethyl-oxazole-4-carboxylic acid methyl ester with lithium hydroxide yielded the title compound as a white solid (70% of theory). MS (ISP): m/z=144.1 [M−H]$^−$.

EXAMPLE 80

Furan-2-carboxylic acid [3-((R)-2-amino-5,5-difluoro-4-methyl-5,6-dihydro-4H-[1,3]oxazin-4-yl)-4-fluoro-phenyl]-amide The condensation of (R)-4-(5-amino-2-fluoro-phenyl)-5,5-difluoro-4-methyl-5,6-dihydro-4H-[1,3]oxazin-2-ylamine (intermediate XI-1) and furan-2-carboxylic acid following procedure I yielded the title compound after purification by preparative HPLC. MS (ISP): m/z=354.4 [M+H]$^+$.

EXAMPLE 81

5-Nitro-furan-2-carboxylic acid [3-((R)-2-amino-5,5-difluoro-4-methyl-5,6-dihydro-4H-[1,3]oxazin-4-yl)-4-fluoro-phenyl]-amide The condensation of (R)-4-(5-amino-2-fluoro-phenyl)-5,5-difluoro-4-methyl-5,6-dihydro-4H-[1,3]oxazin-2-ylamine (intermediate XI-1) and 5-nitro-furan-2-carboxylic acid (CAS645-12-5) following procedure I yielded the title compound after purification by preparative HPLC. MS (ISP): m/z=399.3 [M+H]$^+$.

EXAMPLE 82

(E)-N-[3-((R)-2-Amino-5,5-difluoro-4-methyl-5,6-dihydro-4H-[1,3]oxazin-4-yl)-4-fluoro-phenyl]-3-furan-2-yl-acrylamide The condensation of (R)-4-(5-amino-2-fluoro-phenyl)-5,5-difluoro-4-methyl-5,6-dihydro-4H-[1,3]oxazin-2-ylamine (intermediate XI-1) and (E)-3-furan-2-yl-acrylic acid following procedure I yielded the title compound after purification by preparative HPLC. MS (ISP): m/z=380.1 [M+H]$^+$.

EXAMPLE 83

5-Cyano-1-oxy-pyridine-2-carboxylic acid [3-((R)-2-amino-5,5-difluoro-4-methyl-5,6-dihydro-4H-[1,3]oxazin-4-yl)-4-fluoro-phenyl]-amide The condensation of (R)-4-(5-amino-2-fluoro-phenyl)-5,5-difluoro-4-methyl-5,6-dihydro-4H-[1,3]oxazin-2-ylamine (intermediate XI-1) and 5-cyano-1-oxy-pyridine-2-carboxylic acid following procedure I yielded the title compound as a light yellow solid. MS (ISP): m/z=406.2 [M+H]$^+$.

The 5-cyano-1-oxy-pyridine-2-carboxylic acid was obtained as follows:
A suspension of 5-cyano-pyridine-2-carboxylic acid (100 mg, 0.68 mmol) in acetonitrile (1.5 ml) was cooled to 0° C., then treated with urea hydrogen peroxide (133 mg, 1.42 mmol) and trifluoroacetic acid anhydride (289 mg, 1.38 mmol) during 64 hours at 0-4° C. For the workup, the reaction mixture was poured into a solution of sodium thiosulphate (10% in water, 10 ml) and stirred during 10 minutes. After dilution with water the mixture was filtrated and the residue washed with water. The combined aqueous layers were filtrated again, then extracted three times with dichloromethane. The combined organic layers were dried over sodium sulphate and evaporated and yielded the 5-cyano-pyridine-2-carboxylic acid as an off-white solid (42 mg, 38% of theory). Further extraction of the aqueous layer with a 9:1-mixture of dichloromethane and ethanol yielded after drying over sodium sulphate and evaporation another pure fraction of the title compound as a white solid (11 mg, 10% of theory). MS (ISP): m/z=165.2 [M+H]$^+$.

The invention claimed is:
1. A compound of formula I,

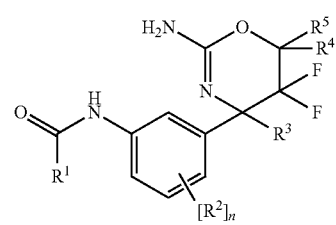

wherein
R$^1$ is selected from the group consisting of
  i) aryl,
  ii) aryl substituted by 1-4 substituents individually selected from cyano, cyano-lower alkyl, halogen, halogen-lower alkoxy, halogen-lower alkyl, lower alkoxy, lower alkoxy-lower alkyl and lower alkyl,
  iii) heteroaryl,
  iv) heteroaryl substituted by 1-4 substituents individually selected from amido, cyano, cyano-lower alkyl, cycloalkyl, cycloalkyl-lower alkenyl, cycloalkyl-lower alkynyl, cycloalkyl-lower alkyl, cycloalkyl-lower alkoxy, halogen, halogen-lower alkoxy, halogen-lower alkyl, lower alkoxy, lower alkoxy-lower alkyl, lower alkenyl, lower alkynyl, lower alkyl and nitro;
  v) lower alkyl,
  vi) lower alkyl substituted by 1-5 substituents individually selected from cyano, halogen, hydroxy and lower alkoxy;
  vii) lower alkenyl,
  viii) lower alkenyl substituted by 1-4 substituents individually selected from cyano, cyano-lower alkyl, halogen, halogen-lower alkoxy, halogen-lower alkyl, heteroaryl, lower alkoxy, lower alkoxy-lower alkyl and lower alkyl,
  ix) cycloalkyl, and
  x) cycloalkyl substituted by 1-4 substituents individually selected from cyano, cyano-lower alkyl, halogen, halogen-lower alkoxy, halogen-lower alkyl, lower alkoxy, lower alkoxy-lower alkyl and lower alkyl,
R$^2$ is selected from the group consisting of
  i) hydrogen,
  ii) halogen, and
  iii) lower alkyl;
R$^3$ is lower alkyl;
R$^4$ is selected from the group consisting of
  i) hydrogen, and
  ii) lower alkyl;
R$^5$ is selected from the group consisting of
  i) hydrogen, and
  ii) lower alkyl; and
n is 0, 1 or 2;
or a pharmaceutically acceptable salt thereof.
2. The compound of claim 1, wherein
R$^1$ is selected from the group consisting of
  i) heteroaryl,
  ii) heteroaryl substituted by 1-4 substituents individually selected from amido, cyano, cyano-lower alkyl, cycloalkyl, cycloalkyl-lower alkenyl, cycloalkyl-lower alkynyl, cycloalkyl-lower alkyl, cycloalkyl-lower alkoxy, halogen, halogen-lower alkoxy, halogen-lower alkyl, lower alkoxy, lower alkoxy-lower alkyl, lower alkenyl, lower alkynyl, lower alkyl and nitro;
iii) lower alkyl,
iv) lower alkyl substituted by 1-5 substituents individually selected from cyano, halogen, hydroxy and lower alkoxy;
v) lower alkenyl,
vi) lower alkenyl substituted by 1-4 substituents individually selected from cyano, cyano-lower alkyl, halogen, halogen-lower alkoxy, halogen-lower alkyl, heteroaryl, lower alkoxy, lower alkoxy-lower alkyl and lower alkyl,
vii) cycloalkyl, and
viii) cycloalkyl substituted by 1-4 substituents individually selected from cyano, cyano-lower alkyl, halogen, halogen-lower alkoxy, halogen-lower alkyl, lower alkoxy, lower alkoxy-lower alkyl and lower alkyl,
$R^2$ is selected from the group consisting of
i) hydrogen,
ii) halogen, and
iii) lower alkyl;
$R^3$ is lower alkyl;
$R^4$ is selected from the group consisting of
i) hydrogen, and
ii) lower alkyl;
$R^5$ is selected from the group consisting of
i) hydrogen, and
ii) lower alkyl; and
n is 0, 1 or 2;
or a pharmaceutically acceptable salt thereof.

3. The compound of claim 1, having formula Ia

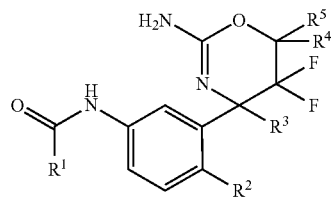

wherein
$R^1$ is selected from the group consisting of
i) aryl,
ii) aryl substituted by 1-4 substituents individually selected from cyano, cyano-lower alkyl, halogen, halogen-lower alkoxy, halogen-lower alkyl, lower alkoxy, lower alkoxy-lower alkyl and lower alkyl,
iii) heteroaryl, and
iv) heteroaryl substituted by 1-4 substituents individually selected from cyano, cyano-lower alkyl, halogen, halogen-lower alkoxy, halogen-lower alkyl, lower alkoxy, lower alkoxy-lower alkyl and lower alkyl;
$R^2$ is selected from the group consisting of
i) hydrogen,
ii) halogen, and
iii) lower alkyl;
$R^3$ is lower alkyl;
$R^4$ is selected from the group consisting of
i) hydrogen, and
ii) lower alkyl; and
$R^5$ is selected from the group consisting of
i) hydrogen, and
ii) lower alkyl;
or a pharmaceutically acceptable salt thereof.

4. The compound of claim 1, wherein $R^1$ is selected from the group consisting of
i) 1H-pyrazolyl, optionally substituted by 1-2 substituents individually selected from cycloalkyl, halogen, halogen-lower alkyl, lower alkyl,
ii) cycloalkyl, optionally substituted by 1-2 substituents individually selected from halogen and halogen-lower alkyl,
iii) lower alkenyl, optionally substituted by heteroaryl,
iv) lower alkyl, optionally substituted by 1-5 substituents individually selected from halogen and hydroxy,
v) furyl, optionally substituted by nitro,
vi) isoxazolyl, optionally substituted by 1-2 lower alkyl,
vii) oxazolyl, optionally substituted by 1-2 substituents individually selected from cycloalkyl, halogen-lower alkyl and lower alkyl,
viii) pyrazinyl, optionally substituted by 1-2 substituents individually selected from cycloalkyl-lower alkoxy, halogen, halogen-lower alkyl and lower alkyl,
ix) pyrazolyl, optionally substituted by 1-2 substituents individually selected from halogen and lower alkyl,
x) pyridazinyl, optionally substituted by 1-2 halogen,
xi) pyridinyl, optionally substituted by 1-2 substituents individually selected from amido, cyano, cycloalkyl-lower alkoxy, cycloalkyl-lower alkynyl, halogen, halogen-lower alkyl, lower alkyl and halogen-lower alkoxy; and
xii) pyrimidinyl, optionally substituted by 1-2 substituents individually selected from halogen and halogen-lower alkyl.

5. The compound of claim 1, wherein $R^1$ is selected from the group consisting of
i) pyridinyl,
ii) pyrazolyl,
iii) pyrazinyl,
iv) pyrimidinyl, and
v) pyridinyl substituted by 1-2 substituents individually selected from cyano, halogen, and halogen-lower alkyl.

6. The compound of claim 1, wherein $R^1$ is selected from the group consisting of (2,2,2-trifluoroethoxy)-pyridin-2-yl, (cyclopropylmethoxy)pyridine-2-yl, (trifluoromethyl)pyridine-2-yl, 1-(difluoromethyl)-1H-pyrazol-3-yl, 1-(trifluoromethyl)cycloprop-1-yl, 1-furyl-ethenyl, 1-methyl-1H-pyrazol-3-yl, 2-(chloromethyl)pyridin-4-yl, 2-(fluoromethyl)pyridin-4-yl, 2,2,2-trifluoro-1-hydroxy-1-methyl-2-ethyl, 2,2-difluorocycloprop-1-yl, 2,5-dimethyloxazol-4-yl, 2-ethyloxazol-4-yl, 2-methyl-5-(trifluoromethyl)pyridin-4-yl, 2-methyloxazol-4-yl, 3-(2,2,2-trifluoroethoxy)-pyridin-2-yl, 3,5-dichloropyrazin-2-yl, 3,5-dichloro-pyridin-2-yl, 3,5-difluoro-pyridin-2-yl, 3-chloro-5-cyano-pyridin-2-yl, 3-chloro-5-fluoro-pyridin-2-yl, 3-chloro-5-trifluoromethyl-pyridin-2-yl, 3-chloro-pyridin-2-yl, 3-fluoro-pyridin-2-yl, 3-trifluoromethyl-pyridin-2-yl, 4-chloro-1-(2,2,2-trifluoroethyl)-1H-pyrazol-3-yl, 4-chloro-1-(2,2-difluoroethyl)-1H-pyrazol-3-yl, 4-chloro-1-difluoromethyl-1H-pyrazol-3-yl, 4-chloro-1-ethyl-1H-pyrazole-3-yl, 4-chloro-1H-pyrazol-5-yl, 4-chloro-1-methyl-1H-pyrazol-3-yl, 4-chloro-3-cyclopropyl-1H-pyrazol-5-yl, 4-methyl-1H-pyrazol-5-yl, 4-methyl-isoxazol-3-yl, 5-(2,2,2-trifluoro-ethoxy)-pyridin-2-yl, 5-(2,2,3,3,3-pentafluoropropoxy)-pyridin-2-yl, 5-(2,2,3,3-tetrafluoropropoxy)-pyridin-2-yl, 5-(2,2-difluoroethoxy)-pyridin-2-yl, 5-(cyclopropylethynyl)-pyridin-2-yl, 5-(cyclopropylmethoxy)pyridine-2-yl, 5-(difluoromethoxy)-pyridin-2-yl, 5-(fluoromethoxy)-pyridin-2-yl, 5-(trifluoromethyl)-pyridin-2-yl, 5-amido-pyridin-2-yl, 5-chloro-3-fluoro-pyridine-2-yl, 5-chloro-3-methyl-pyridin-2-yl, 5-chloropyrazin-2-yl, 5-chloro-pyridin-2-yl, 5-chloro-pyrimidin-2-yl, 5-cyano-pyridin-1-oxide-2-yl, 5-cyano-pyridin-2-yl, 5-cyclopropyl-oxazol-4-yl, 5-ethyl-oxazol-4-yl, 5-fluoromethoxy-pyridin-2-yl, 5-fluoro-pyridin-2-yl, 5-isopropyl-oxazol-4-yl, 5-methyl-pyrazin-2-yl, 5-nitro-fur-2-yl, 5-trifluoromethyl-pyrazin-2-yl, 5-trifluoromethyl-pyrimidin-2-yl, 6-(cyclopropylmethoxy)-pyridin-3-yl, 6-chloropyridazin-3-yl, fur-2-yl, methyl, oxazolyl and pyridine-2-yl.

7. The compound of claim 1, wherein $R^1$ is selected from the group consisting of 5-Chloro-pyridine-2-yl, 3-Chloro-5-trifluoromethyl-pyridine-2-yl, 3-Chloro-5-fluoro-pyridine-2-yl, 3,5-Dichloro-pyridine-2-yl, 5-Cyano-pyridine-2-yl, 5-Chloro-3-fluoro-pyridine-2-yl, 5-Chloro-pyridine-2-yl and 3-Chloro-5-trifluoromethyl-pyridine-2-yl.

8. The compound of claim 1, wherein n is 1.

9. The compound of claim 1, wherein $R^2$ is halogen.

10. The compound of claim 9, wherein $R^2$ is fluoro.

11. The compound of claim 1, wherein $R^3$ is methyl.

12. The compound of claim 1, wherein $R^4$ is hydrogen.

13. The compound of claim 1, wherein $R^4$ is methyl.

14. The compound of claim 1, wherein $R^5$ is hydrogen.

15. The compound of claim 1, wherein $R^5$ is methyl.

16. The compound of claim 1, selected from the group consisting of

5-Chloro-pyridine-2-carboxylic acid [3-((R)-2-amino-5,5-difluoro-4-methyl-5,6-dihydro-4H-[1,3]oxazin-4-yl)-4-fluoro-phenyl]-amide, 5-Fluoro-pyridine-2-carboxylic acid [3-((R)-2-amino-5,5-difluoro-4-methyl-5,6-dihydro-4H-[1,3]oxazin-4-yl)-4-fluoro-phenyl]-amide, 3-Chloro-pyridine-2-carboxylic acid [3-((R)-2-amino-5,5-difluoro-4-methyl-5,6-dihydro-4H-[1,3]oxazin-4-yl)-4-fluoro-phenyl]-amide, 3,5-Difluoro-pyridine-2-carboxylic acid [3-((R)-2-amino-5,5-difluoro-4-methyl-5,6-dihydro-4H-[1,3]oxazin-4-yl)-4-fluoro-phenyl]-amide, 3-Chloro-5-trifluoromethyl-pyridine-2-carboxylic acid [3-((R)-2-amino-5,5-difluoro-4-methyl-5,6-dihydro-4H-[1,3]oxazin-4-yl)-4-fluoro-phenyl]-amide, 3-Trifluoromethyl-pyridine-2-carboxylic acid [3-((R)-2-amino-5,5-difluoro-4-methyl-5,6-dihydro-4H-[1,3]oxazin-4-yl)-4-fluoro-phenyl]-amide, 3-Chloro-5-fluoro-pyridine-2-carboxylic acid [3-((R)-2-amino-5,5-difluoro-4-methyl-5,6-dihydro-4H-[1,3]oxazin-4-yl)-4-fluoro-phenyl]-amide, 3,5-Dichloro-pyridine-2-carboxylic acid [3-((R)-2-amino-5,5-difluoro-4-methyl-5,6-dihydro-4H-[1,3]oxazin-4-yl)-4-fluoro-phenyl]-amide, Pyridine-2-carboxylic acid [3-((R)-2-amino-5,5-difluoro-4-methyl-5,6-dihydro-4H-[1,3]oxazin-4-yl)-4-fluoro-phenyl]-amide, and 3-Fluoro-pyridine-2-carboxylic acid [3-((R)-2-amino-5,5-difluoro-4-methyl-5,6-dihydro-4H-[1,3]oxazin-4-yl)-4-fluoro-phenyl]-amide or a pharmaceutical acceptable salt thereof.

17. The compound of claim 1, selected from the group consisting of

5-Cyano-pyridine-2-carboxylic acid [3-((R)-2-amino-5,5-difluoro-4-methyl-5,6-dihydro-4H-[1,3]oxazin-4-yl)-4-fluoro-phenyl]-amide, 5-Cyano-pyridine-2-carboxylic acid [3-((R)-2-amino-5,5-difluoro-4-methyl-5,6-dihydro-4H-[1,3]oxazin-4-yl)-4-fluoro-phenyl]-amide hydrochloride, 5-Cyano-pyridine-2-carboxylic acid [3-((R)-2-amino-5,5-difluoro-4-methyl-5,6-dihydro-4H-[1,3]oxazin-4-yl)-4-fluoro-phenyl]-amide, 5-Chloro-pyrimidine-2-carboxylic acid [3-((R)-2-amino-5,5-difluoro-4-methyl-5,6-dihydro-4H-[1,3]oxazin-4-yl)-4-fluoro-phenyl]-amide, 5-Chloro-3-methyl-pyridine-2-carboxylic acid [3-((R)-2-amino-5,5-difluoro-4-methyl-5,6-dihydro-4H-[1,3]oxazin-4-yl)-4-fluoro-phenyl]-amide, 5-(2,2,2-Trifluoro-ethoxy)-pyridine-2-carboxylic acid [3-((R)-2-amino-5,5-difluoro-4-methyl-5,6-dihydro-4H-[1,3]oxazin-4-yl)-4-fluoro-phenyl]-amide, 5-Chloro-3-fluoro-pyridine-2-carboxylic acid [3-((R)-2-amino-5,5-difluoro-4-methyl-5,6-dihydro-4H-[1,3]oxazin-4-yl)-4-fluoro-phenyl]-amide, 5-Trifluoromethyl-pyrimidine-2-carboxylic acid [3-((R)-2-amino-5,5-difluoro-4-methyl-5,6-dihydro-4H-[1,3]oxazin-4-yl)-4-fluoro-phenyl]-amide, 5-Trifluoromethyl-pyrazine-2-carboxylic acid [3-((R)-2-amino-5,5-difluoro-4-methyl-5,6-dihydro-4H-[1,3]oxazin-4-yl)-4-fluoro-phenyl]-amide, and 4-Chloro-1-methyl-1H-pyrazole-3-carboxylic acid [3-((R)-2-amino-5,5-difluoro-4-methyl-5,6-dihydro-4H-[1,3]oxazin-4-yl)-4-fluoro-phenyl]-amide or a pharmaceutical acceptable salt thereof.

18. The compound of claim 1, selected from the group consisting of

5-Chloro-pyridine-2-carboxylic acid [3-((R)-2-amino-5,5-difluoro-4,6,6-trimethyl-5,6-dihydro-4H-[1,3]oxazin-4-yl)-4-fluoro-phenyl]-amide, 3-Chloro-5-trifluoromethyl-pyridine-2-carboxylic acid [3-((R)-2-amino-5,5-difluoro-4,6,6-trimethyl-5,6-dihydro-4H-[1,3]oxazin-4-yl)-4-fluoro-phenyl]-amide, 5-Cyano-pyridine-2-carboxylic acid [3-((R)-2-amino-5,5-difluoro-4,6,6-trimethyl-5,6-dihydro-4H-[1,3]oxazin-4-yl)-4-fluoro-phenyl]-amide, (R)—N-(3-(2-amino-5,5-difluoro-4,6,6-trimethyl-5,6-dihydro-4H-1,3-oxazin-4-yl)-4-fluorophenyl)-3-chloro-5-cyanopicolinamide hydrochloride, (R)—N-(3-(2-amino-5,5-difluoro-4,6,6-trimethyl-5,6-dihydro-4H-1,3-oxazin-4-yl)-4-fluorophenyl)-3-chloro-5-cyanopicolinamide, (R)—N-(3-(2-amino-5,5-difluoro-4,6,6-trimethyl-5,6-dihydro-4H-1,3-oxazin-4-yl)-4-fluorophenyl)-3,5-dichloropicolinamide hydrochloride, (R)—N-(3-(2-amino-5,5-difluoro-4,6,6-trimethyl-5,6-dihydro-4H-1,3-oxazin-4-yl)-4-fluorophenyl)-3,5-dichloropicolinamide, (R)—N-(3-(2-amino-5,5-difluoro-4,6,6-trimethyl-5,6-dihydro-4H-1,3-oxazin-4-yl)-4-fluorophenyl)-5-chloro-3-fluoropicolinamide, (R)—N-(3-(2-amino-5,5-difluoro-4,6,6-trimethyl-5,6-dihydro-4H-1,3-oxazin-4-yl)-4-fluorophenyl)-5-(trifluoromethyl)picolinamide, and (R)—N-(3-(2-amino-5,5-difluoro-4,6,6-trimethyl-5,6-dihydro-4H-1,3-oxazin-4-yl)-4-fluorophenyl)-5-(fluoromethoxy)picolinamide or a pharmaceutical acceptable salt thereof.

19. The compound of claim 1, selected from the group consisting of (R)—N-(3-(2-amino-5,5-difluoro-4,6,6-trimethyl-5,6-dihydro-4H-1,3-oxazin-4-yl)-4-fluorophenyl)-5-(difluoromethoxy)picolinamide, (R)—N-(3-(2-amino-5,5-difluoro-4,6,6-trimethyl-5,6-dihydro-4H-1,3-oxazin-4-yl)-4-fluorophenyl)-5-(2,2-difluoroethoxy)picolinamide, 5-(2,2,2-Trifluoro-ethoxy)-pyridine-2-carboxylic acid [3-((R)-2-amino-5,5-difluoro-4,6,6-trimethyl-5,6-dihydro-4H-[1,3]oxazin-4-yl)-4-fluoro-phenyl]-amide, 5-(2,2,3,3-Tetrafluoro-propoxy)-pyridine-2-carboxylic acid [3-((R)-2-amino-5,5-difluoro-4,6,6-trimethyl-5,6-dihydro-4H-[1,3]oxazin-4-yl)-4-fluoro-phenyl]-amide hydrochloride, 5-(2,2,3,3-Tetrafluoro-propoxy)-pyridine-2-carboxylic acid [3-((R)-2-amino-5,5-difluoro-4,6,6-trimethyl-5,6-dihydro-4H-[1,3]oxazin-4-yl)-4-fluoro-phenyl]-amide, (R)—N-(3-(2-amino-5,5-difluoro-4,6,6-trimethyl-5,6-dihydro-4H-1,3-oxazin-4-yl)-4-fluorophenyl)-6-(cyclopropylmethoxy)nicotinamide, (R)—N-(3-(2-amino-5,5-difluoro-4,6,6-trimethyl-5,6-dihydro-4H-1,3-oxazin-4-yl)-4-fluorophenyl)-5-chloropyrimidine-2-carboxamide, 5-Trifluoromethyl-pyrimidine-2-carboxylic acid [3-((R)-2-amino-5,5-difluoro-4,6,6-trimethyl-5,6-dihydro-4H-[1,3]oxazin-4-yl)-4-fluoro-phenyl]-amide, (R)—N-(3-(2-amino-5,5-difluoro-4,6,6-trimethyl-5,6-dihydro-4H-1,3-oxazin-4-yl)-4-fluorophenyl)-5-methylpyrazine-2-carboxamide, and (R)—N-(3-(2-amino-5,5-difluoro-4,6,6-trimethyl-5,6-dihydro-4H-1,3-oxazin-4-yl)-4-fluorophenyl)-5-(trifluoromethyl)pyrazine-2-carboxamide or a pharmaceutical acceptable salt thereof.

20. The compound of claim 1, selected from the group consisting of (R)—N-(3-(2-amino-5,5-difluoro-4,6,6-trimethyl-5,6-dihydro-4H-1,3-oxazin-4-yl)-4-fluorophenyl)-5-(cyclopropylmethoxy)pyrazine-2-carboxamide, (R)—N-(3-(2-amino-5,5-difluoro-4,6,6-trimethyl-5,6-dihydro-4H-1,3-oxazin-4-yl)-4-fluorophenyl)-6-chloropyridazine-3-carboxamide hydrochloride, (R)—N-(3-(2-amino-5,5-difluoro-4,6,6-trimethyl-5,6-dihydro-4H-1,3-oxazin-4-yl)-4-fluorophenyl)-6-chloropyridazine-3-carboxamide, (R)—N-(3-(2-amino-5,5-difluoro-4,6,6-trimethyl-5,6-dihydro-4H-1,3-oxazin-4-yl)-4-fluorophenyl)-1-(difluoromethyl)-1H-pyrazole-3-carboxamide, 3-Chloro-5-cyano-pyridine-2-carboxylic acid [3-((R)-2-amino-5,5-difluoro-4-methyl-5,6-dihydro-4H-[1,3]oxazin-4-yl)-4-fluoro-phenyl]-amide, (S)—N-(3-(2-amino-5,5-difluoro-4-methyl-5,6-dihydro-4H-1,3-oxazin-4-yl)-4-fluorophenyl)-5-(cyclopropylethynyl)picolinamide, (R)—N-(3-(2-amino-5,5-difluoro-4-methyl-5,6-dihydro-4H-1,3-oxazin-4-yl)-4-fluorophenyl)-5-(difluoromethoxy)picolinamide, (R)—N-(3-(2-amino-5,5-difluoro-4-methyl-5,6-dihydro-4H-1,3-oxazin-4-yl)-4-fluorophenyl)-5-(fluoromethoxy)picolinamide, (R)—N-(3-(2-amino-5,5-difluoro-4-methyl-5,6-dihydro-4H-1,3-oxazin-4-yl)-4-fluorophenyl)-5-(2,2,3,3-tetrafluoropropoxy)picolinamide, and (R)—N-(3-(2-amino-5,5-difluoro-4-methyl-5,6-dihydro-4H-1,3-oxazin-4-yl)-4-fluorophenyl)-5-(2,2,3,3,3-pentafluoropropoxy)picolinamide or a pharmaceutical acceptable salt thereof.

21. The compound of claim 1, selected from the group consisting of (R)—N-(3-(2-amino-5,5-difluoro-4-methyl-5,6-dihydro-4H-1,3-oxazin-4-yl)-4-fluorophenyl)-5-(2,2-difluoroethoxy)picolinamide, (S)—N-(3-(2-amino-5,5-difluoro-4-methyl-5,6-dihydro-4H-1,3-oxazin-4-yl)-4-fluorophenyl)-5-(cyclopropylmethoxy)pyrazine-2-carboxamide, (R)—N-(3-(2-amino-5,5-difluoro-4-methyl-5,6-dihydro-4H-1,3-oxazin-4-yl)-4-fluorophenyl)-5-chloropyrazine-2-carboxamide, (R)—N-(3-(2-amino-5,5-difluoro-4-methyl-5,6-dihydro-4H-1,3-oxazin-4-yl)-4-fluorophenyl)-3,5-dichloropyrazine-2-carboxamide, (R)—N-(3-(2-amino-5,5-difluoro-4-methyl-5,6-dihydro-4H-1,3-oxazin-4-yl)-4,5-difluorophenyl)-5-cyanopicolinamide, (R)—N-(3-(2-amino-5,5-difluoro-4-methyl-5,6-dihydro-4H-1,3-oxazin-4-yl)-4-chlorophenyl)-5-chloropicolinamide, (R)—N-(3-(2-amino-5,5-difluoro-4-methyl-5,6-dihydro-4H-1,3-oxazin-4-yl)-4-chlorophenyl)-5-cyanopicolinamide, (R)—N-(3-(2-amino-5,5-difluoro-4-methyl-5,6-dihydro-4H-1,3-oxazin-4-yl)phenyl)-5-chloropicolinamide, (R)—N-(3-(2-amino-5,5-difluoro-4-methyl-5,6-dihydro-4H-1,3-oxazin-4-yl)phenyl)-5-cyanopicolinamide, and (R)—N-(3-(2-amino-5,5-difluoro-4-methyl-5,6-dihydro-4H-1,3-oxazin-4-yl)-4-fluorophenyl)-3-(2,2,2-trifluoroethoxy)picolinamide or a pharmaceutical acceptable salt thereof.

22. The compound of claim 1, selected from the group consisting of (R)—N-(3-(2-amino-5,5-difluoro-4-methyl-5,6-dihydro-4H-1,3-oxazin-4-yl)-4-fluorophenyl)oxazole-4-carboxamide, (R)—N-(3-(2-amino-5,5-difluoro-4-methyl-5,6-dihydro-4H-1,3-oxazin-4-yl)-4-fluorophenyl)-2-ethyloxazole-4-carboxamide, (R)—N-(3-(2-amino-5,5-difluoro-4-methyl-5,6-dihydro-4H-1,3-oxazin-4-yl)-4-fluorophenyl)-2-(chloromethyl)oxazole-4-carboxamide, (R)—N-(3-(2-amino-5,5-difluoro-4-methyl-5,6-dihydro-4H-1,3-oxazin-4-yl)-4-fluorophenyl)-2-methyloxazole-4-carboxamide, (R)—N-(3-(2-amino-5,5-difluoro-4-methyl-5,6-dihydro-4H-1,3-oxazin-4-yl)-4-fluorophenyl)-2,5-dimethyloxazole-4-carboxamide, (R)—N-(3-(2-amino-5,5-difluoro-4-methyl-5,6-dihydro-4H-1,3-oxazin-4-yl)-4-fluorophenyl)-2-methyl-5-(trifluoromethyl)oxazole-4-carboxamide, (R)—N-(3-(2-amino-5,5-difluoro-4-methyl-5,6-dihydro-4H-1,3-oxazin-4-yl)-4-fluorophenyl)-4-methylisoxazole-3-carboxamide, (R)—N-(3-(2-amino-5,5-difluoro-4-methyl-5,6-dihydro-4H-1,3-oxazin-4-yl)-4-fluorophenyl)-5-isopropyloxazole-4-carboxamide, (R)—N-(3-(2-amino-5,5-difluoro-4-methyl-5,6-dihydro-4H-1,3-oxazin-4-yl)-4-fluorophenyl)-1-methyl-1H-pyrazole-3-carboxamide, and (R)—N-(3-(2-amino-5,5-difluoro-4-methyl-5,6-dihydro-4H-1,3-oxazin-4-yl)-4-fluorophenyl)-1-(difluoromethyl)-1H-pyrazole-3-carboxamide or a pharmaceutical acceptable salt thereof.

23. The compound of claim 1, selected from the group consisting of (R)—N-(3-(2-amino-5,5-difluoro-4-methyl-5,6-dihydro-4H-1,3-oxazin-4-yl)-4-fluorophenyl)-4-chloro-1H-pyrazole-5-carboxamide, (R)—N-(3-(2-amino-5,5-difluoro-4-methyl-5,6-dihydro-4H-1,3-oxazin-4-yl)-4-fluorophenyl)-4-methyl-1H-pyrazole-5-carboxamide, (R)—N-(3-(2-amino-5,5-difluoro-4-methyl-5,6-dihydro-4H-1,3-oxazin-4-yl)-4-fluorophenyl)-4-chloro-3-cyclopropyl-1H-pyrazole-5-carboxamide, (R)—N-(3-(2-amino-5,5-difluoro-4-methyl-5,6-dihydro-4H-1,3-oxazin-4-yl)-4-fluorophenyl)-4-chloro-1-(2,2-difluoroethyl)-1H-pyrazole-3-carboxamide,
(R)—N-(3-(2-amino-5,5-difluoro-4-methyl-5,6-dihydro-4H-1,3-oxazin-4-yl)-4-fluorophenyl)-5-ethyloxazole-4-carboxamide formate,
(R)—N-(3-(2-amino-5,5-difluoro-4-methyl-5,6-dihydro-4H-1,3-oxazin-4-yl)-4-fluorophenyl)-5-cyclopropyloxazole-4-carboxamide formate,
4-Chloro-1-difluoromethyl-1H-pyrazole-3-carboxylic acid [3-((R)-2-amino-5,5-difluoro-4-methyl-5,6-dihydro-4H-[1,3]oxazin-4-yl)-4-fluoro-phenyl]-amide,
(R)—N2-(3-(2-amino-5,5-difluoro-4-methyl-5,6-dihydro-4H-1,3-oxazin-4-yl)-4-fluorophenyl)pyridine-2,5-dicarboxamide,
N-[3-((R)-2-Amino-5,5-difluoro-4-methyl-5,6-dihydro-4H-[1,3]oxazin-4-yl)-4-fluoro-phenyl]-acetamide,
N-(3-((R)-2-amino-5,5-difluoro-4-methyl-5,6-dihydro-4H-1,3-oxazin-4-yl)-4-fluorophenyl)-2,2-difluorocyclopropanecarboxamide, and
(R)—N-(3-(2-amino-5,5-difluoro-4-methyl-5,6-dihydro-4H-1,3-oxazin-4-yl)-4-fluorophenyl)-1-(trifluoromethyl)cyclopropanecarboxamide
or a pharmaceutical acceptable salt thereof.

24. The compound of claim 1, selected from the group consisting of
(R)—N-(3-((R)-2-amino-5,5-difluoro-4-methyl-5,6-dihydro-4H-1,3-oxazin-4-yl)-4-fluorophenyl)-3,3,3-trifluoro-2-hydroxy-2-methylpropanamide 2,2,2-trifluoroacetate,
(R)—N-(3-(2-amino-5,5-difluoro-4-methyl-5,6-dihydro-4H-1,3-oxazin-4-yl)-4-fluorophenyl)-4-chloro-1-ethyl-1H-pyrazole-3-carboxamide,
(R)—N-(3-(2-amino-5,5-difluoro-4-methyl-5,6-dihydro-4H-1,3-oxazin-4-yl)-4-fluorophenyl)-4-chloro-1-(2,2,2-trifluoroethyl)-1H-pyrazole-3-carboxamide,
(R)—N-(3-(2-amino-5,5-difluoro-4-methyl-5,6-dihydro-4H-1,3-oxazin-4-yl)-4-fluorophenyl)-2-(fluoromethyl)oxazole-4-carboxamide formate,
Furan-2-carboxylic acid [3-((R)-2-amino-5,5-difluoro-4-methyl-5,6-dihydro-4H-[1,3]oxazin-4-yl)-4-fluoro-phenyl]-amide,
5-Nitro-furan-2-carboxylic acid [3-((R)-2-amino-5,5-difluoro-4-methyl-5,6-dihydro-4H-[1,3]oxazin-4-yl)-4-fluoro-phenyl]-amide,
(E)-N-[3-((R)-2-Amino-5,5-difluoro-4-methyl-5,6-dihydro-4H-[1,3]oxazin-4-yl)-4-fluoro-phenyl]-3-furan-2-yl-acrylamide, and
(R)-2-(3-(2-amino-5,5-difluoro-4-methyl-5,6-dihydro-4H-1,3-oxazin-4-yl)-4-fluorophenylcarbamoyl)-5-cyanopyridine 1-oxide,
or a pharmaceutical acceptable salt thereof.

25. The compound of claim 1, selected from the group consisting of
5-Chloro-pyridine-2-carboxylic acid [3-((R)-2-amino-5,5-difluoro-4-methyl-5,6-dihydro-4H-[1,3]oxazin-4-yl)-4-fluoro-phenyl]-amide,
5-Fluoro-pyridine-2-carboxylic acid [3-((R)-2-amino-5,5-difluoro-4-methyl-5,6-dihydro-4H-[1,3]oxazin-4-yl)-4-fluoro-phenyl]-amide,
3-Chloro-pyridine-2-carboxylic acid [3-((R)-2-amino-5,5-difluoro-4-methyl-5,6-dihydro-4H-[1,3]oxazin-4-yl)-4-fluoro-phenyl]-amide,
3,5-Difluoro-pyridine-2-carboxylic acid [3-((R)-2-amino-5,5-difluoro-4-methyl-5,6-dihydro-4H-[1,3]oxazin-4-yl)-4-fluoro-phenyl]-amide,
3-Chloro-5-trifluoromethyl-pyridine-2-carboxylic acid [3-((R)-2-amino-5,5-difluoro-4-methyl-5,6-dihydro-4H-[1,3]oxazin-4-yl)-4-fluoro-phenyl]-amide,
3-Trifluoromethyl-pyridine-2-carboxylic acid [3-((R)-2-amino-5,5-difluoro-4-methyl-5,6-dihydro-4H-[1,3]oxazin-4-yl)-4-fluoro-phenyl]-amide,
3-Chloro-5-fluoro-pyridine-2-carboxylic acid [3-((R)-2-amino-5,5-difluoro-4-methyl-5,6-dihydro-4H-[1,3]oxazin-4-yl)-4-fluoro-phenyl]-amide,
3,5-Dichloro-pyridine-2-carboxylic acid [3-((R)-2-amino-5,5-difluoro-4-methyl-5,6-dihydro-4H-[1,3]oxazin-4-yl)-4-fluoro-phenyl]-amide,
Pyridine-2-carboxylic acid [3-((R)-2-amino-5,5-difluoro-4-methyl-5,6-dihydro-4H-[1,3]oxazin-4-yl)-4-fluoro-phenyl]-amide, and
3-Fluoro-pyridine-2-carboxylic acid [3-((R)-2-amino-5,5-difluoro-4-methyl-5,6-dihydro-4H-[1,3]oxazin-4-yl)-4-fluoro-phenyl]-amide.

26. The compound of claim 1, selected from the group consisting of
5-Cyano-pyridine-2-carboxylic acid [3-((R)-2-amino-5,5-difluoro-4-methyl-5,6-dihydro-4H-[1,3]oxazin-4-yl)-4-fluoro-phenyl]-amide,
5-Chloro-pyrimidine-2-carboxylic acid [3-((R)-2-amino-5,5-difluoro-4-methyl-5,6-dihydro-4H-[1,3]oxazin-4-yl)-4-fluoro-phenyl]-amide,
5-Chloro-3-methyl-pyridine-2-carboxylic acid [3-((R)-2-amino-5,5-difluoro-4-methyl-5,6-dihydro-4H-[1,3]oxazin-4-yl)-4-fluoro-phenyl]-amide,
5-(2,2,2-Trifluoro-ethoxy)-pyridine-2-carboxylic acid [3-((R)-2-amino-5,5-difluoro-4-methyl-5,6-dihydro-4H-[1,3]oxazin-4-yl)-4-fluoro-phenyl]-amide,
5-Chloro-3-fluoro-pyridine-2-carboxylic acid [3-((R)-2-amino-5,5-difluoro-4-methyl-5,6-dihydro-4H-[1,3]oxazin-4-yl)-4-fluoro-phenyl]-amide,
5-Trifluoromethyl-pyrimidine-2-carboxylic acid [3-((R)-2-amino-5,5-difluoro-4-methyl-5,6-dihydro-4H-[1,3]oxazin-4-yl)-4-fluoro-phenyl]-amide,
5-Trifluoromethyl-pyrazine-2-carboxylic acid [3-((R)-2-amino-5,5-difluoro-4-methyl-5,6-dihydro-4H-[1,3]oxazin-4-yl)-4-fluoro-phenyl]-amide,
4-Chloro-1-methyl-1H-pyrazole-3-carboxylic acid [3-((R)-2-amino-5,5-difluoro-4-methyl-5,6-dihydro-4H-[1,3]oxazin-4-yl)-4-fluoro-phenyl]-amide,
5-Chloro-pyridine-2-carboxylic acid [3-((R)-2-amino-5,5-difluoro-4,6,6-trimethyl-5,6-dihydro-4H-[1,3]oxazin-4-yl)-4-fluoro-phenyl]-amide, and
3-Chloro-5-trifluoromethyl-pyridine-2-carboxylic acid [3-((R)-2-amino-5,5-difluoro-4,6,6-trimethyl-5,6-dihydro-4H-[1,3]oxazin-4-yl)-4-fluoro-phenyl]-amide.

27. The compound of claim 1, selected from the group consisting of
5-Chloro-pyridine-2-carboxylic acid [3-((R)-2-amino-5,5-difluoro-4-methyl-5,6-dihydro-4H-[1,3]oxazin-4-yl)-4-fluoro-phenyl]-amide,
3-Chloro-5-trifluoromethyl-pyridine-2-carboxylic acid [3-((R)-2-amino-5,5-difluoro-4-methyl-5,6-dihydro-4H-[1,3]oxazin-4-yl)-4-fluoro-phenyl]-amide,
3-Chloro-5-fluoro-pyridine-2-carboxylic acid [3-((R)-2-amino-5,5-difluoro-4-methyl-5,6-dihydro-4H-[1,3]oxazin-4-yl)-4-fluoro-phenyl]-amide,
3,5-Dichloro-pyridine-2-carboxylic acid [3-((R)-2-amino-5,5-difluoro-4-methyl-5,6-dihydro-4H-[1,3]oxazin-4-yl)-4-fluoro-phenyl]-amide,
5-Cyano-pyridine-2-carboxylic acid [3-((R)-2-amino-5,5-difluoro-4-methyl-5,6-dihydro-4H-[1,3]oxazin-4-yl)-4-fluoro-phenyl]-amide, 5-Chloro-3-fluoro-pyridine-2-carboxylic acid [3-((R)-2-amino-5,5-difluoro-4-methyl-5,6-dihydro-4H-[1,3]oxazin-4-yl)-4-fluoro-phenyl]-amide, 5-Chloro-pyridine-2-carboxylic acid [3-((R)-2-amino-5,5-difluoro-4,6,6-trimethyl-5,6-dihydro-4H-[1,3]oxazin-4-yl)-4-fluoro-phenyl]-amide, and 3-Chloro-5-trifluoromethyl-pyridine-2-carboxylic acid [3-((R)-2-amino-5,5-difluoro-4,6,6-trimethyl-5,6-dihydro-4H-[1,3]oxazin-4-yl)-4-fluoro-phenyl]-amide.

28. A pharmaceutical composition comprising a therapeutically effective amount of a compound of formula I

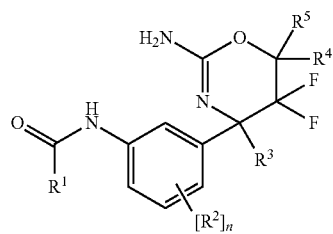

wherein
$R^1$ is selected from the group consisting of
  xi) aryl,
  xii) aryl substituted by 1-4 substituents individually selected from cyano, cyano-lower alkyl, halogen, halogen-lower alkoxy, halogen-lower alkyl, lower alkoxy, lower alkoxy-lower alkyl and lower alkyl,
  xiii) heteroaryl,
  xiv) heteroaryl substituted by 1-4 substituents individually selected from amido, cyano, cyano-lower alkyl, cycloalkyl, cycloalkyl-lower alkenyl, cycloalkyl-lower alkynyl, cycloalkyl-lower alkyl, cycloalkyl-lower alkoxy, halogen, halogen-lower alkoxy, halogen-lower alkyl, lower alkoxy, lower alkoxy-lower alkyl, lower alkenyl, lower alkynyl, lower alkyl and nitro;
  xv) lower alkyl,
  xvi) lower alkyl substituted by 1-5 substituents individually selected from cyano, halogen, hydroxy and lower alkoxy;
  xvii) lower alkenyl,
  xviii) lower alkenyl substituted by 1-4 substituents individually selected from cyano, cyano-lower alkyl, halogen, halogen-lower alkoxy, halogen-lower alkyl, heteroaryl, lower alkoxy, lower alkoxy-lower alkyl and lower alkyl,
  xix) cycloalkyl, and
  xx) cycloalkyl substituted by 1-4 substituents individually selected from cyano, cyano-lower alkyl, halogen, halogen-lower alkoxy, halogen-lower alkyl, lower alkoxy, lower alkoxy-lower alkyl and lower alkyl,
$R^2$ is selected from the group consisting of
  iv) hydrogen,
  v) halogen, and
  vi) lower alkyl;
$R^3$ is lower alkyl;
$R^4$ is selected from the group consisting of
  iii) hydrogen, and
  iv) lower alkyl;
$R^5$ is selected from the group consisting of
  iii) hydrogen, and
  iv) lower alkyl; and
n is 0, 1 or 2;
or a pharmaceutically acceptable salt thereof
and a pharmaceutically acceptable carrier.

29. The compound of claim 17, which is selected from the group consisting of 5-Cyano-pyridine-2-carboxylic acid [3-((R)-2-amino-5,5-difluoro-4-methyl-5,6-dihydro-4H-[1,3]oxazin-4-yl)-4-fluoro-phenyl]-amide and a pharmaceutically acceptable salt thereof.

30. The compound of claim 29, which is 5-Cyano-pyridine-2-carboxylic acid [3-((R)-2-amino-5,5-difluoro-4-methyl-5,6-dihydro-4H-[1,3]oxazin-4-yl)-4-fluoro-phenyl]-amide.

31. The compound of claim 29, which is 5-Cyano-pyridine-2-carboxylic acid [3-((R)-2-amino-5,5-difluoro-4-methyl-5,6-dihydro-4H-[1,3]oxazin-4-yl)-4-fluoro-phenyl]-amide hydrochloride.

* * * * *